United States Patent [19]

Beavers et al.

[11] Patent Number: 4,975,369
[45] Date of Patent: Dec. 4, 1990

[54] RECOMBINANT AND CHIMERIC KS1/4 ANTIBODIES DIRECTED AGAINST A HUMAN ADENOCARCINOMA ANTIGEN

[75] Inventors: Lisa S. Beavers, Trafalgar; Thomas F. Bumol, Carmel; Robert A. Gadski; Barbara J. Weigel, both of Indianapolis, all of Ind.

[73] Assignee: Eli Lilly and Company, Indianapolis, Ind.

[21] Appl. No.: 184,522

[22] Filed: Apr. 21, 1988

[51] Int. Cl.[5] .................. C12N 5/10; C12N 1/00; C12N 15/00
[52] U.S. Cl. .................. 435/69.1; 536/27; 435/320; 435/172.3; 435/240.1; 935/70; 935/71; 935/41; 530/387
[58] Field of Search ............. 435/68, 70, 172.3, 235, 435/320, 240.1, 69.1; 536/27; 530/387; 935/70, 71

[56] References Cited

U.S. PATENT DOCUMENTS 4,816,567  3/1989  Cabily .................. 530/387

FOREIGN PATENT DOCUMENTS 0120694  10/1984  European Pat. Off. .
0125023  11/1984  European Pat. Off. .
0173494  3/1986   European Pat. Off. .
0245949  11/1987  European Pat. Off. .
WO86/01533 3/1986  PCT Int'l Appl. .

OTHER PUBLICATIONS

Shaw, D. R. et al, Jun. 15, 1987, J. Immunol. 138(12), 4534–4538.
Sikorav J–L. et al, 1980, Nucleic Acids Res., 8(14), 3143–3155.
Hamyn, P. H. et al., 1981, Nucleic Acids Res., 9, 4485–4494.
Yamawaki-Kataoka, Y., et al, 1987, Nucleic Acids Res. 9(6), 1365–1381.
Neuberger et al., 1984, Nature, 312:604–608.
Caton, A. J., 1986, Hybridoma, 5:511–516.
Bumol et al., in Ceriani, R. L. ed., Immunological Approaches to the Diagnosis and Therapy of Breast Cancer.
Varki et al., 1984, Cancer Research, 44:681–687.
Spearman et al., 1987, J. Pharmacol. and Exp. Therapeutics, 241:695–703.
Sahagan et al., 1986, J. Immunol., 21:1066–1074.
EP 0171496, 2/19/86, European Patent.
Sun et al., 1986, Hybridoma, 5: 517–520.
WO 87/02671, 5/7/87, PCT.
Sun et al., 1987, PNAS, 84:214–218.
Liu et al., 1987, PNAS, 84:3439–3443.
Bumol, T. F. in Reisfeld, R. A. and Sells, S. eds., Monoclonal Antibodies and Cancer Therapy.
Morrison et al., 1986, The Mount Sinai J. of Med., 53:175–180.
Oi et al., 1983, PNAS, 80:825–829.
Grinnell et al., 1986, Molecular and Cellular Biology, 6:3596–3605.
Boullianne et al., 1984, Nature, 312:643–646.

*Primary Examiner*—Richard A. Schwartz
*Assistant Examiner*—Michelle S. Marks
*Attorney, Agent, or Firm*—Douglas K. Norman; Leroy Whitaker

[57] ABSTRACT

The present invention comprises novel recombinant DNA compounds which encode monoclonal antibody KS1/4 and chimeric derivatives of monoclonal antibody KS1/4. Eukaryotic expression vectors have been constructed that comprise novel KS1/4-encoding DNA and drive expression of KS1/4 when transformed into an appropriate host cell. The novel expression vectors can be used to create modified and chimeric derivatives of KS1/4. The recombinant-produced KS1/4, KS1/4 derivatives and KS1/4 chimeras are useful for the diagnosis, prognosis and treatment of disease states including adenocarcinoma.

77 Claims, 15 Drawing Sheets

BK Virus pBKneo1 pLPcat pBLcat pLPC pSV2hyg pLPChyg1 pLPChd phd pGKC2310 pG2A52

CHKC2-6

CHKC2-18

CH2A5

CH2A5IG2

CH2A5IG3

CH2A5IG4

RECOMBINANT AND CHIMERIC KS1/4 ANTIBODIES DIRECTED AGAINST A HUMAN ADENOCARCINOMA ANTIGEN

SUMMARY OF THE INVENTION

The present invention provides novel DNA compounds and recombinant DNA cloning vectors that encode monoclonal antibody KS1/4, as well as mouse/human chimeric antibodies derived from KS1/4. The vectors allow expression of the novel DNA compounds in non-lymphoid eukaryotic cells. The present invention also provides host cells transformed with these novel cloning vectors. The transformed host cells express the recombinant or chimeric KS1/4 antibodies, or derivatives thereof. Many of the present DNA compounds can be used to produce KS1/4 derivatives never before synthesized either in nature or in the laboratory, and the present invention also comprises these unique molecules.

Monoclonal antibody KS1/4 is a murine antibody which specifically binds to the ~40,000 dalton cell surface antigen found in high density on adenocarcinoma cells and found also on normal epithelial cells. This antibody has been shown to be effective for the in vitro detection of disease, as well as the in vivo diagnosis and treatment of adenocarcinoma. Recent studies have confirmed that KS1/4-drug conjugates demonstrate a dose-dependent suppression of tumor growth. See, Spearman et al., 1987, J. Pharmacol. and Exp. Therapeutics 241:695–703; Bumol et al., in Ceriani, R. L. ed. Immunological Approaches to the Diagnosis and Therapy of Breast Cancer. New York and London: Plenum Press; 1987, 205–215; and Bumol, in Reisfeld, R. A. and Sell, S. eds. Monoclonal Antibodies and Cancer Therapy. New York: Alan R. Liss, Inc; 1985, 257–259.

One problem with the use of murine antibodies in human subjects arises when the cancer patient's immune system creates antibodies against the murine immunoglobulins. This immune response does not occur in all patients, but when it does, it results in a gradual decline in the efficacy of treatment during multiple dose regimens. The patient's immune response can cause a rapid clearance of the murine antibody from the patient's bloodstream. Such a response could also lead to more severe reactions like anaphylaxis or serum sickness. This immunogenicity precludes multiple dose administration of the antibody and therefore decreases the clinical value of the treatment.

Human monoclonal antibodies are difficult to prepare, therefore chimeric antibodies are constructed to avoid immunological problems. Chimeric antibodies comprise an antigen specific or variable region derived from one species joined with the constant region from a different species. See, Oi and Morrison, BioTechniques 4:214–221 (1986). Inasmuch as the immune response is often directed against the constant region, the replacement of a murine constant region with a human constant region will greatly diminish a patient's immunological reaction. Accordingly, chimeric antibodies are highly desirable for the treatment of disease.

The general concept of chimeric antibodies has been described, yet the development of novel chimeric antibodies having certain specificities is still needed. The present invention discloses recombinant DNA and amino acid sequences which comprise the entire KS1/4 monoclonal antibody molecule. These sequences have been manipulated to express chimeric antibodies which have the same tissue specificity as KS1/4, but which comprise constant regions derived from human sources. The invention therefore will allow a therapeutic regimen with the same tissue specificity of monoclonal antibody KS1/4 but with greatly reduced immunological side effects.

The present invention further comprises the recombinant DNA and amino acid sequences of KS1/4. The knowledge of these sequences allows skilled artisans to develop novel KS1/4 derivatives with modified affinity for the KS1/4 antigen. The present invention further comprises methods of producing recombinant and chimeric KS1/4 in non-lymphoid cell lines, thereby circumventing the problems often arising from dual secretion of heterologous antibodies in lymphoid cells.

For purposes of the present invention, as disclosed and claimed herein, the following terms are as defined below.

A—deoxyadenosine.

Ala—an alanine residue.

$Ap^R13$ the ampicillin-resistant phenotype or gene conferring same.

Arg—an arginine residue.

Asn—an asparagine residue.

Asp—an aspartic acid residue.

C—deoxycytosine.

Chimeric antibody—an antibody comprising a variable region from one species, typically mouse, joined to a constant region from a second and different species, typically human.

Cys—a cysteine residue.

dhfr—the dihydrofolate reductase phenotype or gene conferring same.

Enh—an enhancer sequence obtained from the BK virus.

G—deoxyguanosine.

Gln—a glutamine residue.

Glu—a glutamic acid residue.

Gly—a glycine residue.

$G418^R$—the G418-resistant phenotype or gene conferring same. May also be identified as $Km^R$.

His—a histidine residue.

$Hm^R$—the hygromycin-resistant phenotype or gene conferring same.

Ile—an isoleucine residue.

IVS—DNA encoding an intron, also called an intervening sequence.

KSA—the ~40,000 dalton cell surface glycoprotein antigen of UCLA-P3 cells that is recognized by monoclonal antibody KS1/4.

KS1/4—a murine monoclonal antibody derived from a hybridoma cell line, said antibody recognizing the ~40,000 dalton glycoprotein antigen found on the cell surface of P3-UCLA cells.

Leu—a leucine residue.

LP—a DNA segment comprising the promoter activity of the adenovirus late promoter.

Lys—a lysine residue.

Met—a methionine residue.

MoAB—monoclonal antibody.

Nascent protein—the polypeptide produced upon translation of a mRNA transcript, prior to any post-translational modifications.

pA—a DNA sequence encoding a polyadenylation signal.

Phe—a phenylalanine residue.

pL—a DNA segment comprising the promoter activity of the bacteriophage λ leftward promoter.

Pro—a proline residue.

Promoter—a DNA sequence that directs transcription of DNA into RNA.

Recombinant DNA Cloning Vector—any autonomously replicating agent, including, but not limited to, plasmids and phages, comprising a DNA molecule to which one or more additional DNA segments can be or have been added.

Recombinant DNA Expression Vector—any recombinant DNA cloning vector into which a promoter has been incorporated.

Recombinant KS1/4—monoclonal antibody KS1/4 molecules expressed in cells transformed by a vector which drives expression of KS1/4.

Replicon—A DNA sequence that controls and allows for autonomous replication of a plasmid or other vector.

Restriction Fragment—any linear DNA sequence generated by the action of one or more restriction endonuclease enzymes.

Sensitive Host Cell—a host cell that cannot grow in the presence of a given antibiotic or other toxic compound without a DNA segment that confers resistance thereto.

Ser—a serine residue.

Structural Gene—any DNA sequence that encodes a functional polypeptide, inclusive of translational start and stop signals.

T—deoxythymidine.

Tc$^R$—the tetracycline-resistant phenotype or gene conferring same.

Thr—a threonine residue.

Trp—a tryptophane residue.

Tyr—a tyrosine residue.

Val—a valine residue.

DETAILED DESCRIPTION OF THE INVENTION

Figure 1:
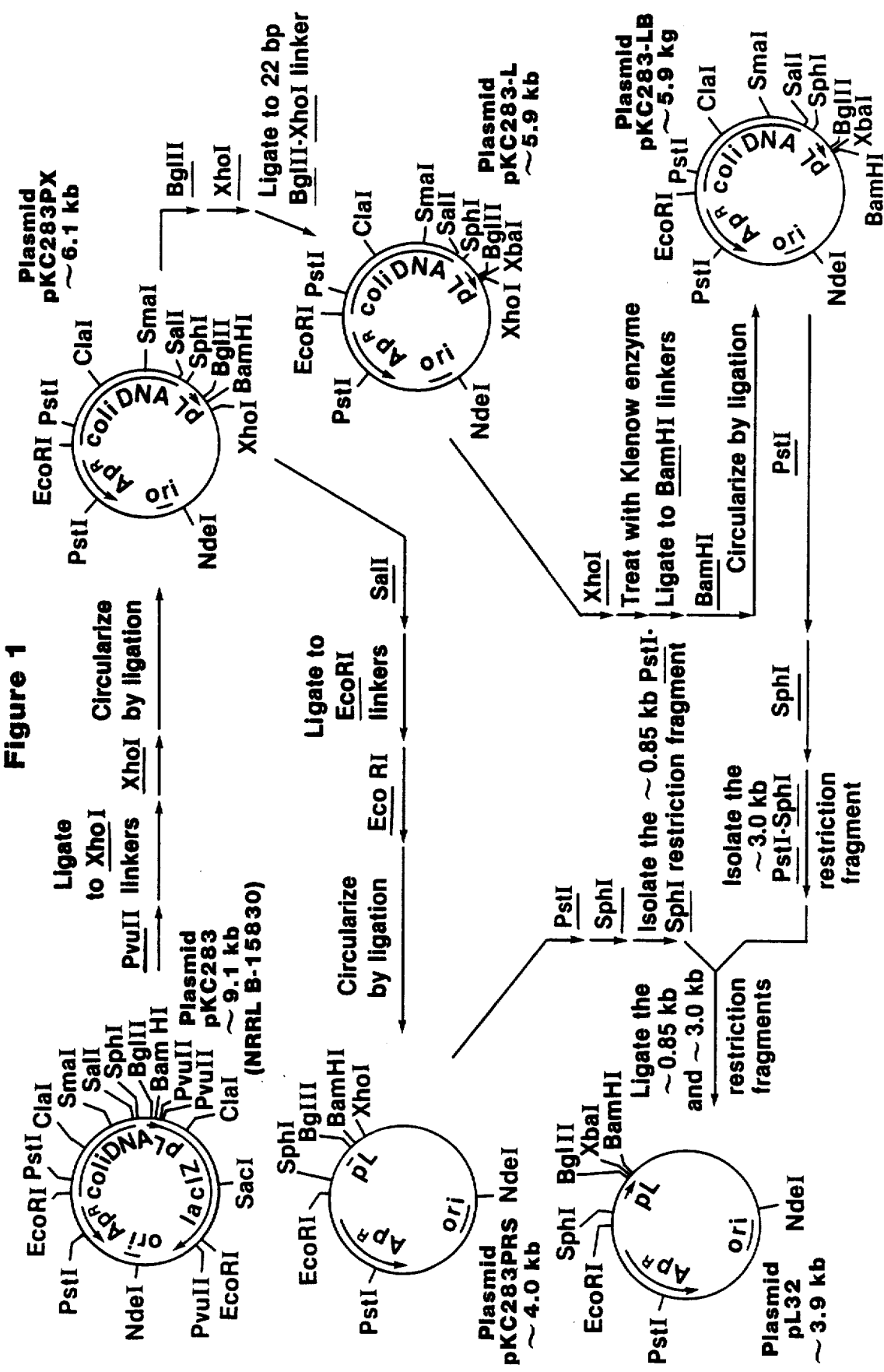
FIG. 1—a schematic showing the construction of Plasmid pL32. For the purpose of this disclosure, the Figures are not drawn exactly to scale.

The present invention is a recombinant DNA compound which comprises DNA encoding a monoclonal antibody light chain wherein the light chain is the light chain of monoclonal antibody KS1/4 and has an amino acid residue sequence substantially the same as:

---
Gln Ile Leu Leu Thr Gln Ser Pro Ala Ile Met Ser Ala Ser
Pro Gly Glu Lys Val Thr Met Thr Cys Ser Ala Ser Ser Ser Val
Ser Tyr Met Leu Trp Tyr Gln Gln Lys Pro Gly Ser Ser Pro Lys
Pro Trp Ile Phe Asp Thr Ser Asn Leu Ala Ser Gly Phe Pro Ala
Arg Phe Ser Gly Ser Gly Ser Gly Thr Ser Tyr Ser Leu Ile Ile
Ser Ser Met Glu Ala Glu Asp Ala Ala Thr Tyr Tyr Cys His Gln
Arg Ser Gly Tyr Pro Tyr Thr Phe Gly Gly Gly Thr Lys Leu
Glu Ile Lys Arg Ala Asp Ala Ala Pro Thr Val Ser Ile Phe
Pro Pro Ser Ser Glu Gln Leu Thr Ser Gly Gly Ala Ser Val
Val Cys Phe Leu Asn Asn Phe Tyr Pro Lys Asp Ile Asn Val
Lys Trp Lys Ile Asp Gly Ser Glu Arg Gln Asn Gly Val Leu
Asn Ser Trp Thr Asp Gln Asp Ser Lys Asp Ser Thr Tyr Ser
Met Ser Ser Thr Leu Thr Leu Thr Lys Asp Glu Tyr Glu Arg
His Asn Ser Tyr Thr Cys Glu Ala Thr His Lys Thr Ser Thr
Ser Pro Ile Val Lys Ser Phe Asn Arg Asn Glu Cys
---

Furthermore, the present invention is a recombinant DNA compound which comprises DNA encoding a monoclonal antibody heavy chain wherein the heavy chain is the heavy chain or monoclonal antibody KS1/4 and has an amino acid residue sequence substantially the same as:

---
Gln Ile Gln Leu Val Gln Ser Gly Pro Glu Leu Lys
Lys Pro Gly Glu Thr Val Lys Ile Ser Cys Lys Ala Ser Gly Tyr
Thr Phe Thr Asn Tyr Gly Met Asn Trp Val Lys Gln Thr Pro
Gly Lys Gly Leu Lys Trp Met Gly Trp Ile Asn Thr Tyr Thr Gly
Glu Pro Thr Tyr Ala Asp Asp Phe Lys Gly Arg Phe Ala Phe
Ser Leu Glu Thr Ser Ala Ser Thr Ala Phe Leu Gln Ile Gln Gln
Pro Gln Asn Met Arg Thr Met Ala Thr Tyr Phe Cys Val Arg
Phe Ile Ser Lys Gly Asp Tyr Trp Gly Gln Gly Thr Ser Val Thr
Val Ser Ser Ala Lys Thr Thr Ala Pro Ser Val Tyr Pro Leu Ala
Pro Val Cys Gly Asp Thr Thr Gly Ser Ser Val Thr Leu Gly
Cys Leu Val Lys Gly Tyr Phe Pro Glu Pro Val Thr Leu Thr
Trp Asn Ser Gly Ser Leu Ser Ser Gly Val His Thr Phe Pro Ala
Val Leu Gln Ser Asp Leu Tyr Thr Leu Ser Ser Ser Val Thr Val
Thr Ser Ser Thr Trp Pro Ser Gln Ser Ile Thr Cys Asn Val Ala
His Pro Ala Ser Ser Thr Lys Val Asp Lys Lys Ile Glu Pro Arg
Gly Pro Thr Ile Lys Pro Cys Pro Pro Cys Lys Cys Pro Ala Pro
Asn Leu Leu Gly Gly Pro Ser Val Phe Ile Phe Pro Pro Lys Ile
Lys Asp Val Leu Met Ile Ser Leu Ser Pro Ile Val Thr Cys Val
Val Val Asp Val Ser Glu Asp Asp Pro Asp Val Gln Ile Ser Trp
Phe Val Asn Asn Val Glu Val His Thr Ala Gln Thr Gln Thr His
Arg Glu Asp Tyr Asn Ser Thr Leu Arg Val Val Ser Ala Leu
Pro Ile Gln His Gln Asp Trp Met Ser Gly Lys Glu Phe Lys
Cys Lys Val Asn Asn Lys Asp Leu Pro Ala Pro Ile Glu Arg Thr
Ile Ser Lys Pro Lys Gly Ser Val Arg Ala Pro Gln Val Tyr Val
Leu Pro Pro Pro Glu Glu Glu Met Thr Lys Lys Gln Val Thr
Leu Thr Cys Met Val Thr Asp Phe Met Pro Glu Asp Ile Tyr
Val Glu Trp Thr Asn Asn Gly Lys Thr Glu Leu Asn Tyr Lys
Asn Thr Glu Pro Val Leu Asp Ser Asp Gly Ser Tyr Phe Met
Tyr Ser Lys Leu Arg Val Glu Lys Lys Asn Trp Val Glu Arg
Asn Ser Tyr Ser Cys Ser Val Val His Glu Gly Leu His Asn His
His Thr Thr Lys Ser Phe Ser Arg Thr Pro Gly Lys
---

The compounds of the present invention represent recombinant monoclonal antibody KS1/4 and the heretofore unknown amino acid and nucleotide sequences of KS1/4. Due to the complementary nature of DNA base pairing, the sequence of one strand of a double-stranded DNA molecule is sufficient to determine the sequence of the opposing strand. The nucleotide sequence of the light chain of KS1/4 is:

```
CAA ATT CTT CTC ACC CAG TCT CCA GCA ATC ATG TCT GCA TCT
CCA GGG GAG AAG GTC ACC ATG ACC TGC AGT GCC AGC TCA AGT GTA
AGT TAC ATG CTC TGG TAC CAG CAG AAG CCA GGA TCC TCG CCC AAA
CCC TGG ATT TTT GAC ACA TCC AAC CTG GCT TCT GGA TTC CCT GCT
CGC TTC AGT GGC AGT GGG TCT GGG ACC TCT TAC TCT CTC ATA ATC
AGC AGC ATG GAG GCT GAA GAT GCT GCC ACT TAT TAC TGC CAT CAG
CGG AGT GGT TAC CCG TAC ACG TTC GGA GGG GGG ACC AAG CTG GAA
ATA AAA CGG GCT GAT GCT GCA CCA ACT GTA TCC ATC TTC CCA CCA
TCC AGT GAG CAG TTA ACA TCT GGA GGT GCC TCA GTC GTG TGC TTC
TTG AAC AAC TTC TAC CCC AAA GAC ATC AAT GTC AAG TGG AAG ATT
GAT GGC AGT GAA CGA CAA AAT GGC GTC CTG AAC AGT TGG ACT GAT
CAG GAC AGC AAA GAC AGC ACC TAC AGC ATG AGC AGC ACC CTC ACG
TTG ACC AAG GAC GAG TAT GAA CGA CAT AAC AGC TAT ACC TGT GAG
GCC ACT CAC AAG ACA TCA ACT TCA CCC ATT GTC AAG AGC TTC AAC
AGG AAT GAG TGT
``` while the nucleotide sequence of the heavy chain of KS1/4 is:

```
CAG ATC CAG TTG GTG CAG TCT GGA CCT GAG CTG AAG
AAG CCT GGA GAG ACA GTC AAG ATC TCC TGC AAG GCT TCT GGG TAT
ACC TTC ACA AAC TAT GGA ATG AAC TGG GTG AAG CAG ACT CCA GGA
AAG GGT TTA AAG TGG ATG GGC TGG ATA AAC ACC TAC ACT GGA GAA
CCA ACA TAT GCT GAT GAC TTC AAG GGA CGG TTT GCC TTC TCT TTG
GAA ACC TCT GCC AGC ACT GCC TTT TTG CAG ATT CAA CAA CCT CAG
AAT ATG AGG ACT ATG GCT ACA TAT TTC TGT GTA AGA TTT ATT TCT
AAG GGG GAC TAC TGG GGT CAA GGA ACG TCA GTC ACC GTC TCC TCA
GCC AAA ACA ACA GCC CCA TCG GTC TAT CCA CTG GCC CCT GTG TGT
GGA GAT ACA ACT GGC TCC TCG GTG ACT CTA GGA TGC CTG GTC AAG
GGT TAT TTC CCT GAG CCA GTG ACC TTG ACC TGG AAC TCT GGA TCC
CTG TCC AGT GGT GTG CAC ACC TTC CCA GCT GTC CTG CAG TCT GAC
CTC TAC ACC CTC AGC AGC TCA GTG ACT GTA ACC TCG AGC ACC TGG
CCC AGC CAG TCC ATC ACC TGC AAT GTG GCC CAC CCG GCA AGC AGC
ACC AAG GTG GAC AAG AAA ATT GAG CCC AGA GGG CCC ACA ATC AAG
CCC TGT CCT CCA TGC AAA TGC CCA GCA CCT AAC CTC TTG GGT GGA
CCA TCC GTC TTC ATC TTC CCT CCA AAG ATC AAG GAT GTA CTC ATG
ATC TCC CTG AGC CCC ATA GTC ACA TGT GTG GTG GTG GAT GTG AGC
GAG GAT GAC CCA GAT GTC CAG ATC AGC TGG TTT GTG AAC AAC GTG
GAA GTA CAC ACA GCT CAG ACA CAA ACC CAT AGA GAG GAT TAC AAC
AGT ACT CTC CGG GTG GTC AGT GCC CTC CCC ATC CAG CAC CAG GAC
TGG ATG AGT GGC AAG GAG TTC AAA TGC AAG GTC AAC AAC AAA GAC
CTC CCA GCG CCC ATC GAG AGA ACC ATC TCA AAA CCC AAA GGG TCA
GTA AGA GCT CCA CAG GTA TAT GTC TTG CCT CCA CCA GAA GAA GAG
ATG ACT AAG AAA CAG GTC ACT CTG ACC TGC ATG GTC ACA GAC TTC
ATG CCT GAA GAC ATT TAC GTG GAG TGG ACC AAC AAC GGG AAA ACA
GAG CTA AAC TAC AAG AAC ACT GAA CCA GTC CTG GAC TCT GAT GGT
TCT TAC TTC ATG TAC AGC AAG CTG AGA GTG GAA AAG AAG AAC TGG
GTG GAA AGA AAT AGC TAC TCC TGT TCA GTG GTC CAC GAG GGT CTG
CAC AAT CAC CAC ACG ACT AAG AGC TTC TCC CGG ACT CCG GGT AAA
```

The present invention further comprises a recombinant DNA compound which comprises DNA encoding a chimeric antibody light chain comprising an antigen-specific variable region derived from a first mammalian species and a constant region derived from a second and different mammalian species, said light chain variable region having an amino acid sequence substantially the same as:

```
Gln Ile Leu Leu Thr Gln Ser Pro Ala Ile Met Ser Ala Ser
Pro Gly Glu Lys Val Thr Met Thr Cys Ser Ala Ser Ser Ser Val
Ser Tyr Met Leu Trp Tyr Gln Gln Lys Pro Gly Ser Ser Pro Lys
Pro Trp Ile Phe Asp Thr Ser Asn Leu Ala Ser Gly Phe Pro Ala
Arg Phe Ser Gly Ser Gly Ser Gly Thr Ser Tyr Ser Leu Ile Ile
Ser Ser Met Glu Ala Glu Asp Ala Ala Thr Tyr Tyr Cys His Gln
Arg Ser Gly Tyr Pro Tyr Thr Phe Gly Gly Gly Thr Lys Leu
Glu Ile Lys Arg
```

The nucleotide sequence of the light chain variable region is:

```
CAA ATT CTT CTC ACC CAG TCT CCA GCA ATC ATG TCT GCA TCT
CCA GGG GAG AAG GTC ACC ATG ACC TGC AGT GCC AGC TCA AGT GTA
AGT TAC ATG CTC TGG TAC CAG CAG AAG CCA GGA TCC TCG CCC AAA
CCC TGG ATT TTT GAC ACA TCC AAC CTG GCT TCT GGA TTC CCT GCT
CGC TTC AGT GGC AGT GGG TCT GGG ACC TCT TAC TCT CTC ATA ATC
AGC AGC ATG GAG GCT GAA GAT GCT GCC ACT TAT TAC TGC CAT CAG
CGG AGT GGT TAC CCG TAC ACG TTC GGA GGG GGG ACC AAG CTG GAA
ATA AAA CGT
```

In addition, the invention comprises derivatives of the light chain variable region disclosed above, one such derivative having an amino acid residue sequence substantially the same as:

```
Gln Ile Leu Leu Thr Gln Ser Pro Ala Ile Met Ser Ala Ser
Pro Gly Glu Lys Val Thr Met Thr Cys Ser Ala Ser Ser Ser Val
Ser Tyr Met Leu Trp Tyr Gln Gln Lys Pro Gly Ser Ser Pro Lys
```

-continued

Pro Trp Ile Phe Asp Thr Ser Asn Leu Ala Ser Gly Phe Pro Ala
Arg Phe Ser Gly Ser Gly Ser Gly Thr Ser Tyr Ser Leu Ile Ile
Ser Ser Met Glu Ala Glu Asp Ala Ala Thr Tyr Tyr Cys His Gln
Arg Ser Gly Tyr Pro Tyr Thr Phe Gly Gly Gly Thr Lys Leu
Glu Ile Lys Gly

The nucleotide sequence of this light chain variable region derivative is:

CAA ATT CTT CTC ACC CAG TCT CCA GCA ATC ATG TCT GCA TCT
CCA GGG GAG AAG GTC ACC ATG ACC TGC AGT GCC AGC TCA AGT GTA
AGT TAC ATG CTC TGG TAC CAG CAG AAG CCA GGA TCC TCG CCC AAA
CCC TGG ATT TTT GAC ACA TCC AAC CTG GCT TCT GGA TTC CCT GCT
CGC TTC AGT GGC AGT GGG TCT GGG ACC TCT TAC TCT CTC ATA ATC
AGC AGC ATG GAG GCT GAA GAT GCT GCC ACT TAT TAC TGC CAT CAG
CGG AGT GGT TAC CCG TAC ACG TTC GGA GGG GGG ACC AAG CTG GAA
ATA AAA GGT

Furthermore, the invention also comprises a recombinant DNA compound which comprises DNA encoding a chimeric antibody heavy chain variable region derived from a first mammalian species and a constant region derived from a second and different mammalian species, said heavy chain variable region having an amino acid sequence substantially the same as:

Gln Ile Gln Leu Val Gln Ser Gly Pro Glu Leu Lys
Lys Pro Gly Glu Thr Val Lys Ile Ser Cys Lys Ala Ser Gly Tyr
Thr Phe Thr Asn Tyr Gly Met Asn Trp Val Lys Gln Thr Pro
Gly Lys Gly Leu Lys Trp Met Gly Trp Ile Asn Thr Tyr Thr Gly
Glu Pro Thr Tyr Ala Asp Asp Phe Lys Gly Arg Phe Ala Phe
Ser Leu Glu Thr Ser Ala Ser Thr Ala Phe Leu Gln Ile Gln Gln
Pro Gln Asn Met Arg Thr Met Ala Thr Tyr Phe Cys Val Arg
Phe Ile Ser Lys Gly Asp Tyr Trp Gly Gln Gly Thr Ser Val Thr
Val Ser Ser

The nucleotide sequence of this heavy chain variable region is:

CAG ATC CAG TTG GTG CAG TCT GGA CCT GAG CTG AAG
AAG CCT GGA GAG ACA GTC AAG ATC TCC TGC AAG GCT TCT GGG TAT
ACC TTC ACA AAC TAT GGA ATG AAC TGG GTG AAG CAG ACT CCA GGA
AAG GGT TTA AAG TGG ATG GGC TGG ATA AAC ACC TAC ACT GGA GAA
CCA ACA TAT GCT GAT GAC TTC AAG GAA CGG TTT GCC TTC TCT TTG
GAA ACC TCT GCC AGC ACT GCC TTT TTG CAG ATT CAA CAA CCT CAG
AAT ATG AGG ACT ATG GCT ACA TAT TTC TGT GTA AGA TTT ATT TCT
AAG GGG GAC TAC TGG GGT CAA GGA ACG TCA GTC ACC GTC TCC TCA

Both the light chain and heavy chain molecules of the present invention are associated with distinct signal peptides. The amino acid residue sequence of the light chain signal peptide is substantially the same as:

Met Asp Phe Gln Val Gln Ile Phe Ser Phe Leu Leu Ile
Ser Ala Ser Val Ile Met Ser Arg Gly

The nucleotide sequence of this signal peptide is:

ATG GAT TTT CAA GTG CAG ATT TTT AGC TTC CTG CTA ATC
AGT GCT TCA GTC ATA ATG TCC AGA GGA

The amino acid residue sequence of the heavy chain signal peptide is substantially the same as:

Met Asp Trp Leu Trp Asn Leu Leu Phe Leu Met Ala Ala
Ala Gln Ser Ala Gln Ala

The nucleotide sequence of this signal peptide is:

ATG GAT TGG CTG TGG AAC TTG CTA TTC CTG ATG GCA GCT
GCC CAA AGT GCC CAA GCA

The novel DNA compounds of the present invention are derived from cDNA clones prepared from the mRNA from the hybridoma cell line which makes monoclonal antibody KS1/4. Plasmid pGKC2310 comprises the entire coding sequence of the light chain of monoclonal antibody KS1/4, the coding sequence of the signal peptide associated with the light chain, and the 5' and 3' untranslated regions of this molecule. The 5' untranslated region has the DNA sequence:

5'-TC TGA CAG ACA CTA CTG TGC CTC GTC GGT TGG GAC CTA AAA GGG
CTA GTA GAA TCC GCA AGC TTT TTA ATC TCT CCA AAG AAG ATG ATG
TCC GCC AGT ATG TTG TCA GGA AGC CCT TAA ACA AAG AAG GTA ATT
AGC TAG GGA CCA AAA TTC AAA GAC AAG-3' whereas the 3' untranslated region has the DNA sequence:

5'-TAG AGA CAA AGG TCC TGA GAC GCC ACC ACC AGC
TCC CCA GCT CCA TCC TAT CTT CCC TTC TAA GGT CTT GGA GGC TTC
CCC ACA AGC GAC ATA CCA CTG TTG CGG TGC TCC AAA CCT CCT CCC

```
CAC CTC CTT CTC CTC CTC CTC CCT TTC CTT GGC TTT TAT CAT GCT
AAT ATT TGC AGA AAA TAT TCA ATA AAG TGA GTC TTT GCA CTT G-3'
```

Figure 12:
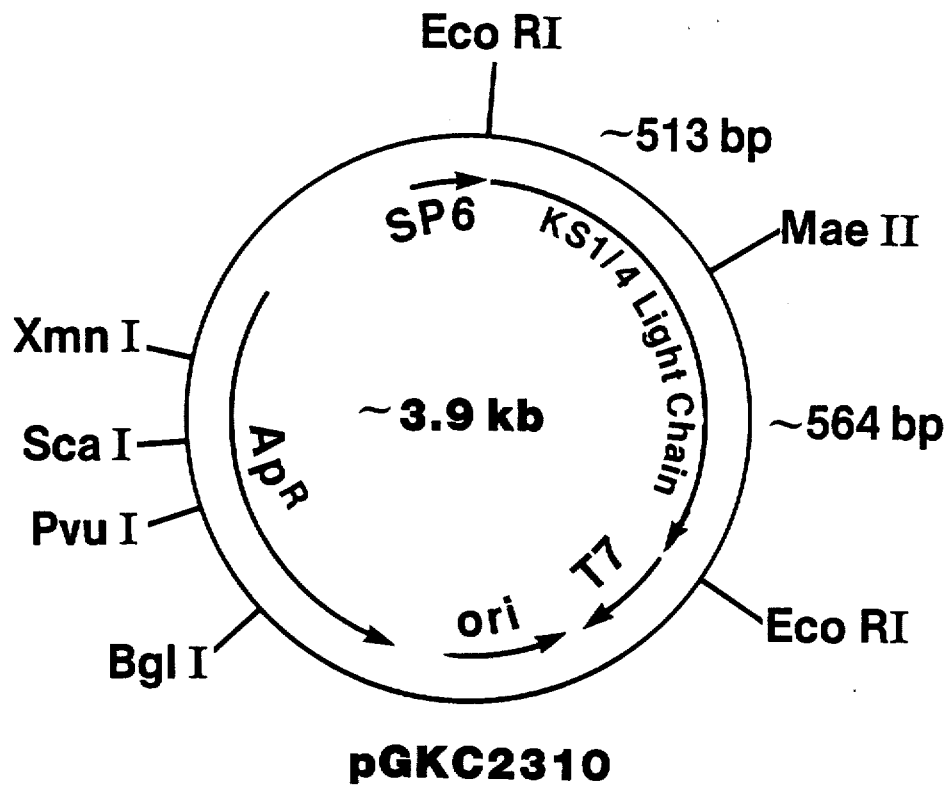
FIG. 12—the restriction site and function maps of plasmids pGKC2310 and pG2A52.
Figure 12:
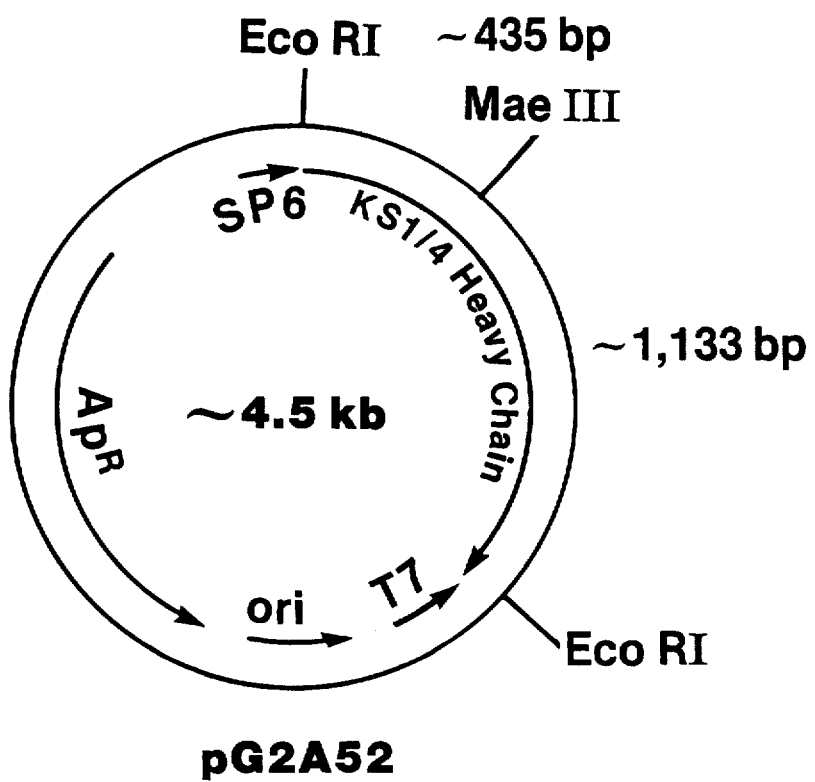

Plasmid pGKC2310 can be conventionally isolated from *E. coli* K12 MM294/pGKC2310, a strain deposited and made part of the permanent stock culture collection of the Northern Regional Research Laboratory (NRRL), Peoria, Ill. A culture of *E. coli* K12 MM294/pKC2310 can be obtained from the NRRL under the accession number B-18356. A restriction site and function map of plasmid pKC2310 is presented in FIG. 12 of the accompanying drawings.

Plasmid pG2A52 comprises the entire coding sequence of the heavy chain of monoclonal antibody KS1/4, the coding sequence of the signal peptide associated with the heavy chain, and the 5' and 3' untranslated regions of this molecule. The heavy chain encoded by this molecule is of the IgG2A subclass. The 5' untranslated region has the DNA sequence:

```
5'-TCG TTT GTC TTA AGG CAC CAC TGA GCC CAA GTC TTA GAC ATC-3'
``` whereas the 3' untranslated region has the DNA sequence:

```
5'-TGA GCT CAG CAC CCA CAA AAC TCT CAG GTC CAA AGA GAC ACC CAC
ACT CAT CTC CAT GCT TCC CTT GTA TAA ATA AAG CAC CCA GCA ATG
CCT GGG ACC ATG TAA AAA AAA AAA AAA AAA AGA GG-3'
```

Plasmid pG2A52 can be conventionally isolated from *E. coli* K12 MM294/pG2A52, also deposited and made part of the permanent stock culture collection of the NRRL. A culture of *E. coli* K12 MM294/pG2A52 can be obtained from the NRRL under the accession number NRRL B-18357. A restriction site and function map of plasmid pG2A52 is presented in FIG. 12 of the accompanying drawings.

Figure 13:
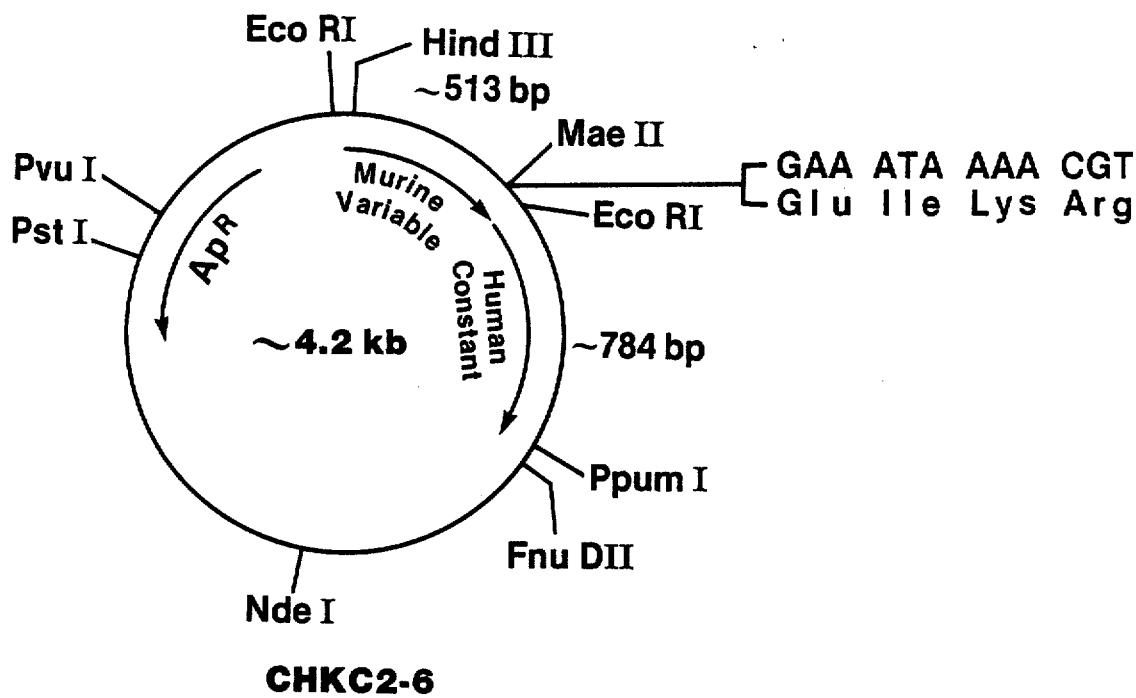
FIG. 13—the restriction site and function maps of plasmids CHKC2-6 and CHKC2-18.
Figure 13:
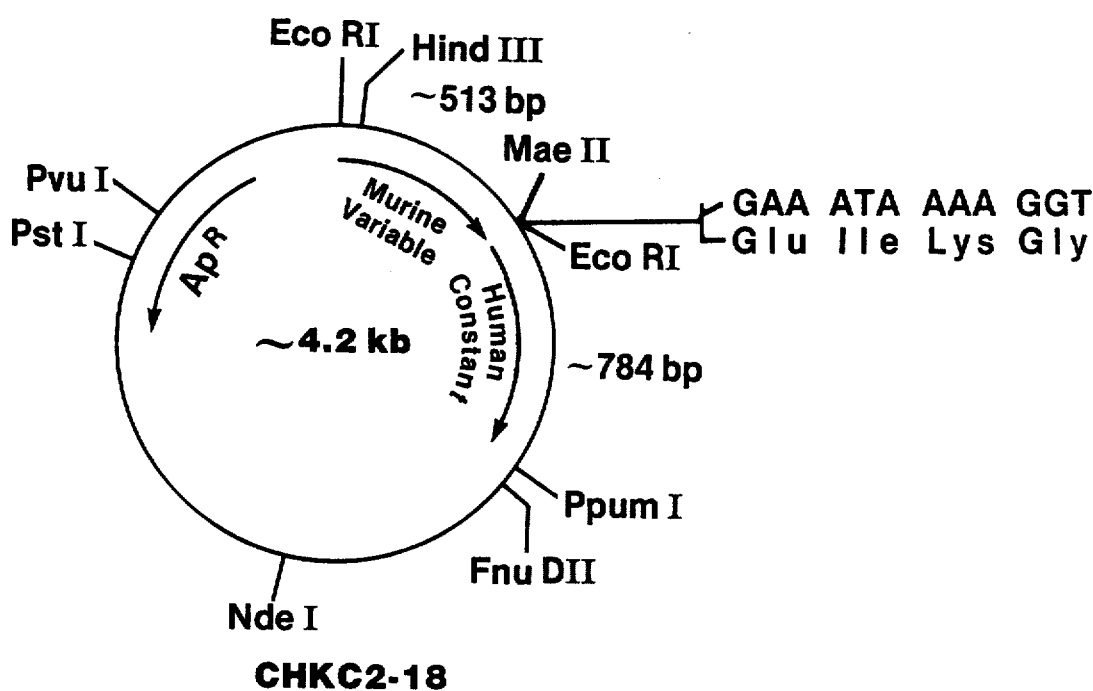

Plasmid CHKC2-6 comprises the cDNA coding sequence of the natural light chain variable region of monoclonal antibody KS1/4, the cDNA coding sequence of the signal peptide associated with the light chain, and a genomic DNA sequence which encodes the light chain constant region of a human immunoglobulin. Plasmid CHKC2-6 can be conventionally isolated from *E. coli* K12 DH5/CHKC2-6, also deposited and made part of the permanent stock culture collection of the NRRL. A culture of *E. coli* K12 DH5/CHKC2-6 can be obtained from the NRRL under the accession number NRRL B-18358. A restriction site and function map of plasmid CHKC2-6 is presented in FIG. 13 of the accompanying drawings.

Plasmid CHKC2-18 comprises the cDNA coding sequence of a derivative light chain variable region of monoclonal antibody KS1/4, the cDNA coding sequence of the signal peptide associated with the light chain, and a genomic DNA sequence which encodes the light chain constant region of a human immunoglobulin. The variation in this sequence comprises the alteration of the codon at the 3' terminus. The natural light chain variable region contains an arginine codon at the 3' terminus, whereas the codon in the same position in plasmid CHKC2-18 encodes a glycine residue. Plasmid CHKC2-18 can be conventionally isolated from *E. coli* K12 DH5/CHKC2-18, also deposited and made part of the permanent stock culture collection of the NRRL. A culture of *E. coli* K12 DH5/CHKC2-18 can be obtained from the NRRL under the accession number NRRL B-18359. A restriction site and function map of plasmid CHKC2-18 is presented in FIG. 13 of the accompanying drawings.

Figure 14:
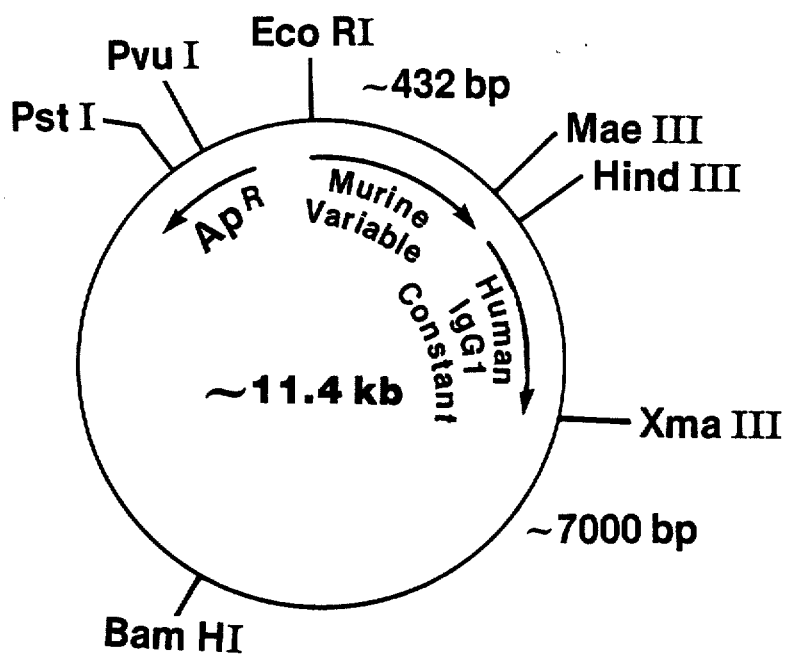
FIG. 14—the restriction site and function maps of plasmids CH2A5 and CH2A5IG2.
Figure 14:
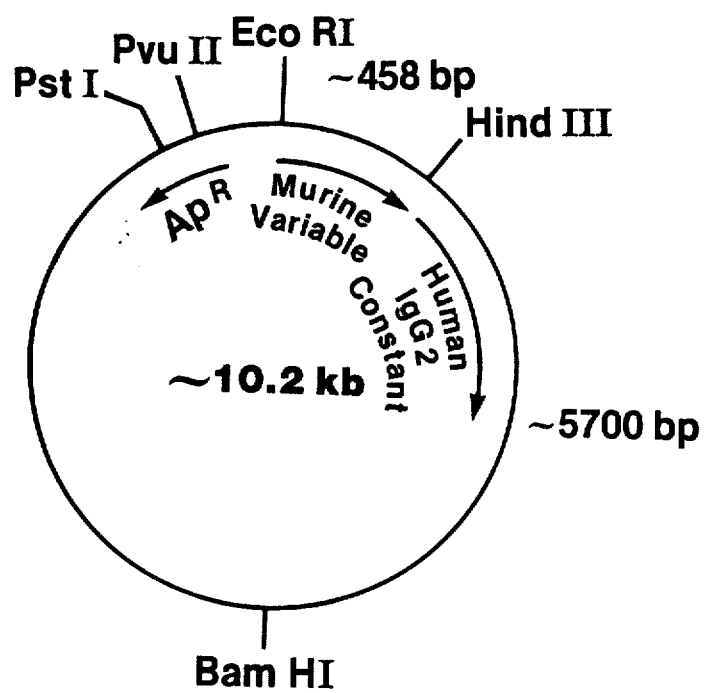

Plasmid CH2A5 comprises the cDNA coding sequence of the heavy chain variable region of monoclonal antibody KS1/4, the cDNA coding sequence of the signal peptide associated with said heavy chain, and a genomic DNA sequence which encodes the heavy chain constant region of human immunoglobulin IgG1. Plasmid CH2A5 can be conventionally isolated from *E. coli* K12 MM294/CH2A5, also deposited and made part of the permanent stock culture collection of the NRRL. A culture of *E. coli* K12 MM294/CH2A5 can be obtained from the NRRL under the accession number NRRL B-18360. A restriction site and function map of plasmid CH2A5 is presented in FIG. 14 of the accompanying drawings.

Plasmid CH2A5IG2 comprises the cDNA coding sequence of the heavy chain variable region of monoclonal antibody KS1/4, the cDNA coding sequence of the signal peptide associated with the heavy chain and a genomic DNA sequence which encodes the heavy chain constant region of human immunoglobulin IgG2. Plasmid CH2A5IG2 can be conventionally isolated from *E. coli* K12 DH5/CH2A5IG2, also deposited and made part of the permanent stock culture collection of the NRRL. A culture of *E. coli* K12 DH5/CH2A5IG2 can be obtained from the NRRL under the accession number NRRL B-18361. A restriction site and function map of plasmid CH2A5IG2 is presented in FIG. 14 of the accompanying drawings.

Figure 15:
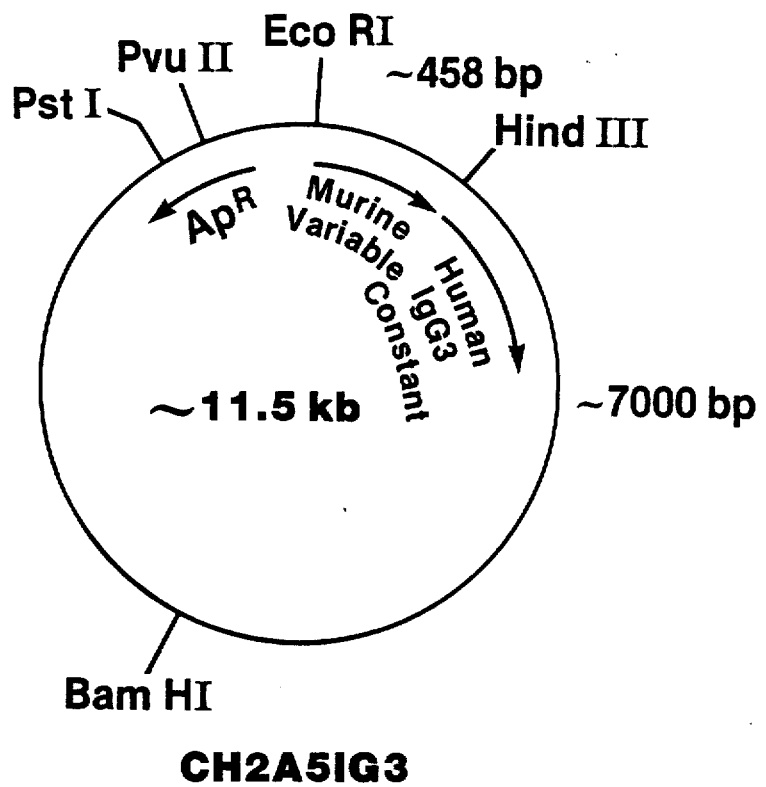
FIG. 15—the restriction site and function maps of plasmids CH2A5IG3 and CH2A5IG4.
Figure 15:
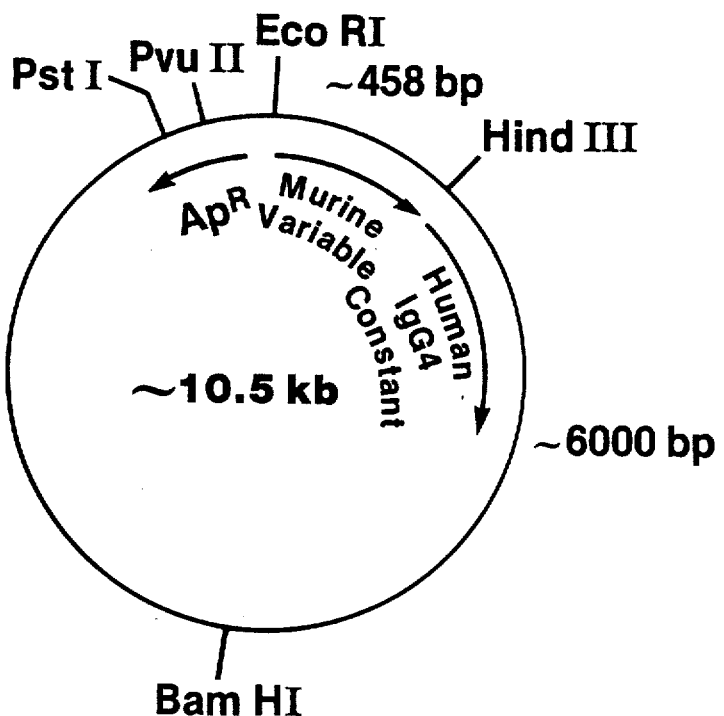

Plasmid CH2A5IG3 comprises the cDNA coding sequence of the heavy chain variable region of monoclonal antibody KS1/4, the cDNA coding sequence of the signal peptide associated with the heavy chain and a genomic DNA sequence which encodes the heavy chain constant region of human immunoglobulin IgG3. Plasmid CH2A5IG3 can be conventionally isolated from *E. coli* K12 DH5/CH2A5IG3, also deposited and made part of the permanent stock culture collection of the NRRL. A culture of *E. coli* K12 DH5/CH2A5IG3 can be obtained from the NRRL under the accession number NRRL B-18362. A restriction site and function map of plasmid CH2A5IG3 is presented in FIG. 15 of the accompanying drawings.

Plasmid CH2A5IG4 comprises the cDNA coding sequence of the heavy chain variable region of monoclonal antibody KS1/4, the cDNA coding sequence of the signal peptide associated with the heavy chain and a genomic DNA sequence which encodes the heavy chain constant region of human immunoglobulin IgG4.

Plasmid CH2A5IG4 can be conventionally isolated from *E. coli* K12 DH5/CH2A5IG4, also deposited and made part of the permanent stock culture collection of the NRRL. A culture of *E. coli* K12 DH5/CH2A5IG4 can be obtained from the NRRL under the accession number NRRL B-18363. A restriction site and function map of plasmid CH2A5IG4 is presented in FIG. 15 of the accompanying drawings.

The present DNA compounds which encode recombinant KS1/4 and derivatives are especially preferred for the construction of vectors for transformation and expression of the various antibody chains in mammalian and other eukaryotic cells. Many mammalian host cells possess the necessary cellular machinery for the recognition and proper processing of the signal peptides present on the amino-terminus of the various antibody chains embodied in the present invention. Some mammalian host cells also provide the post-translational modifications, such as glycosylation, that are observed in antibody molecules. A wide variety of vectors exist for the transformation of eukaryotic host cells, and the specific vectors exemplified below are in no way intended to limit the scope of the present invention.

Figure 11:
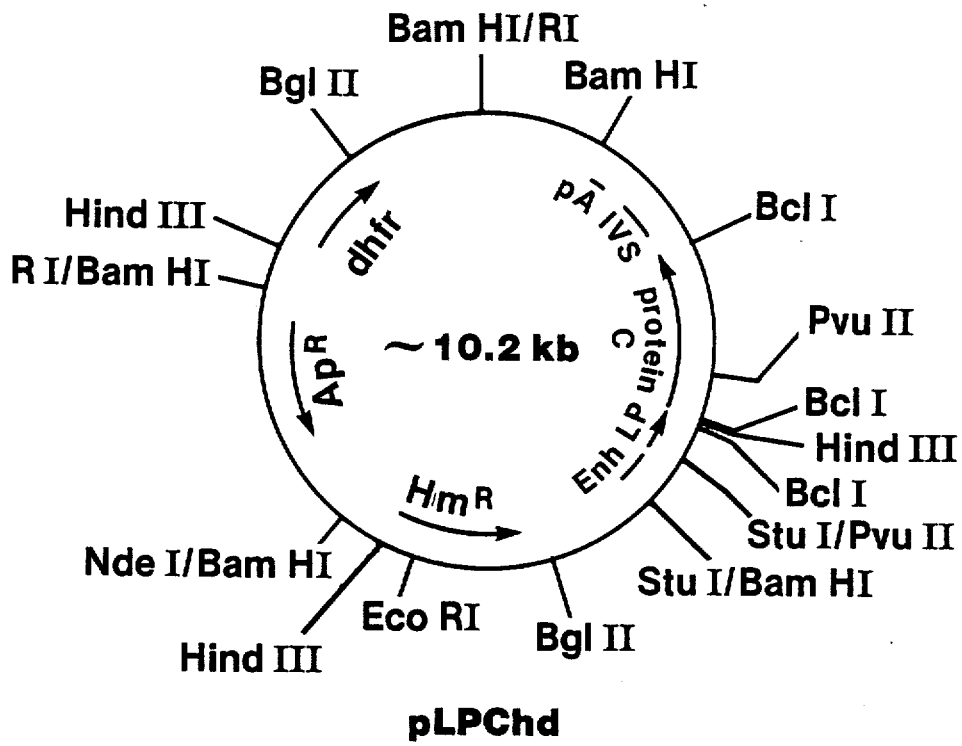
FIG. 11—the restriction site and function maps of plasmids pLPChd and phd.
Figure 11:
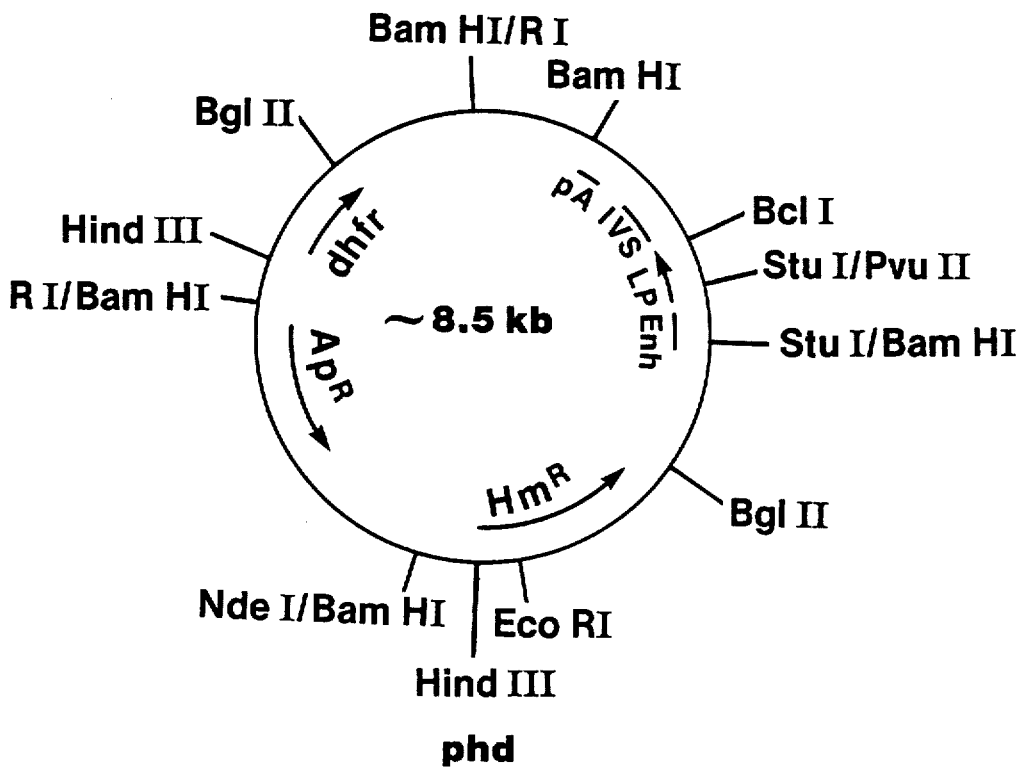

The expression vectors of the present invention which drive the production of recombinant KS1/4 and the chimeric derivatives thereof were all constructed using plasmid phd. Plasmid phd was constructed from a wide variety of publicly available starting materials. A restriction site and function map of plasmid phd is presented in FIG. 11 of the accompanying drawings.

Plasmid phd was constructed by first isolating plasmid pKC283 from *E. coli* K12 BE1201/pKC283. This culture may be obtained from the NRRL under accession number NRRL B-15830. Plasmid pKC283 comprises a hybrid lpp-pL promoter of bacteriophage λ. This plasmid is obtained from *E. coli* K12 BE1201 cells because these cells comprise a temperature sensitive cI repressor integrated into the cellular DNA. The unneeded lacZ portion of plasmid pKC283 was excised by first digesting the plasmid with restriction enzyme PvuII. Specific DNA linkers were then added to the digested DNA to convert the PvuII sites into a single XhoI site, which created plasmid pKC283PX. Detailed descriptions of the isolation of plasmids pKC283 and pKC283PX are presented respectively in Examples 1 and 2. Restriction site and function maps of plasmids pKC283 and pKC283PX are presented in FIG. 1 of the accompanying drawings. As explained in Example 3, plasmid pKC283PX is transformed into *E. coli* K12 MO(λ+) *E. coli* K12 MO(λ+) is available from the NRRL under the accession number NRRL B-15993.

Plasmid pKC283PX was next digested with restriction enzymes BglII and XhoI. After the vector was purified, DNA linkers with BglII and XhoI ends were ligated into the vector to form plasmid pKC283-L. The BglII-XhoI linker also contained an XbaI site. The XhoI site of plasmid pKC283-L was next converted into a BamHI site. This was accomplished by a total digestion of plasmid pKC283-L with restriction enzyme XhoI, followed by treatment with Klenow, then addition of BamHI linkers, to form plasmid pKC283-LB. Detailed descriptions of the construction of plasmids pKC283-L and pKC283-LB are presented respectively in Examples 4 and 5. Restriction site and function maps of plasmids pKC283-L and pKC283-LB are presented in FIG. 1 of the accompanying drawings The extraneous *E. coli* DNA was next excised from plasmid pKC283PX by total digestion with restriction enzyme SalI, followed by treatment of the ~4.0 kb vector with Klenow, then addition of EcoRI linkers. Upon recircularization via ligation, this formed plasmid pKC283PRS. Plasmid pKC283PRS was then digested with restriction enzymes PstI and SphI and the ~0.85 kb PstI-SphI restriction fragment was isolated. In an analogous manner, plasmid pKC283-LB was digested with restriction enzymes PstI and SphI and the ~3.0 kb fragment was isolated. The ~0.85 kb PstI-SphI fragment L. of pKC283PRS was then ligated into the ~3.0 kb PstISphI vector fragment of pKC283-LB to form plasmid pL32. Detailed descriptions of the construction of plasmids pKC283PRS and pL32 are presented in Example 6. Restriction site and function maps of plasmids pKC283PRS and pL32 are presented in FIG. 1 of the accompanying drawings.

Figure 2:
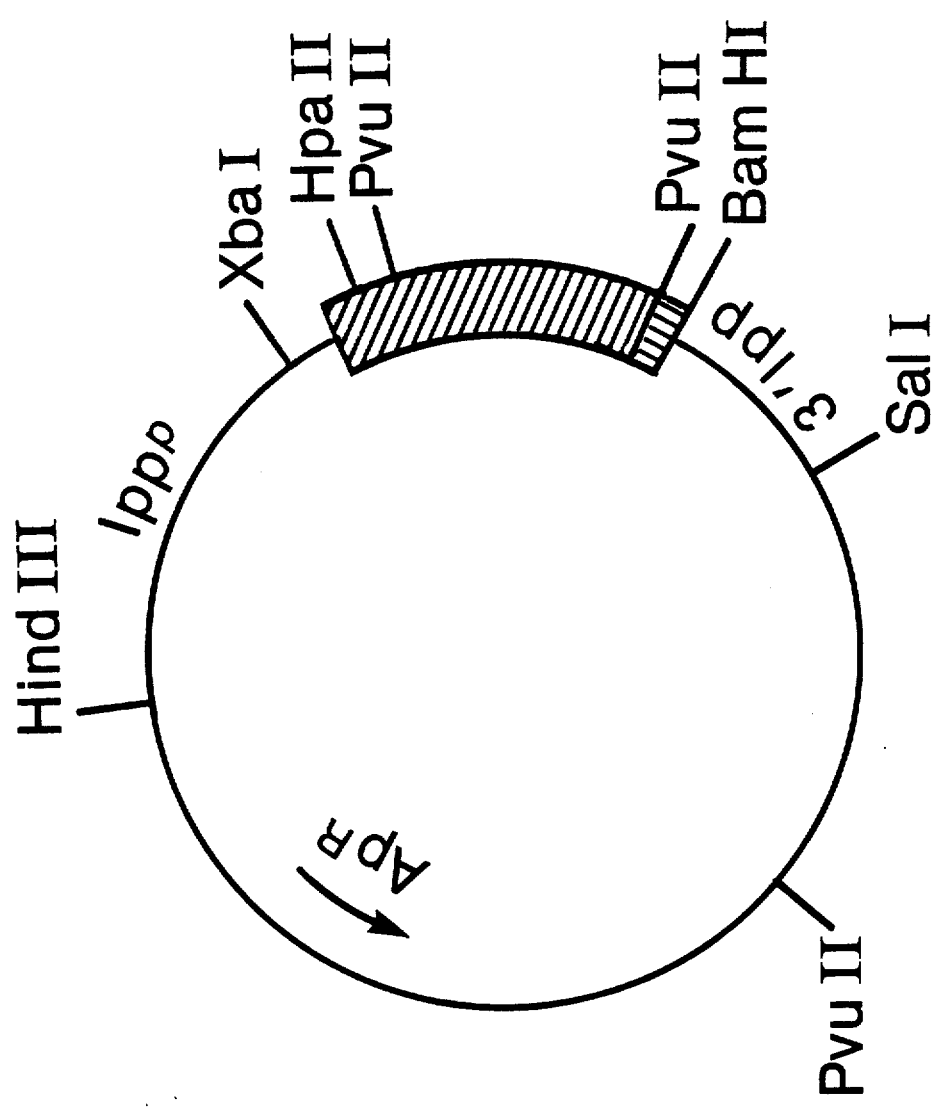
FIG. 2—the restriction site and function map of plasmid pNM789.
Figure 3:
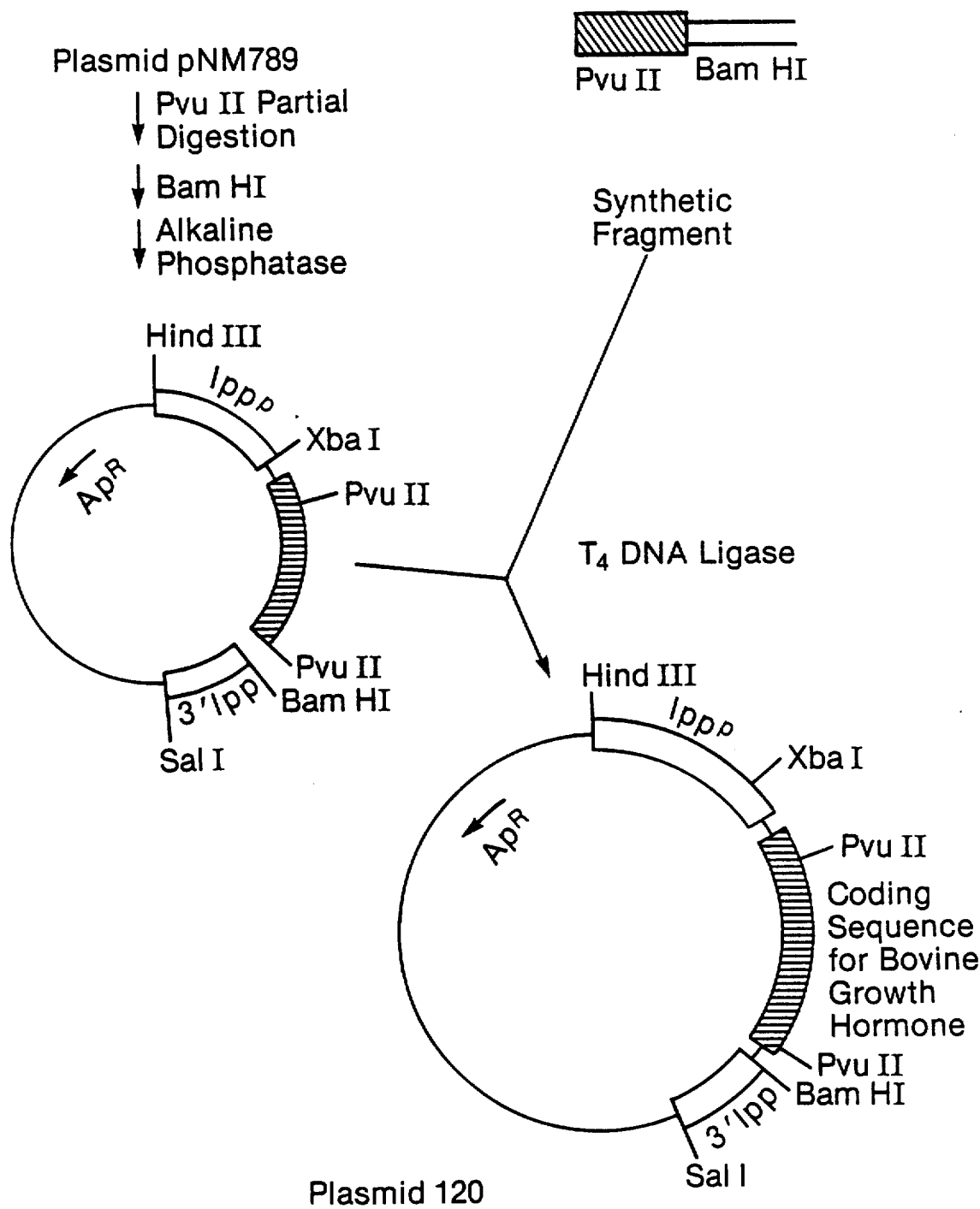
FIG. 3—a schematic showing the construction of plasmid 120.
Figure 4:
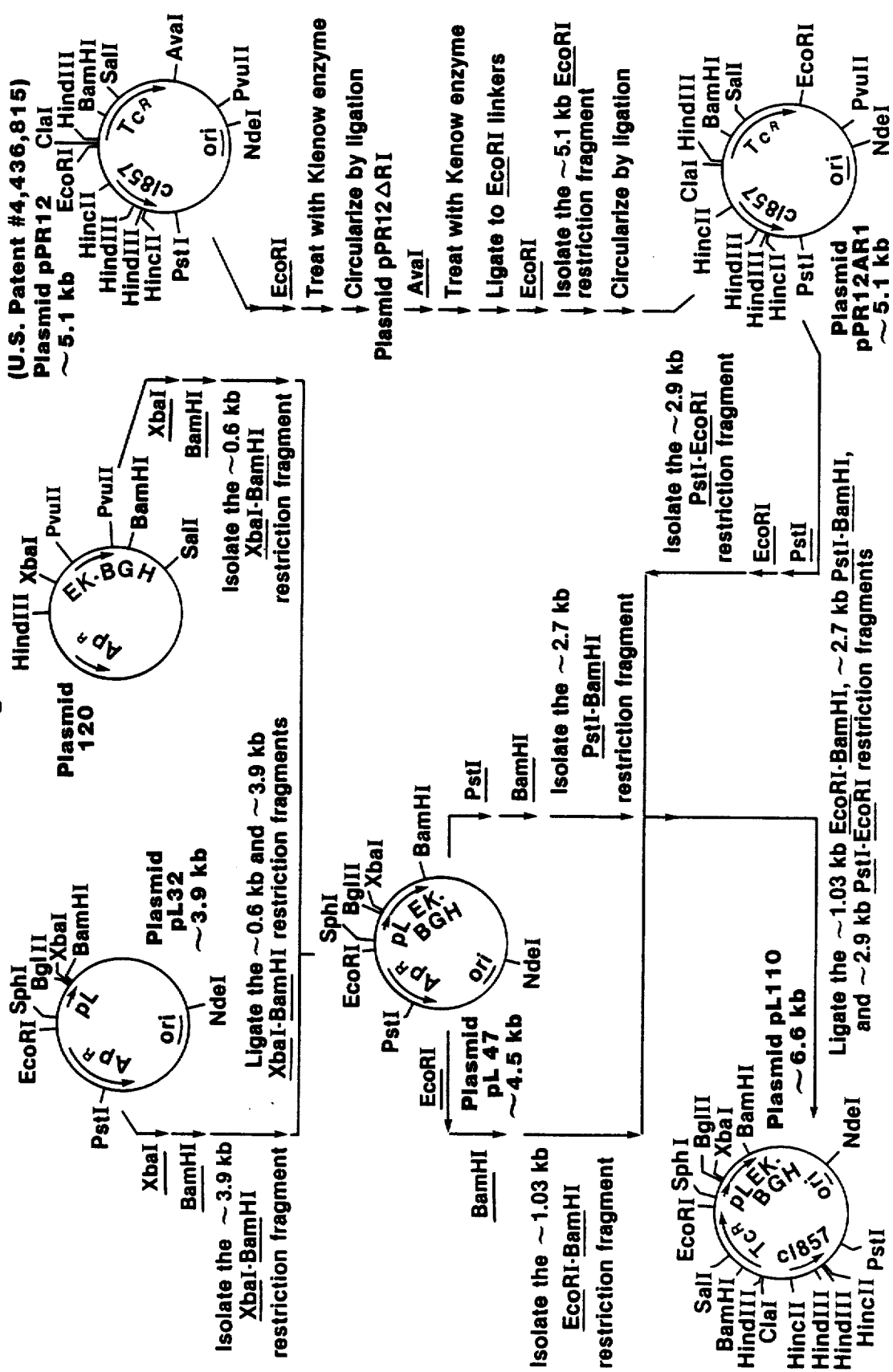
FIG. 4—a schematic showing the construction of plasmid pL110.

Next, plasmid pNM789 is obtained from the NRRL in *E. coli* K12 RV308/pNM789 under the accession number B-18216. A restriction site and function map of plasmid pNM789 is presented in FIG. 2 of the accompanying drawings. Plasmid pNM789 was partially digested with restriction enzyme PvuII, fully digested with restriction enzyme BamHI, then treated with alkaline phosphatase. Next, a new PvuII-BamHI linker was ligated into the digested, phosphatased vector pNM789 to form plasmid 120. Plasmid 120 was then totally digested with restriction enzymes XbaI and BamHI and the ~0.6 kb XbaI-BamHI EK-BGH-encoding restriction fragment was isolated. Plasmid pL32 was also digested with restriction enzymes XbaI and BamHI and the ~3.9 kb vector fragment was isolated. The ~0.6 kb XbaI-BamHI fragment of plasmid 120 was then ligated into the ~3.9 kb vector fragment of plasmid pL32 to form plasmid pL47. Detailed descriptions of the construction of plasmids 120 and pL47 are presented in Examples 6 and 7. Restriction site and function maps of plasmids 120 and pL47 are presented respectively in FIGS. 3 and 4 of the accompanying drawings.

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued 13 Mar., 1984. A restriction site and function map of plasmid pPR12 is presented in FIG. 4 of the accompanying drawings. The EcoRI site was removed from plasmid pPR12 by first totally digesting the plasmid with restriction enzyme EcoRI, followed by treatment with Klenow. The vector was then recircularized by ligation to form plasmid pBR12ΔR1. Plasmid pPR12-66 R1 was then digested with restriction enzyme AvaI and treated with Klenow. The AvaI-digested, Klenow treated pPR12ΔR1 was next ligated to EcoRI linkers, cut with restriction enzyme EcoRI, then recircularized to form plasmid pPR12AR1. A detailed description of the construction of plasmid pPR12AR1 is presented in Example 8. A restriction site and function map of plasmid pPR12AR1 is presented in FIG. 4 of the accompanying drawings.

The ~2.9 kb PstI-EcoRI restriction fragment of plasmid pPR12AR1 was isolated after the plasmid was first digested with restriction enzymes PstI and EcoRI Plasmid pL47 was digested with restriction enzymes PstI and BamHI and the ~2.7 kb PstI-BamHI restriction fragment was isolated. In a separate reaction, plasmid pL47 was digested with restriction enzymes EcoRI and BamHI and the ~1.03 kb EcoRI-BamHI fragment was isolated. The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to form plasmid pL110. A detailed description of the construction of plasmid pL110 is presented in Example 9. A restriction site and function map of plasmid pL110 is presented in FIG. 4 of the accompanying drawings.

The BK enhancer-type vector of the present invention comprises a BK enhancer-adenovirus late promoter cassette plus a hygromycin resistance conferring gene and a murine dihydrofolate reductase (dhfr) gene. The use of the BK virus enhancer in conjunction with the adenovirus late promoter significantly increases transcription of a recombinant gene in eukaryotic host cells. The hygromycin resistance-conferring gene is present as a selectable marker for use in eukaryotic host cells. The murine dihydrofolate reductase gene, under appropriate conditions, is amplified in the host chromosome. This amplification, described in a review by Schimke, 1984, Cell 37:705–713, can also involve DNA sequences closely contiguous with the dhfr gene. The dhfr gene is a selectable marker in dhfr-negative cells and can be used to increase the copy number of a DNA segment by exposing the host cell to increasing levels of methotrexate.

Figure 5:
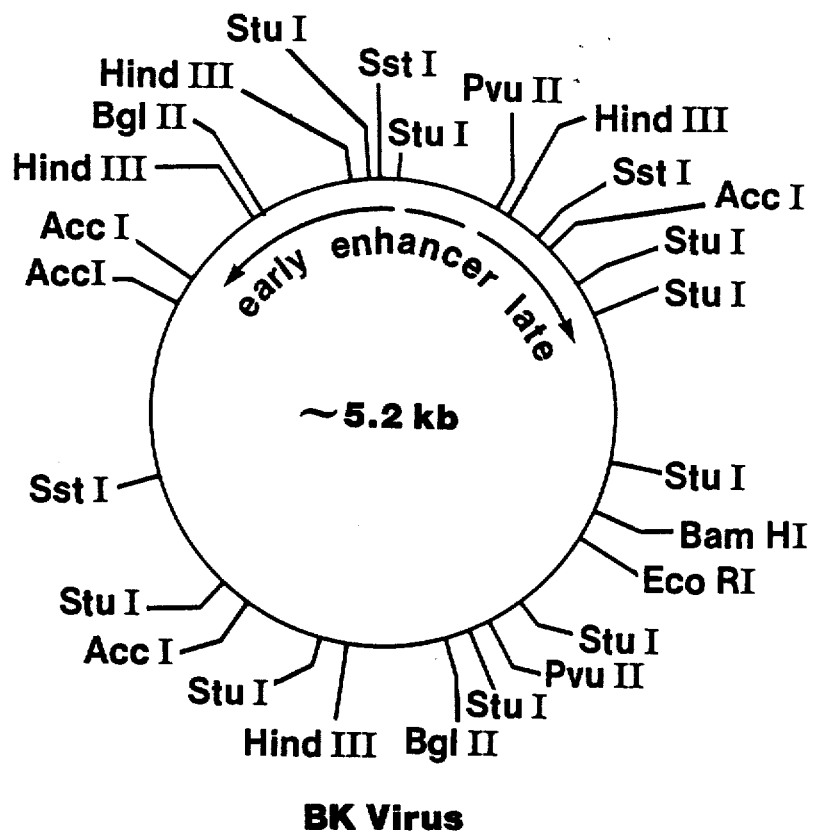
FIG. 5—the restriction site and function maps of the BK virus and plasmid pBKneo1.
Figure 5:
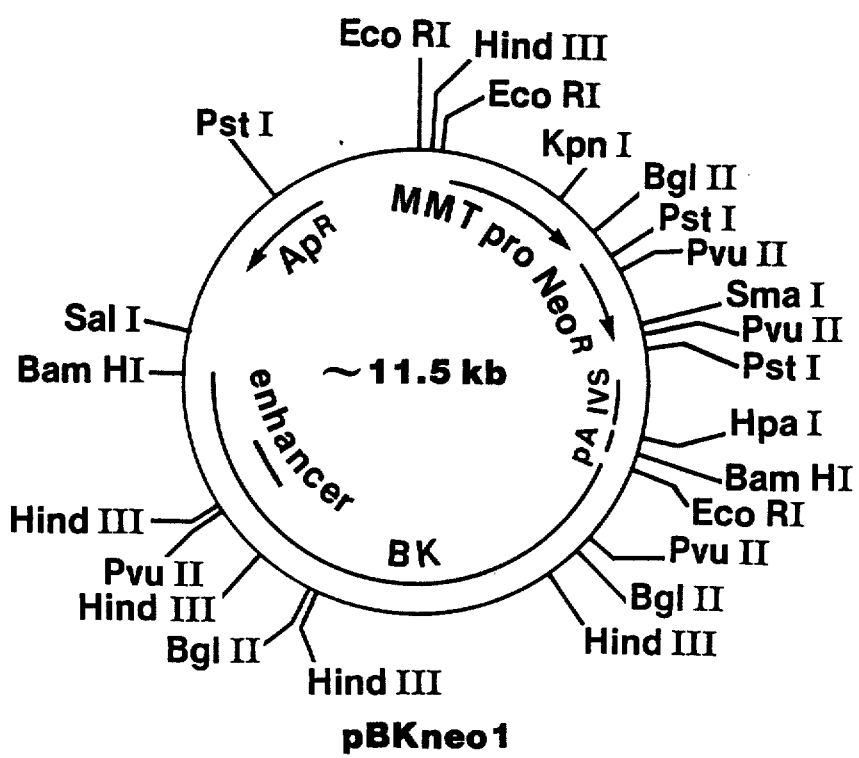

Plasmid pLPChd may be used to construct a eukaryotic expression vector for expression of the novel KS1/4 of the present invention. Plasmid pLPChd contains the dhfr gene, the Adenovirus type-2 promoter and the BK virus enhancer. The BK virus, which contains the BK virus enhancer, can be purchased or readily isolated in large quantities as described in Example 10. The BK virus is also available from the American Type Culture Collection under the accession number ATCC VR-837. A restriction site and function map of the BK virus is presented in FIG. 5 of the accompanying drawings.

The BK viral genome was combined with a portion of plasmid pdBPV-MMTneo to construct plasmids pBKneo1 and pBKneo2. Plasmid pdBPV-MMTneo, about 15 kb in size and available from the ATCC under the accession number ATCC 37224, comprises the replicon and β-lactamase gene from plasmid pBR322, the mouse metallothionein promoter positioned to drive expression of a structural gene that encodes a neomycin resistance-conferring enzyme, and about 8 kb of bovine papilloma virus (BPV) DNA. Plasmid pdBPV-MMTneo can be digested with restriction enzyme BamHI to generate two fragments: the ~8 kb fragment that comprises the BPV DNA and an ~7 kb fragment that comprises the other sequences described above. BK virus has only one BamHI restriction site, and plasmids pBKneo1 and pBKneo2 were constructed by ligating the ~7 kb BamHI restriction fragment of plasmid pdBPV-MMTneo to BamHI-linearized BK virus DNA. The construction of plasmids pBKneo1 and pBKneo2, which differ only with respect to the orientation of the BK virus DNA, is described in Example 11. Plasmid pBKneo1 contains an ~2.1 kb SalI-HindIII restriction fragment, whereas plasmid pBKneo2 contains an ~1.0 kb restriction fragment. A restriction site and function map of plasmid pBKneo1 is presented in FIG. 5 of the accompanying drawings.

Figure 6:
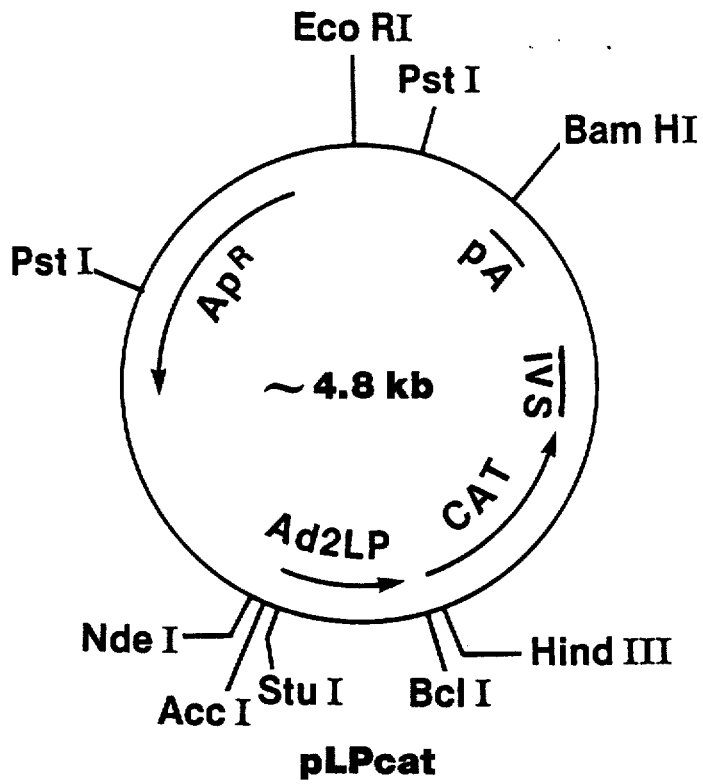
FIG. 6—the restriction site and function maps of plasmids pLPcat and pBLcat.
Figure 6:
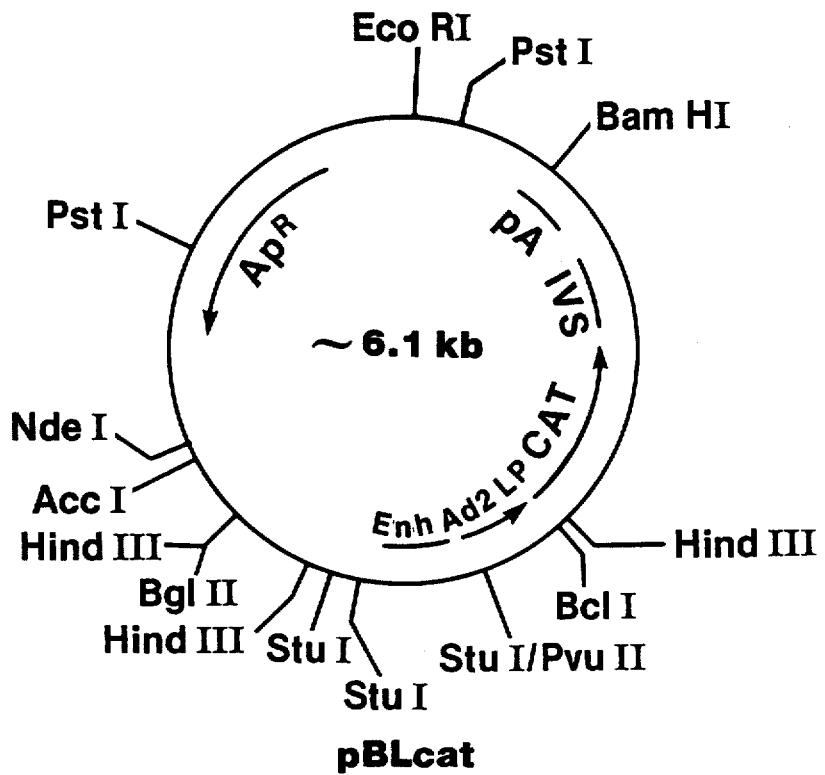

Plasmids pBKneo1 and pBKneo2 each comprise the entire genome of the BK virus, including the enhancer sequence, and thus serve as useful starting materials for the expression vector of the present invention. Expression vector, plasmid pBLcat, comprises the BK enhancer sequence in tandem with the human adenovirus-type-2 late promoter positioned to drive expression of the chloramphenicol acetyltransferase enzyme (CAT). Plasmid pSV2cat serves as a convenient source of the CAT gene and can be obtained from the ATCC under the accession number ATCC 37155. Human adenovirus-type-2 DNA is commercially available and can also be obtained from the ATCC under the accession number ATCC VR-2. Illustrative plasmid pBLcat was constructed by ligating the ~0.32 kb late-promoter-containing AccI-PvuII restriction fragment of human adenovirus-type-2 DNA to blunt-ended BclI linkers that attached only to the PvuII end of the AccI-PvuII restriction fragment. The resulting fragment was then ligated to the ~4.51 kb AccI-StuI restriction fragment of plasmid pSV2cat to yield intermediate plasmid pLPcat. The desired plasmid pBLcat was constructed from plasmid pLPcat by ligating the origin of replication and enhancer-containing ~1.28 kb AccI-PvuII restriction fragment of BK virus DNA to the ~4.81 kb AccI-StuI restriction fragment of plasmid pLPcat. The construction of plasmid pBLcat is further described in Example 12. Restriction site and function maps of plasmids pLPcat and pBLcat are presented in FIG. 6 of the accompanying drawings.

Figure 7:
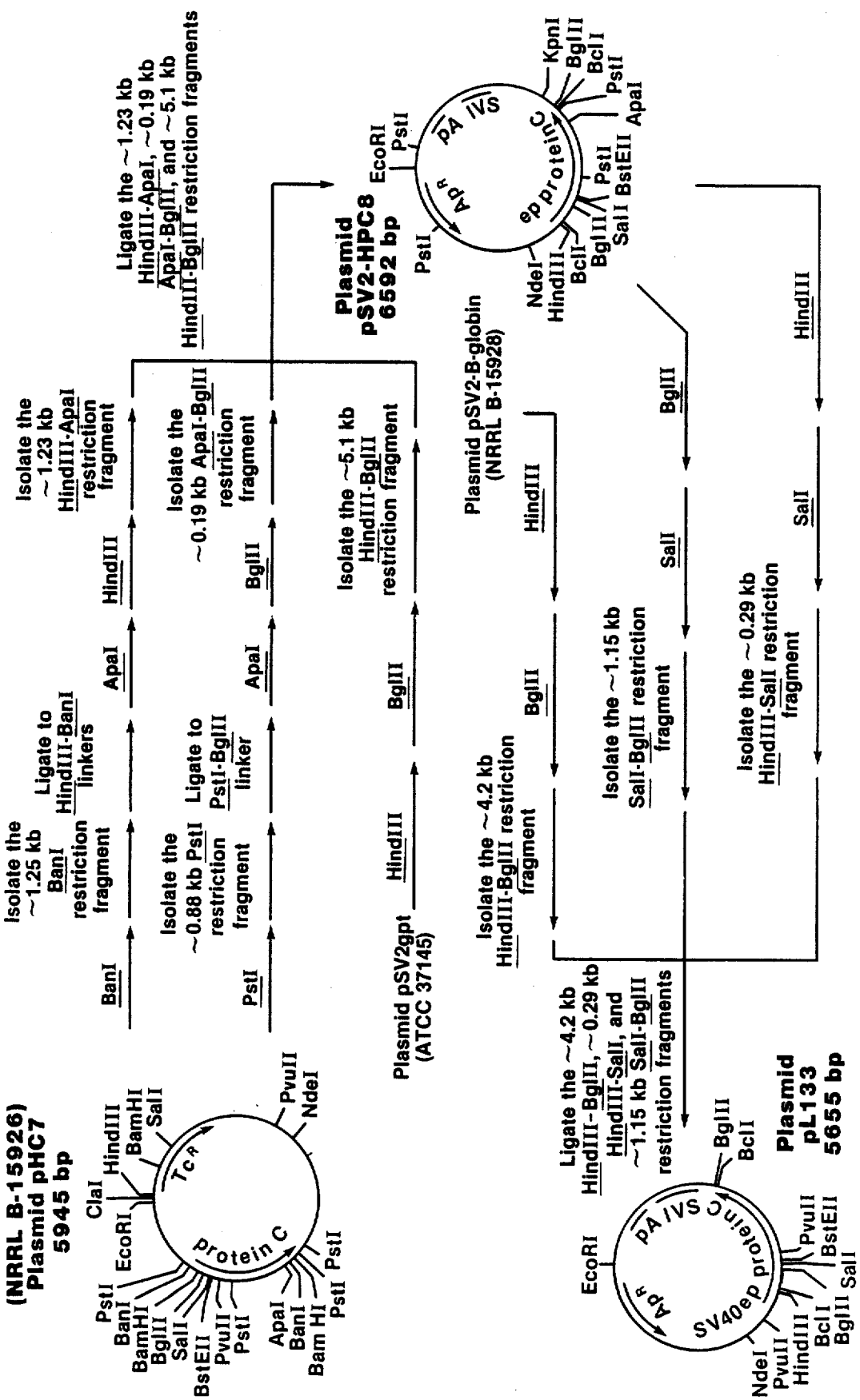
FIG. 7—a schematic showing the construction of plasmid pL133.

Plasmid pL133 was next constructed from 1 plasmids pHC7, pSV2gpt and pSV2-β-globin. Plasmid pHC7 comprises a DNA sequence which encodes human protein C. Plasmid pHC7 can be isolated from E. coli K12 RRI/pHC7 which is available from the NRRL under accession number NRRL B-15926. Plasmid pHC7 was cut with restriction enzyme BanI and the ~1.25 kb restriction fragment was isolated. Linkers were added, and the fragment was then cut with restriction enzymes ApaI and HindIII, then the desired ~1.23 kb restriction fragment was isolated. Plasmid pHC7 was next cut with restriction enzyme PstI, the ~0.88 kb restriction fragment was isolated, linkers were added, the fragment was re-cut with restriction enzymes ApaI and BglII and the ~0.19 kb ApaI-BglII restriction fragment was isolated. Plasmid pSV2gpt (ATCC 37145) was digested with restriction enzymes HindIII and BglII and the ~5.1 kb fragment was isolated. The ~1.23 kb HindIII-ApaI restriction fragment, the ~0.19 kb ApaI-BglII fragment and the ~5.1 kb HindIII-BglII fragment were then ligated together to form intermediate plasmid pSV2-HPC8. A more detailed explanation of the construction of plasmid pSV2-HPC8 is presented in Example 13. A schematic of this construction is presented in FIG. 7 of the accompanying drawings.

Figure 8:
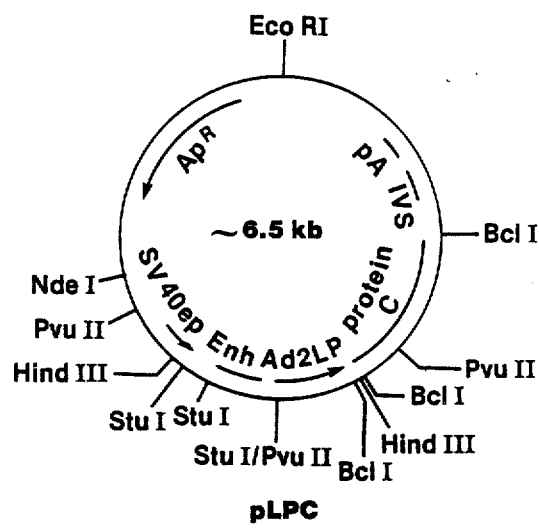
FIG. 8—the restriction site and function maps of plasmids pLPC, pSV2hyg and pLPChyg1.
Figure 8:
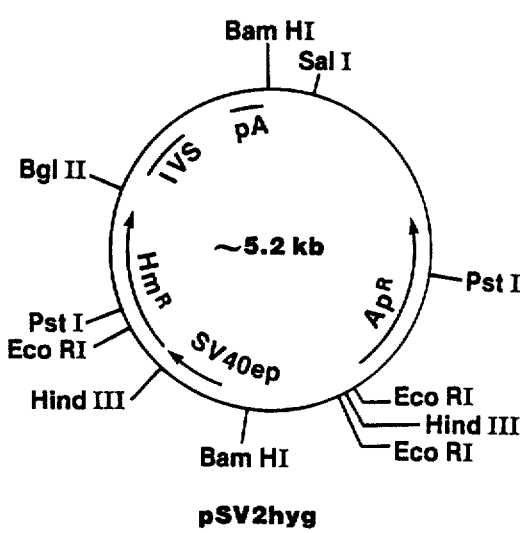
Figure 8:
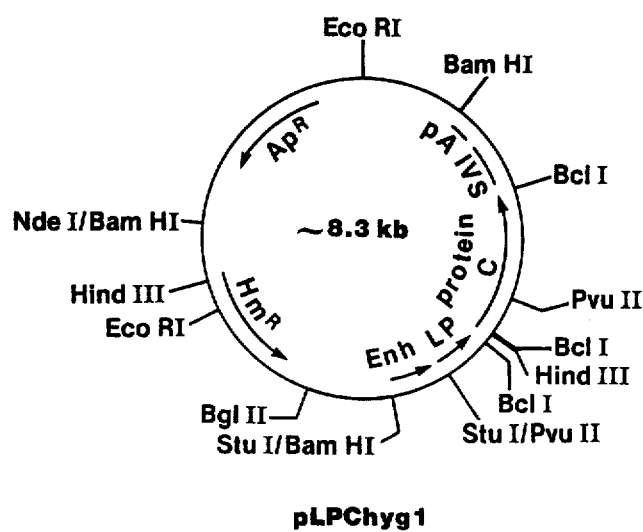

Plasmid pSV2-HPC8 was then cut with restriction enzymes HindIII and SalI, and the ~0.29 kb restriction fragment was isolated. Likewise, plasmid pSV2-HPC8 was also cut with restriction enzymes BglII and SalI, and the ~1.15 kb restriction fragment was isolated. Plasmid pSV2-β-globin (NRRL B-15928) was cut with restriction enzymes BglII and HindIII and the ~4.2 kb restriction fragment was isolated. These three fragments were then ligated together to form plasmid pL133. Plasmid pL133 was digested with restriction enzyme HindIII, then treated with alkaline phosphatase. Plasmid pBLcat was also cut with restriction enzyme HindIII and the ~0.87 kb restriction fragment was isolated. This fragment was ligated into the HindIII cut, phosphatased plasmid pL133 vector to form plasmid pLPC. Because the HindIII fragment of plasmid pBLcat can be inserted into plasmid pL133 in two orientations, it should be noted that pLPC is the plasmid wherein the proper orientation provides an ~1.0 kb NdeI-StuI fragment. Plasmid pLPC, like plasmid pL133, comprises the enhancer, early and late promoters, T-antigen-binding sites, and origin of replication of SV40. Detailed protocols for the construction of plasmids pL133 and pLPC are provided in Examples 13 and 14. Restriction site and function maps of plasmids pL133 and pLPC are presented respectively in FIGS. 7 and 8 of the accompanying drawings.

The SV40 elements present on plasmid pLPC are situated closely together and are difficult to delineate. The binding of T antigen to the T-antigen-binding sites, which is necessary for SV40 replication, is known to enhance transcription from the SV40 late promoter and surprisingly has a similar effect on the BK late promoter. Because the high level of T-antigen-driven replication of a plasmid that comprises the SV40 origin of replication is generally lethal to the host cell, neither plasmid pLPC nor plasmid pL133 are stably maintained as episomal (extrachromosomal) elements in the presence of SV40 T antigen, but rather, the two plasmids must integrate into the chromosomal DNA of the host cell to be stably maintained. The overall structure of the BK enhancer region is quite similar to that of SV40, for the BK enhancer, origin of replication, early and late promoters, and the BK analogue of the T-antigen-binding sites are also closely situated and thus difficult to delineate on the BK viral DNA. However, when grown in the presence of BK T antigen, a plasmid that comprises the BK origin of replication and T-antigen-binding sites does not replicate to an extent that proves lethal and is stably maintained as an episomal element in the host cell. In addition, the T-antigen-driven replication can be used to increase the copy number of a vector comprising the BK origin of replication so that when selective pressure is applied more copies of the plasmid integrate into the host cell's chromosomal DNA. Apparently due to the similar structure-function relationships between the BK and SV40 T antigens and their respective binding sites, BK replication is also stimulated by SV40 T antigen.

Episomal maintenance of a recombinant DNA expression vector is not always preferred over integration into the host cell chromosome. However, due to the absence of a selectable marker that functions in eukaryotic cells, the identification of stable, eukaryotic transformants of plasmid pLPC is difficult, unless plasmid pLPC is cotransformed with another plasmid that does comprise a selectable marker. Consequently, plasmid pLPC has been modified to produce derivative plasmids that are selectable in eukaryotic host cells. This was done by ligating plasmid pLPC to a portion of plasmid pSV2hyg, a plasmid that comprises a hygromycin resistance-conferring gene. Plasmid pSV2hyg can be obtained from the Northern Regional Research Laboratory (NRRL), Peoria, IL 61640, under the accession number NRRL B-18039. A restriction site and function map of plasmid pSV2hyg is presented in FIG. 8 of the accompanying drawings.

Plasmid pSV2hyg was digested with restriction enzyme BamHI, and the ~2.5 kb BamHI restriction fragment, which comprises the entire hygromycin resistance-conferring gene, was isolated, treated with Klenow enzyme (the large fragment produced upon subtilisin cleavage of E. coli DNA polymerase I), and then ligated to the Klenow-treated, ~5.82 kb NdeI-StuI restriction fragment of plasmid pLPC to yield plasmids pLPChyg1 and pLPChyg2. Plasmids pLPChyg1 and pLPChyg2 differ only with respect to the orientation of the hygromycin resistance-conferring fragment. Plasmid pLPChyg1 contains an ~5.0 kb HindIII fragment whereas plasmid pLPChyg2 contains an ~1.0 kb fragment. The construction protocol for plasmids pLPChyg1 and pLPChyg2 is described in Example 15. A restriction site and function map of plasmid pLPChyg1 is presented in FIG. 8 of the accompanying drawings.

Figure 9:
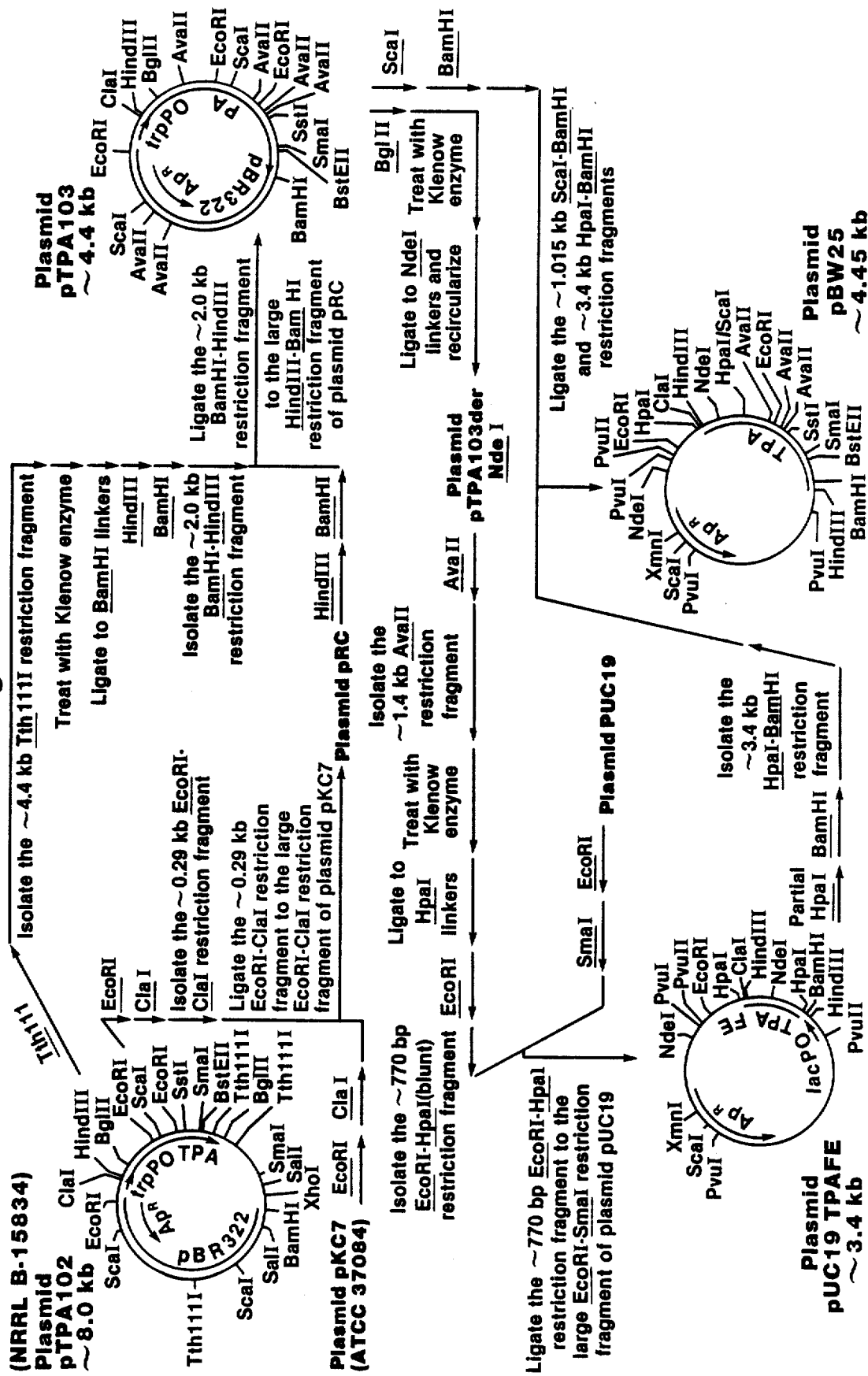
FIG. 9—a schematic showing the construction of plasmid pBW25.

Plasmid pBW32, which contains the murine dihydrofolate reductase (dhfr) gene, was constructed next. Plasmid pTPA102 (NRRL B-15834) was cut with restriction enzyme TthIIII and the ~4.4 kb restriction fragment was isolated. This fragment was treated with Klenow, linkers were added, then the fragment was cut with restriction enzymes HindIII and BamHI to yield an ~2.0 kb restriction fragment. Plasmid pRC was then constructed by ligating the ~288 bp ClaI-EcoRI restriction fragment of pTPA102 into ClaI-EcoRI cut vector pKC7. Plasmid pKC7 can be obtained from the ATCC under the accession number ATCC 37084. Plasmid pRC was digested with restriction enzymes BamHI and HindIII, then ligated to the ~2.0 kb restriction fragment of plasmid pTPA102, formed above, to yield plasmid pTPA103. The construction protocol for plasmid pTPA103 is described in Example 16A. A schematic of this construction is presented in FIG. 9 of the accompanying drawings.

Plasmid pTPA103 was cut with restriction enzyme BglII, treated with Klenow, and the NdeI linkers were added. This mixture was then ligated to form plasmid pTPA103derNdeI. Plasmid pTPA103derNdeI was cut with restriction enzyme AvaII, and the ~1.4 kb fragment was isolated. This fragment was treated with Klenow, then, after the addition of HpaI linkers, was cut with restriction enzyme EcoRI. The ~770 bp fragment, containing trpPO and the amino terminus of TPA, was ligated into EcoRI-SmaI digested vector pUC19, to form pUC19TPAFE. Plasmid pUC19TPAFE was partially digested with restriction enzyme HpaI, then totally cut with restriction enzyme BamHI. The resultant ~3.42 kb HpaI-BamHI restriction fragment was then ligated to the ~1.015 ScaI-BamHI fragment derived from plasmid pTPA103 to form plasmid pBW25. The construction protocol for plasmid pBW25 is described in Example 16B. A schematic of this construction is presented in FIG. 9 of the accompanying drawings.

Figure 10:
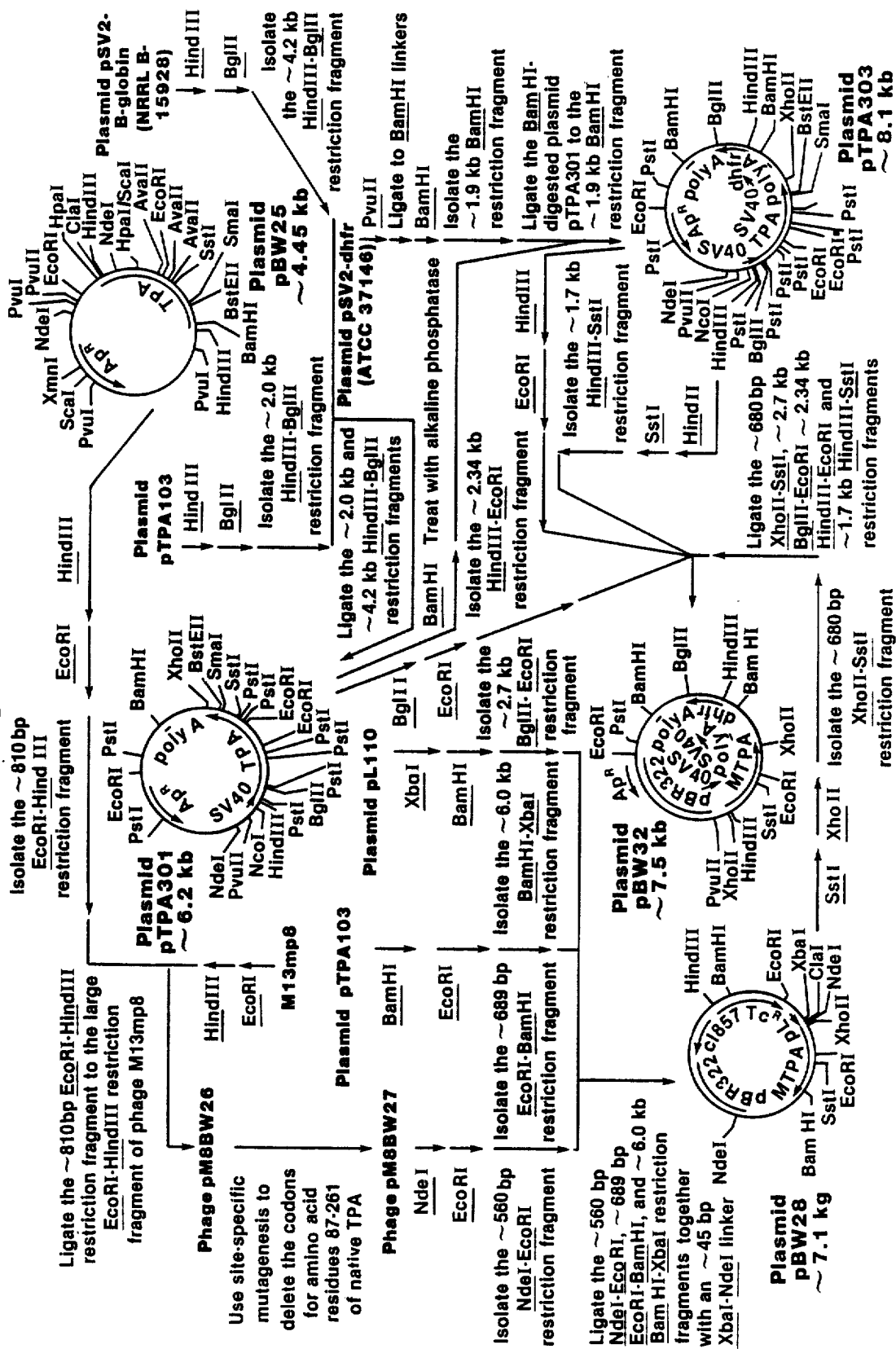
FIG. 10—a schematic showing the construction of plasmid pBW32.

Plasmid pBW25 was cut with restriction enzymes HindIII and EcoRI and the resultant ~810 bp fragment was ligated into HindIII-EcoRI cut phage M13mp8 (New England Biolabs) to form phage pM8BW26. An in vitro mutagenesis reaction was then performed on phage pM8BW26 (deleting DNA coding for amino acid residues) to form phage pM8BW27. Phage pM8BW27 was cut with restriction enzymes EcoRI and NdeI and the ~560 bp restriction fragment was isolated. A synthetic NdeI-XbaI linker of ~48 bp was synthesized. Plasmid pTPAI03 was cut with restriction enzymes EcoRI and BamHI and the ~689 bp fragment was isolated. Plasmid pL110 (constructed in Example 9) was partially digested with restriction enzyme BamHI, then totally cut with XbaI and the ~6.0 kb fragment was isolated. This ~6.0 kb vector fragment, the ~689 bp fragment of plasmid pTPA103, the ~560 bp fragment of phage pM8BW27, and the ~48 bp linker were all then ligated together to form plasmid pBW28. The construction protocol of plasmid pBW28 is described in Example 16C. A schematic of this construction is presented in FIG. 10 of the accompanying drawings.

Plasmid pTPA301 was next formed by ligating the ~2.0 kb HindIII-BglII fragment of plasmid pTPA103 to the ~4.2 kb HindIII-BglII fragment of plasmid pSV2-β-globin. Plasmid pSV2-dhfr (ATCC 37146) was cut with restriction enzyme PvuII. Following the addition of BamHI linkers, the ~1.9 kb dhfr gene-containing fragment was ligated into BamHI cut, phosphatased plasmid pTPA301 to form plasmid pTPA303. Plasmid pTPA301 was cut with restriction enzymes EcoRI and BglII to yield an ~2.7 kb fragment. Plasmid pTPA303 was cut with restriction enzymes HindIII and EcoRI to yield the ~2340 bp dhfr gene containing fragment. Plasmid pTPA303 was cut with restriction enzymes HindIII and SstI to yield an ~1.7 kb fragment. Plasmid pBW28 was cut with restriction enzymes XhoII and SstI to yield an ~680 bp fragment. The ~2.7 kb EcoRI-BglII fragment of plasmid pTPA301, the ~2340 bp HindIII-EcoRI fragment of plasmid pTPA303, the ~1.7 kb HindIII-SstI fragment of plasmid pTPA303 and the ~680 bp XhaII-SstI fragment of plasmid pBW28 were all ligated together to form plasmid pBW32. The construction protocol of plasmid pBW32 is described in Example 16D. A schematic of the construction is presented in FIG. 10 of the accompanying drawings.

The dhfr gene-containing, ~1.9 kb BamHI restriction fragment of plasmid pBW32 was isolated, treated with Klenow enzyme, and inserted into partially-EcoRI-digested plasmid pLPChyg1 to yield plasmids pLPChd1 and pLPChd2. Plasmid pLPChyg1 contains two EcoRI restriction enzyme recognition sites, one in the hygromycin resistance-conferring gene and one in the plasmid pBR322-derived sequences. The fragment comprising the dhfr gene was inserted into the EcoRI site located in the pBR322-derived sequences of plasmid pLPChyg1 to yield plasmids pLPChd1 and pLPChd2. For the purposes of this disclosure, plasmid pLPChd1 has been designated plasmid pLPChd. A restriction site and function map of plasmid pLPChd is presented in FIG. 11 of the accompanying drawings. The construction of plasmids pLPChd1 and pLPChd2, which differ only with respect to the orientation of the dhfr gene-containing DNA segment, is described in Example 17.

Plasmid phd was next constructed by transforming and re-isolating plasmid pLPChd through a dam⁻ strain of *E. coli*. Plasmid pLPChd was then digested with restriction enzyme BclI and recircularized to form plasmid phd. Plasmid phd results from the deletion of the extra BclI linkers that attached during the construction of plasmid pLPcat and the two adjacent BclI restriction fragments of a total size of about 1.45 kb from plasmid pLPChd. The DNA encoding the full length cDNA which encodes the light chain of monoclonal antibody KS1/4 is ligated into plasmid phd to form expression vector pL-KSL. The ~1100 base pair EcoRI fragment of plasmid pGKC2310 is treated with Klenow, ligated to BamHI linkers, then ligated into BclI-digested plasmid phd. Detailed descriptions of the construction of plasmids phd and pL-KSL are provided in Examples 18 and 19. A restriction site and function map of plasmid phd is presented in FIG. 11 of the accompanying drawings.

Plasmid pH-KS is a vector of the present invention derived from plasmid phd and plasmid pG2A52. The ~1.6 kb EcoRI fragment of plasmid pG2A52 is isolated, treated with Klenow and joined to BamHI linkers. This fragment comprises the full length cDNA which encodes the heavy chain of monoclonal antibody KS1/4. This fragment is next ligated into BclI-digested plasmid phd to form expression plasmid pH-KS. Plasmid pL-HD is an expression vector constructed from plasmid phd and plasmid CHKC2-18, which contains DNA encoding a derivative of the KS1/4 light chain variable region joined to a human light chain constant region. The ~1.3 kb FnuDII-HindIII fragment of plasmid CHKC2-18 was isolated and treated with Klenow. This fragment was then ligated into BclI-digested, Klenow treated plasmid phd to form expression plasmid pL-HD. Detailed descriptions of the construction of plasmids pH-KS and pL-HD are presented respectively in Examples 20 and 21.

Plasmid pL-HD2 is an expression vector constructed from plasmid phd and plasmid CHKC2-6, which contains DNA encoding the natural sequence of the KS1/4 light chain variable region joined to a human light chain constant region. The ~1.3 kb FnuDII-HindIII fragment of plasmid CHKC2-18 was isolated and treated with Klenow. This fragment was then ligated into BclI-digested, Klenow-treated plasmid phd to form expression plasmid pL-HD2. Plasmid pH1-HD, which contains cDNA encoding the heavy chain variable region of KS1/4 joined to genomic DNA encoding a human IgG1 constant region, was constructed from plasmid phd and plasmid CH2A5. Plasmid CH2A5 was digested with restriction enzyme EcoRI, treated with Klenow, then ligated to BamHI linkers. Next, the plasmid was digested with restriction enzyme BamHI and the ~7.4 kb restriction fragment was isolated. This fragment was ligated into BclI-digested plasmid phd to form expression plasmid pH1-HD. Detailed descriptions of the construction of plasmids pL-HD2 and pH1-HD are presented respectively in Examples 22 and 23.

Plasmid pH2-HD, which contains cDNA encoding the heavy chain variable region of KS1/4 joined to genomic DNA encoding a human IgG2 constant region, was constructed from plasmid phd and plasmid CH2A5IG2. Plasmid CH2A5IG2 was digested with restriction enzyme EcoRI, treated with Klenow, then ligated to BamHI linkers. Next, the plasmid was digested with restriction enzyme BamHI and the ~6.1 kb restriction fragment was isolated. This fragment was ligated into BclI-digested plasmid phd to form expression plasmid pH2-HD. Plasmid pH3-HD, which contains cDNA encoding the heavy chain variable region of KS1/4 joined to genomic DNA encoding a human IgG3 constant region, was constructed from plasmid phd and plasmid CH2A5IG3. Plasmid CH2A5IG3 was digested with restriction enzyme EcoRI, treated with Klenow, then ligated to BamHI linkers. Next, the plasmid was digested with restriction enzyme BamHI and the ~7.4 kb restriction fragment was isolated. This fragment was ligated into BclI-digested plasmid phd to form expression plasmid pH3-HD. Detailed descriptions of the construction of plasmids pH2-HD and pH3-HD are presented respectively in Examples 24 and 25.

Plasmid pH4-HD, which contains cDNA encoding the heavy chain variable region of KS1/4 joined to genomic DNA encoding a human IgG4 constant region, was constructed from plasmid phd and plasmid CH2A5IG4. Plasmid CH2A5IG4 was digested with restriction enzyme EcoRI, treated with Klenow, then ligated to BamHI linkers. Next, the plasmid was digested with restriction enzyme BamHI and the ~6.4 kb restriction fragment was isolated. This fragment was ligated into BclI-digested plasmid phd to form expression plasmid pH4-HD. A more detailed description of the construction is presented in Example 26.

The present invention is in no way limited to the use of the particular eukaryotic promoters exemplified herein. Other promoters, such as homologous or heterologous immunoglobulin promoters, the SV40 late promoter or promoters from eukaryotic genes, such as for example, the estrogen-inducible chicken ovalbumin gene, the interferon genes, the glucocorticoid-inducible tyrosine aminotransferase gene, the thymidine kinase gene, the major early adenovirus gene, and the SV40 early promoter, can be readily isolated and modified for use on recombinant DNA expression vectors designed to produce antibodies in eukaryotic host cells. Eukaryotic promoters can also be used in tandem to drive expression of such antibodies. Furthermore, a large number of retroviruses are known that infect a wide range of eukaryotic host cells. Long terminal repeats in the retrovirus DNA often encode promoter activity and can be used, in place of the BK enhancer-adenovirus late promoter described above, to drive expression of KS1/4 and its derivatives. Neither is the present invention limited to the actual selectable marker exemplified on the plasmids exemplified herein. A wide variety of selectable markers exist, both for eukaryotic and prokaryotic host cells, that are suitable for use on a recombinant DNA cloning or expression vector comprising a DNA compound (or sequence) of the present invention.

The various expression vectors can be transformed into and expressed in a variety of eukaryotic, especially mammalian, host cells. The expression vectors also comprise sequences that allow for replication in E. coli, as it is usually more efficient to prepare plasmid DNA in E. coli than in other host cells. Expression of antibodies occurs in host cells in which the particular promoter associated with the antibody's structural gene functions. Skilled artisans will understand that a variety of eukaryotic host cells can be used to express the various antibodies using the BK enhancer-adenovirus late promoter, so long as the host cell expresses an immediate-early gene product of a large DNA virus. Because the immediate-early gene product can be introduced into host cells by many means, such as transformation with a plasmid or other vector, virtually any eukaryotic cell can be used in the present method. Human cells are preferred host cells in the method of the present invention, because human cells are the natural host for BK virus and may contain cellular factors that serve to stimulate the BK enhancer. While human cells may be used as host cells, the adenovirus 12-transformed Syrian Hamster cell line AV12, which expresses the EIA gene product, is most preferred and is available from the American Type Culture Collection in Rockville, Maryland, under the accession number ATCC CRL 9595. The normal transformation procedure is described in detail in Example 27.

When transformed with an expression vector that encodes an immunoglobulin heavy chain, AV12 cells secrete the processed heavy chain into the supernatant. However, AV12 cells transformed with an expression vector which encodes a light chain do not secrete said light chain unless the cells are also co-transformed with an expression vector encoding a heavy chain. A procedure for isolating clones which express the various immunoglobulin chains of the present invention is presented in Example 28. Functional KS1/4 and KS1/4 derivatives can therefore be purified from the supernatant of AV12 cells which have been co-transformed with vectors encoding light and heavy chains. In this manner, many variants of KS1/4 can be produced by mixing and matching the different light and heavy chains of the present invention.

The expression of immunoglobulin light and heavy chain molecules in a non-lymphoid system constitutes a marked advantage over lymphoid systems. Traditionally, monoclonal antibodies have been isolated and purified from lymphoid systems such as myeloma or hybridoma cells. Such cells often express substantial quantities of heterogenic antibodies. This phenomena arises from the fact that lymphoid cells naturally secrete antibodies. When transformed with DNA encoding a separate antibody, or fused with other cells which produce a distinct antibody, such lymphoid cells sometimes become dual secreters. Dual secreting cells lines then produce many antibodies with hybrid molecular structures, a large population of which are not desired. These unwanted hybrids must then be separated from the intended product using costly and time consuming techniques. The method of the present invention traverses this problem in that non-lymphoid cells do not naturally secrete antibody molecules. Therefore, the only antibody which is secreted into the supernatant is the homogeneous product desired.

Many modifications and variations of the present illustrative DNA sequences and plasmids are possible. For example, the degeneracy of the genetic code allows for the substitution of nucleotides throughout polypeptide coding regions as well as for the substitution of the $$\begin{array}{c} \text{TAA} \\ | \; | \; | \\ \text{ATT} \end{array}$$

translational stop signal for the $$\begin{array}{cc} \text{TAG} & \text{or} \quad \text{TGA} \\ | \; | \; | & \quad | \; | \; | \\ \text{ATC} & \quad \text{ACT} \end{array}$$

translational stop signals specifically exemplified. Such sequences can be deduced from the now-known amino acid or DNA sequence of KS1/4 and can be constructed by following conventional synthetic procedures. Such synthetic methods can be carried out in substantial accordance with the procedures of Itakura et al., 1977 Science 198:1056 and Crea et al., 1978, Proc. Nat. Acad. Sci. U.S.A. 75:5765. In addition, synthetic genes and linkers can be synthesized either by using a Systec 1450A DNA synthesizer (Systec Inc., 3816 Chandler Drive, Minneapolis, Minn.) or an ABS 380A DNA synthesizer (Applied Biosystems, Inc., 850 Lincoln Center Drive, Foster City, Calif. 94404). Many other DNA synthesizing instruments are known in the art and can be used to make synthetic DNA fragments. Therefore, the present invention is in no way limited to the DNA sequences and plasmids specifically exemplified.

Those skilled in the art will recognize that the expression vectors of this invention are used to transform eukaryotic host cells, such that polypeptides with various light and heavy chain structures are expressed by the host cell. If the host cell is transformed with a vector comprising a promoter that functions in the host cell and drives transcription of the such immunoglobulin structural genes, and if the host cell possesses the cellular machinery with which to process the signal peptides, mature antibodies or antibody chains are secreted by such cells. Under other expression conditions, such as when only immunoglobulin light chains are expressed by the host cell, the light chains must be isolated from the host cell.

As stated above, the vectors, methods, transformants and antibodies of the present invention will have a profound effect upon the battle against cancer. Monoclonal antibody KS1/4 has been shown to be an effective agent for the diagnosis, prognosis and treatment of adenocarcinoma by Bumol in Reisfeld, R. A. and Sell, S. eds. Monoclonal Antibodies and Cancer Therapy. New York: Alan R. Liss, Inc., 1985, 257–259. Spearman et al., 1987, J. Pharmacol. and Exp. Therapeutics 241:695–703, the teaching of which is herein incorporated by reference, disclosed the use of a monoclonal antibody-vinca alkaloid conjugate in the localization and treatment of tumors. This KS1/4-DAVLB(4-desacetylvinblastine) conjugate was also responsible for tumor growth suppression as disclosed by Bumol et al, in Ceriani, R. L. ed. Immunologic Approaches to the Diagnosis and Therapy of Breast Cancer, New York and London: Plenum Press; 1987, 205–215, the teaching of which is herein incorporated by reference. Biochemical and immunological studies have revealed that the recombinant and chimeric KS1/4 molecules of the present invention possess the same antigen reactivity as KS1/4 molecules derived from hybridoma cells.

The problem with using a murine antibody, however, is that said antibodies often illicit an immunological response in human subjects. This has occurred in some patients receiving treatment with KS1/4. This problem can be circumvented by using the chimeric antibodies of the present invention. By replacing the constant regions of KS1/4 with constant regions of human origin, the patient's immune system will recognize the chimeric antibody as "self", and therefore create fewer anti-KS1/4 antibodies. Furthermore, the use of a human constant region will assist in the activation of complement and other cellular responses.

Skilled artisans will also recognize that the heretofore unknown amino acid and DNA sequences of KS1/4 can be used to create novel, high or low affinity derivatives. Various portions of the antibody may be deleted or mutated to create new antibodies, or portions of one chain may be replaced with a piece of another chain. X-Ray crystallographic studies will demonstrate which amino acid residues of the antibody appear in close proximity to amino acid residues of the antigen to which KS1/4 binds. By using protein engineering techniques, KS1/4 can be modified to provide negative residues near positive residues on the antigen. Such "engineered" antibodies will then display modified affinity to the cell surface antigen in cancer patients.

The following examples further illustrate the invention disclosed herein. The examples describe the procedures for the construction of the present invention, and explanations of the procedures as provided where appropriate.

EXAMPLE 1

Isolation of Plasmid pKC283

Lyophils of *E. coli* K12 BE1201/pKC283 are obtained from the Northern Regional Research Laboratory, Peoria, Ill. 61604, under the accession number NRRL B-15830. The lyophils are decanted into tubes containing 10 ml LB medium (10 g Bacto-tryptone, 5 g Bacto-yeast extract, and 10 g NaCl per liter; pH is adjusted to 7.5) and incubated two hours at 32° C., at which time the cultures are made 50 µg/ml in ampicillin and then incubated at 32° C. overnight. The *E. coli* K12 BE1201/pKC283 cells were cultured at 32° C., because the cells comprise a temperature-sensitive cI repressor gene integrated into the cellular DNA. When cells that comprise a wild-type lambda pL repressor gene or do not comprise a lambda pL promoter are utilized in this plasmid isolation procedure, as described in subsequent Examples herein, the temperature of incubation is 37° C.

A small portion of the overnight culture is placed on LB-agar (LB medium with 15 g/l Bacto-agar) plates containing 50 µg/ml ampicillin in a manner so as to obtain a single colony isolate of *E. coli* K12 BE1201/pKC283. The single colony obtained was inoculated into 10 ml of LB medium containing 50 µg/ml ampicillin and incubated overnight at 32° C. with vigorous shaking. The 10 ml overnight culture was inoculated into 500 ml LB medium containing 50 µg/ml ampicillin and incubated at 32° C. with vigorous shaking until the culture reached stationary phase.

The following procedure is adapted from Maniatis et al., 1982, *Molecular Cloning* (Cold Spring Harbor Laboratory).

The cells were harvested by centrifugation at 4000 g for 10 minutes at 4° C., and the supernatant was discarded. The cell pellet was washed in 100 ml of ice-cold STE buffer (0.1M NaCl; 10 mM Tris-HCl, pH 7.8; and 1 mM EDTA). After washing, the cell pellet was resuspended in 10 ml of Solution 1 (50 mM glucose; 25 mM Tris-HCl, pH 8.0; and 10 mM EDTA) containing 5 mg/ml lysozyme and left at room temperature for 10 minutes. Twenty ml of Solution 2 (0.2N NaOH and 1% SDS) were then added to the lysozyme-treated cells, and the solution was gently mixed by inversion. The mixture was incubated on ice for 10 minutes.

Fifteen ml of ice-cold 5M potassium acetate, pH 4.8, were added to the lysed-cell mixture and the solution mixed by inversion. The solution was incubated on ice for 10 minutes. The 5M potassium acetate solution was prepared by adding 11.5 ml of glacial acetic acid to 28.5 ml of water and 60 ml of 5M potassium acetate; the resulting solution is 3M with respect to potassium and 5M with respect to acetate.

The lysed cell mixture was centrifuged in a Beckman SW27 (or its equivalent) at 20,000 rpm for 20 minutes at 4° C. The cell DNA and debris formed a pellet on the bottom of the tube. About 36 ml of supernatant were recovered, and 0.6 volumes of isopropanol were added, mixed, and the resulting solution left at room temperature for 15 minutes. The plasmid DNA was collected by centrifugation at 12,000 g for 30 minutes at room temperature. The supernatant was discarded, and the DNA pellet was washed with 70% ethanol at room temperature. The ethanol wash was decanted, and the pellet was dried in a vacuum desiccator. The pellet was then resuspended in 8 ml of TE buffer (10 mM Tris-HCl, pH 8.0, and 1 mM EDTA).

Eight grams of CsCl were added to the DNA solution. About 0.8 ml of a 10 mg/ml solution of ethidium bromide in water were added for each 10 ml of CsCl-DNA solution. The final density of the solution was about 1.55 g/ml, and the ethidium bromide concentraton was about 600 µg/ml. The solution was transferred to a Beckman Type 50 centrifuge tube, filled to the top with paraffin oil, sealed, and centrifuged at 45,000 rpm for 24 hours at 20° C. After centrifugation, two bands of DNA were visible in ordinary light. After removing the cap from the tube, the lower DNA band was removed by using a syringe with a #21 hypodermic needle inserted through the side of the centrifuge tube.

The ethidium bromide was removed by several extractions with water-saturated 1-butanol. The CsCl was removed by dialysis against TE buffer. After extractions with buffered phenol and then chloroform, the DNA was precipitated, washed with 70% ethanol, and dried. About 1 mg of plasmid pKC283 was obtained and stored at 4° C. in TE buffer at a concentration of about 1 μg/μl. A restriction site and function map of plasmid pKC283 is presented in FIG. 1 of the accompanying drawings.

EXAMPLE 2

Construction of Plasmid pKC283PX

About 10 μl of the plasmid pKC283 DNA prepared in Example 1 were mixed with 20 μl 10 X medium-salt restriction buffer (500 mM NaCl; 100 mM Tris-HCl, pH 7.5; 100 mM MgCl$_2$; and 10 mM DTT), 20 μl 1 mg/ml BSA, 5 μl restriction enzyme PvuII (~50 Units, as defined by Bethesda Research Laboratories (BRL), from which all restriction enzymes used herein were obtained), and 145 μl of water, and the resulting reaction was incubated at 37° C. for 2 hours. Restriction enzyme reactions described herein were routinely terminated by phenol and then chloroform extractions, which were followed by precipitation of the DNA, an ethanol wash, and resuspension of the DNA in TE buffer. After terminating the PvuII digestion as described above, the PvuII-digested plasmid pKC283 DNA was precipitated and then resuspended in 5 μl of TE buffer.

About 600 picomoles (pM) of XhoI linkers (5'-CCTCGAGG-3') were kinased in a mixture containing 10 μl 5 X Kinase Buffer (300 mM Tris-HCl, pH 7.8; 50 mM MgCl$_2$; and 25 mM DTT), 5 μl 5 mM ATP, 24 μl H$_2$O, 0.5 μl of T4 polynucleotide kinase (about 2.5 units as defined by P-L Biochemicals), 5 μl 1 mg/ml BSA, and 5 μl of 10 mM spermidine by incubating the mixture at 37° C. for 30 minutes.

About 12.5 μl of the kinased XhoI linkers were added to the 5 μl of PvuII-digested plasmid pKC283 DNA, and then 2.5 μl of 10 X ligase buffer (300 mM Tris-HCl, pH 7.6; 100 mM MgCl$_2$; and 50 mM DTT), 2.5 μl of 1 mg/ml BSA, 7 μl of 5 mM ATP, 2.5 μl (about 2.5 units as defined by P-L Biochemicals) of T4 DNA ligase, 2.5 μl of 10 mM spermidine, and 3 μl of water were added to the DNA. The resulting ligation reaction was incubated at 4° C. overnight. After the ligation reaction, the reaction mixture was adjusted to have the composition of high-salt buffer (0.1M NaCl; 0.05M Tris-HCl, pH 7.5; 10.0 mM MgCl$_2$; and 1 mM DTT). About 10 μl (100 units) of restriction enzyme XhoI were added to the mixture, and the resulting reaction was incubated at 37° C. for 2 hours.

The reaction was terminated, and the XhoI-digested DNA was precipitated, resuspended, and ligated as described above, except that no XhoI linkers were added to the ligation mixture. The ligated DNA constituted the desired plasmid pKC283PX. A restriction site and function map of plasmid pKC283PX is presented in FIG. 1 of the accompanying drawings.

EXAMPLE 3

Construction of E. coli K12 MO(λ+)/pKC283PX

E. coli K12 MO(λ+) can be obtained from the Northern Regional Research Laboratories in lyophylized form under the accession number NRRL B-15993. E. coli K12 MO(λ+) comprises the wild-type lambda pL cI repressor gene, so that transcription from the hybrid pL-lpp promoter of the present invention does not occur in E. coli K12 MO(λ+) cells. The lyophils are reconstituted, single colonies of MO(λ+) are isolated, and a 10 ml overnight culture of the MO(λ+) cells is prepared in substantial accordance with the procedure of Example 1, except that the temperature of incubation is 37° C. and no ampicillin is used in the growth media.

Fifty μl of the overnight culture were used to inoculate 5 ml of LB media which also contained 10 mM MgSO$_4$ and 10 mM MgCl$_2$. The culture was incubated at 37° C. overnight with vigorous shaking. The following morning, the culture was diluted to 200 ml with LB media containing 10 mM MgSO$_4$ and 10 mM MgCl$_2$. The diluted culture was incubated at 37° C. with vigorous shaking until the absorbance at 550 nm (A$_{550}$) was about 0.5, which indicated a cell density of about 1×10$^8$ cells/ml. The culture was cooled for ten minutes in an ice-water bath, and the cells were then collected by centrifugation at 4000 g for 10 minutes at 4° C. The cell pellet was resuspended in 100 ml of cold 10 mM MgSO$_4$ and then immediately re-pelleted by centrifugation. The cell pellet was resuspended in 100 ml of 30 mM CaCl$_2$ and incubated on ice for 20 minutes.

The cells were again collected by centrifugation and resuspended in 10 ml of 30 mM CaCl$_2$. A one-half ml aliquot of the cells was added to the ligated DNA prepared in Example 2; the DNA had been made 30 mM in CaCl$_2$. The cell-DNA mixture was incubated on ice for one hour, heat-shocked at 42° C. for 90 seconds, and then chilled on ice for about two minutes. The cell-DNA mixture was diluted into 10 ml of LB media in 125 ml flasks and incubated at 37° C. for one hour. One hundred μl aliquots were plated on LB-agar plates containing ampicillin and incubated at 37° C. until colonies appeared.

The colonies were individually cultured, and the plasmid DNA of the individual colonies was examined by restriction enzyme analysis and gel electrophoresis. Plasmid DNA isolation was performed on a smaller scale in accordance with the procedure of Example 1, but the CsCl gradient step was omitted until the desired E. coli K12 MO(λ+)/pKC283PX transformants were identified. A restriction site and function map of plasmid pKC283PX is presented in FIG. 1 of the accompanying drawings.

EXAMPLE 4

Construction of E. coli K12 MO(λ+)/pKC283-L

Ten μg of plasmid pKC283PX DNA prepared in accordance with the procedure of Example 1 were dissolved in 20 μl of 10X high-salt buffer, 20 μl 1 mg/ml BSA, 5 μl (~50 units) restriction enzyme BglII, 5 μl (~50 units) restriction enzyme XhoI, and 150 μl of water, and the resulting reaction was incubated at 37° C. for two hours. The reaction was stopped, and after precipitating the BglII-XhoI digested DNA, the DNA was resuspended in 5 μl of TE buffer.

A DNA linker with single-stranded DNA ends characteristic of BglII and XhoI restriction enzyme cleavage was synthesized and kinased. The linker was kinased in substantial accordance with the procedure of Example 2. The DNA linker had the following structure:

The linker depicted above was synthesized from single-stranded deoxyoligonucleotides by procedures well known in the art. The single-stranded deoxyoligonucleotides can be synthesized with commercially available instruments, such as the 380A DNA Synthesizer marketed by Applied Biosystems (850 Lincoln Centre Drive, Foster City, Calif. 94404), which utilizes phosphoramidite chemistry. Other procedures for synthesizing DNA are also known in the art. The conventional modified phosphotriester method of synthesizing single stranded DNA is described in Itakura et al., 1977, Science 198:1056 and in Crea et al., 1978, Proc. Nat. Acad. Sci. USA 75:5765. In addition, an especially preferred method of synthesizing DNA is disclosed in Hsiung et al., 1983, Nucleic Acid Research 11:3227 and Narang et al., 1980, Methods in Enzymology 68:90.

The linker and BglII-XhoI-digested plasmid pKC283PX were ligated in substantial accordance with the procedure of Example 2. The ligated DNA constituted the desired plasmid pKC283-L. A restriction site and function map of plasmid pKC283-L is presented in FIG. 1 of the accompanying drawings. The plasmid pKC283-L DNA was used to transform E. coli K12 MO(λ+) and the resulting E. coli K12 MO(λ+)/pKC283-L transformants were identified in substantial accordance with the procedure of Example 3.

EXAMPLE 5

Construction of E. coli K12 MO(λ+)/pKC283-LB

About 10 μg of plasmid pKC283-L DNA, prepared in substantial accordance with the procedures of Example 1, were dissolved in 20 μl 10X high-salt buffer, 20 μl 1 mg/ml BSA, 5 μl (~50 units) restriction enzyme XhoI, and 155 μl of H2O, and the resulting reaction was incubated at 37° C. for two hours. The XhoI-digested plasmid pKC283-L DNA was then precipitated from the reaction mixture by the addition of three volumes of 95% ethanol and one-tenth volume of 3M sodium acetate, incubation in a dry ice-ethanol bath for five minutes, and centrifugation. The resulting DNA pellet was washed with 70% ethanol, dried, and resuspended in 2 μl 10X nick-translation buffer (0.5M Tris-HCl, pH 7.2; 0.1M MgSO4; and 1 mM DTT), 1 μl of a solution 2 mM in each of the deoxynucleotide triphosphates, 15 μl of H2O, 1 μl (~6 units as defined by P-L Biochemicals) of Klenow, which is the large fragment of E. coli DNA polymerase I, and 1 μl of 1 mg/ml BSA. The resulting reaction was incubated at 25° C. for 30 minutes; the reaction was stopped by incubating the solution at 70° C. for five minutes.

BamHI linkers (5'-CGGGATCCCG-3') were kinased and ligated to the XhoI-digested, Klenow-treated plasmid pKC283-L DNA in substantial accordance with the procedure of Example 2. After the ligation reaction, the DNA was digested with about 100 units of BamHI for about 2 hours at 37° C. in high-salt buffer. After the BamHI digestion, the DNA was prepared for ligation in substantial accordance with the procedure of Example 2.

The ~5.9 kb BamHI restriction fragment was circularized by ligation and transformed into E. coli K12 MO(λ+) in substantial accordance with the procedures of Examples 2 and 3. The E. coli K12 MO(λ+)/pKC283-LB transformants were identified, and then plasmid pKC283-LB DNA was prepared in substantial accordance with the procedure of Example 1. A restriction site and function map of plasmid pKC283-LB is presented in FIG. 1 of the accompanying drawings.

EXAMPLE 6

Construction of E. coli K12 MO(λ+)/pL32

About 10 μg of plasmid pKC283PX were digested with restriction enzyme SalI in high-salt buffer, treated with Klenow, and ligated to EcoRI linkers (5'-GAG-GAATTCCTC-3') in substantial accordance with the procedure of Example 5, with the exception of the starting plasmid, restriction enzymes, and linkers used. After digestion with restriction enzyme EcoRI, which results in the excision of ~2.1 kb of DNA, the ~4.0 kb EcoRI restriction fragment was circularized by ligation to yield plasmid pKC283PRS. The ligated DNA was used to transform E. coli K12 MO(λ+) in substantial accordance with the procedure of Example 3. After the E. coli K12 MO(λ+)/pKC283PRS transformants were identified, plasmid pKC283PRS DNA was prepared in substantial accordance with the procedure of Example 1. A restriction site and function map of plasmid pKC283PRS is presented in FIG. 1 of the accompanying drawings.

About 10 μg of plasmid pKC283PRS were digested in 200 μl of high-salt buffer with about 50 units each of restriction enzymes PstI and SphI. After incubating the reaction at 37° C. for about 2 hours, the reaction mixture was electrophoresed on a 0.6% low-gelling-temperature agarose (FMC Corporation, Marine Colloids Division, Rockland, Me. 04841) gel for 2-3 hours at ~130 V and ~75 mA in Tris-Acetate buffer.

The gel was stained in a dilute solution of ethidium bromide, and the band of DNA constituting the ~0.85 kb PstI-SphI restriction fragment, which was visualized with long-wave UV light, was cut from the gel in a small segment. The volume of the segment was determined by weight and density of the segment, and an equal volume of 10 mM Tris-HCl, pH 7.6, was added to the tube containing the segment. The segment was then melted by incubation at 72° C. About 1 μg of the ~0.85 kb PstI-SphI restriction fragment of plasmid pKC283PRS was obtained in a volume of about 100 μl. In an analogous manner, plasmid pKC283-LB was digested with restriction enzymes PstI and SphI, and the resulting ~3.0 kb restriction fragment was isolated by agarose gel electrophoresis and prepared for ligation.

The ~0.85 kb PstI-SphI restriction fragment of plasmid pKC283PRS was ligated to the ~3.0 kb PstI-SphI restriction fragment of plasmid pKC283-LB in substantial accordance with the procedure of Example 2. The ligated DNA constituted the desired plasmid pL32. A restriction site and function map of plasmid pL32 is presented in FIG. 1 of the accompanying drawings. Plasmid pL32 was transformed into E. coli K12 MO(λ+) cells in substantial accordance with the procedure of Example 3. Plasmid pL32 DNA was prepared from the *E. coli* K12 MO(λ+)/pL32 transformants in substantial accordance with the procedure of Example 1. Analysis of the plasmid pL32 DNA demonstrated that more than one EcoRI linker attached to the Klenow-treated, SalI ends of plasmid pKC283PX. The presence of more than one EcoRI linker does not affect the utility of plasmid pL32 or derivatives of plasmid pL32 and can be detected by the presence of an XhoI restriction site, which is generated whenever two of the EcoRI linkers are ligated together. Alternatively, plasmid pL32 may be constructed by carrying out the SalI-EcoRI excision and ligation of the first paragraph of this Example upon plasmid pKC283-LB.

EXAMPLE 7

Construction of *E. coli* K12 MO(λ+)/pL47

*E. coli* K12 RV308/pNM789 can be obtained from the Northern Regional Research Laboratories in lyophilized form under the accession number NRRL B-18216. A restriction site and function map of pNM789 is presented in FIG. 2 of the accompanying drawings. Plasmid DNA is extracted from the culture in substantial accordance with the teaching of Example 1, except that the temperature of incubation is 37° C. Ten micrograms of pNM789 are suspended in 200 μl PvuII buffer (50 mM Tris-HCl (pH 7.5), 60 mM NaCl and 6 mM $MgCl_2$). One unit of PvuII is added and the reaction mix is incubated for 5 minutes at 37° C. The enzyme is inactivated by heating 10 minutes at 65° C. 30 μl of 10X BamHI buffer (200 mM Tris-HCl (pH 8.0), 1M NaCl and 70 mM $MgCl_2$), 70 μl $H_2O$ and 10 units of BamHI are next added and the reaction is incubated for 1 hour at 37° C. This is followed by the addition of 5 units of alkaline phosphatase and incubation for 1 hour at 65° C. The DNA fragments are separated on a 1 percent agarose gel, and a DNA fragment (FIG. 3) the size of a single cut fragment is purified.

A DNA linker with a blunt end and a BamHI end is synthesized in substantial accordance with the teaching of Example 4. This linker (shown in FIG. 3) has the following structure:

The linker is kinased and ligated into the BamHI-PvuII digested plasmid pNM789 in substantial accordance with the teaching of Example 2. This ligation mixture is used to transform *E. coli* K12 RV308 cells and plasmid isolation is performed upon these transformants in substantial accordance with the teaching of Example 3. Several plasmids are selected which contain the appropriate size PvuII fragment (494 bp) and XbaI-BamHI fragment (628 bp). The sequence of at least two of these is determined by sequencing from the BamHI site toward the unique SmaI site and one clone is selected with the desired sequence. This intermediate plasmid is designated plasmid 120. A schematic outline of this procedure and a restriction site and function map of plasmid 120 is presented in FIG. 3 of the accompanying drawings.

To isolate the EK-BGH-encoding DNA, about 10 μg of plasmid 120 were digested in 200 μl of high-salt buffer containing about 50 units each of restriction enzymes XbaI and BamHI. The digestion products were separated by agarose gel electrophoresis, and the ~0.6 kb XbaI-BamHI restriction fragment which encodes EK-BGH was isolated and prepared for ligation in substantial accordance with the procedure of Example 6.

Plasmid pL32 was also digested with restriction enzymes XbaI and BamHI, and the ~3.9 kb restriction fragment was isolated and prepared for ligation. The ~3.9 kb XbaI-BamHI restriction fragment of plasmid pL32 was ligated to the ~0.6 kb XbaI-BamHI restriction fragment of plasmid 120 in substantial accordance with the procedure of Example 2 to yield plasmid pL47. A restriction site and function map of plasmid pL47 is presented in FIG. 4 of the accompanying drawings. Plasmid pL47 was transformed into *E. coli* K12 MO(λ+) in substantial accordance with the procedure of Example 3, and the *E. coli* K12 MO(λ+)/pL47 transformants were identified. Plasmid pL47 DNA was prepared from the transformants in substantial accordance with the procedures of Example 1.

EXAMPLE 8

Construction of *E. coli* K12 RV308/pPR12AR1

Plasmid pPR12 comprises the temperature-sensitive pL repressor gene cI857 and the plasmid pBR322 tetracycline resistance-conferring gene. Plasmid pPR12 is disclosed and claimed in U.S. Pat. No. 4,436,815, issued Mar. 13, 1984. A restriction site and function map of plasmid pPR12 is presented in FIG. 4 of the accompanying drawings.

About 10 μg of plasmid pPR12 were digested with about 50 units of restriction enzyme EcoRI in 200 μl of high-salt buffer at 37° C. for two hours. The EcoRI-digested plasmid pPR12 DNA was precipitated and treated with Klenow in substantial accordance with the procedure of Example 5. After the Klenow reaction, the EcoRI-digested, Klenow-treated plasmid pPR12 DNA was recircularized by ligation in substantial accordance with the procedure of Example 2. The ligated DNA, which constituted the desired plasmid pPR12ΔR1, was used to transform *E. coli* K12 RV308 in substantial accordance with the procedure of Example 3, except that selection was based on tetracycline (5 ug/ml) resistance, not ampicillin resistance. *E. coli* K12 RV308 is available from the NRRL under the accession number NRRL B-15624. After the *E. coli* K12 RV308/pPR12ΔR1 transformants were identified, plasmid pPR12ΔR1 DNA was prepared from the transformants in substantial accordance with the procedure of Example 1.

About 10 μg of plasmid pPR12ΔR1 were digested with about 50 units of restriction enzyme AvaI in 200 μl of medium-salt buffer at 37° C. for 2 hours. The AvaI-digested plasmid pPR12ΔR1 DNA was precipitated and treated with Klenow in substantial accordance with the procedure of Example 5. After the Klenow reaction, the AvaI-digested, Klenow-treated plasmid pPR12ΔR1 DNA was ligated to EcoRI linkers (5'-GAGGAATTCCTC-3') in substantial accordance with the procedure of Example 2. After the linker ligation, the DNA was precipitated and then resuspended in about 200 μl of high-salt buffer containing about 50 units of restriction enzyme EcoR1. The resulting reaction was incubated at 37° C. for about 2 hours. After the EcoRI digestion, the reaction mixture was loaded onto an agarose gel, and the ~5.1 kb EcoR1 restriction fragment was purified in substantial accordance with the procedure of Example 6. The ~5.1 kb EcoR1 restriction fragment was recircularized by ligation in substantial accordance with the procedure of Example 2. The ligated DNA constituted the desired plasmid pPR12AR1. The plasmid pPR12AR1 DNA was transformed into *E. coli* K12 RV308 in substantial accordance with the procedure of Example 3, except that selection was based on tetracycline resistance, not ampicillin resistance. After identifying the *E. coli* K12 RV308/pPR12AR1 transformants, plasmid pPR12AR1 DNA was prepared in substantial accordance with the procedure of Example 1. A restriction site and function map of plasmid pPR12AR1 is presented in FIG. 4 of the accompanying drawings.

EXAMPLE 9

Construction of *E. coli* K12 RV308/pL110

About 10 μg of plasmid pPR12AR1 DNA were suspended in about 200 ml of high-salt buffer containing about 50 units each of restriction enzymes PstI and EcoRI, and the digestion reaction was incubated at 37° C. for about 2 hours. The reaction mixture was then loaded onto an agarose gel, and the ~2.9 kb PstI-EcoRI restriction fragment of plasmid pPR12AR1 was isolated and prepared for ligation in substantial accordance with the procedure of Example 6.

About 10 ug of plasmid pL47 were digested with restriction enzymes PstI and BamHI in 200 ul of high-salt buffer at 37° C. for two hours. The PstI-BamHI-digested DNA was loaded onto an agarose gel, and the ~2.7 kb PstI-BamHI restriction fragment that comprised the origin of replication and a portion of the ampicillin resistance-conferring gene was isolated and prepared for ligation in substantial accordance with the procedure of Example 6. In a separate reaction, about 10 ug of plasmid pL47 DNA were digested with restriction enzymes EcoRI and BamHI in 200 ul of high-salt buffer at 37° C. for two hours, and the ~1.03 kb EcoRI-BamHI restriction fragment that comprised the novel transcriptional and translational activating sequence and the EK-BGH-encoding DNA was isolated and prepared for ligation in substantial accordance with the procedure of Example 6. The ~2 ug of the ~1.03 kb EcoRI-BamHI restriction fragment obtained were used in the construction of plasmid pL110.

The ~2.7 kb PstI-BamHI and ~1.03 kb EcoRI-BamHI restriction fragments of plasmid pL47 were ligated to the ~2.9 kb PstI-EcoRI restriction fragment of plasmid pPR12AR1 to construct plasmid pL110, and the ligated DNA was used to transform *E. coli* K12 RV308 in substantial accordance with the procedure of Examples 2 and 3, except that tetracycline resistance, not ampicillin resistance, was used as the basis for selecting transformants.

Two PstI restriction enzyme recognition sites are present in the EK-BGH coding region that are not depicted in the restriction site and function maps presented in the accompanying drawings. A restriction site and function map of plasmid pL110 is presented in FIG. 4 of the accompanying drawings.

EXAMPLE 10

Preparation of BK Virus DNA

BK virus is obtained from the American Type Culture Collection under the accession number ATCC VR-837. The virus is delivered in freeze-dried form and resuspended in Hank's balanced salts (Gibco, 3175 Staley Road, Grand Island, N.Y. 14072) to a titer of about $10^5$ plaque-forming units (pfu)/ml. The host of choice for the preparation of BK virus DNA is primary human embryonic kidney (PHEK) cells, which can be obtained from Flow Laboratories, Inc., 7655 Old Springhouse Road, McLean, Va. 22101, under catalogue number 0-100 or from M.A. Bioproducts under catalogue number 70-151.

About five 75 mm$^2$ polystyrene flasks comprising confluent monolayers of about $10^6$ PHEK cells are used to prepare the virus. About 1 ml of BK virus at a titer of $10^5$ pfu/ml is added to each flask, which is then incubated at 37° C. for one hour, and then, fresh culture medium (Dulbecco's Modified Eagle's Medium, Gibco, supplemented with 10% fetal bovine serum) is added, and the infected cells are incubated at 37° C. for 10–14 days or until the full cytopathogenic effect of the virus is noted. This cytopathogenic effect varies from cell line to cell line and from virus to virus but usually consists of cells rounding up, clumping, and sloughing off the culture disk.

The virus is released from the cells by three freeze-thaw cycles, and the cellular debris is removed by centrifugation at 5000×g. The virus in 1 liter of supernatant fluid is precipitated and collected by the addition of 100 g of PEG-6000, incubation of the solution for 24 hours at 4° C., and centrifugation at 5000 Xg for 20 minutes. The pellet is dissolved in 0.1X SSC buffer (1 XSSC=0.15M NaCl and 0.015M NaCitrate, pH=7) at 1/100th of the original volume. The virus suspension is layered onto a 15 ml solution of saturated KBr in a tube, which is centrifuged at 75,000×g for 3 hours. Two bands are evident in the KBr solution after centrifugation. The lower band, which contains the complete virion, is collected and desalted on a Sephadex ® G-50 column (Sigma Chemical Co., P.O. Box 14508, St. Louis, Mo. 63178) using TE (10 mM Tris-HCl, pH=7.8, and 1 mM EDTA) as an elution buffer.

Sodium dodecyl sulfate (SDS) is added to the solution of purified virions obtained from the column to a concentration of 1%; pronase is added to a concentration of 100 μg/ml, and the solution is incubated at 37° C. for 2 hours. Cesium chloride is then added to the solution to a density of 1.56 g/ml, and ethidium bromide is added to the solution to a final concentration of 100 μg/ml. The solution is centrifuged in a Sorvall (DuPont Inst. Products, Biomedical Division, Newton, Conn. 06470) 865 rotor or similar vertical rotor at 260,000 Xg for 24 hours. After centrifugation, the band of virus DNA is isolated and extracted five times with isoamyl alcohol saturated with 100 mM Tris-HCl, pH=7.8. The solution of BK virus DNA is then dialyzed against TE buffer until the 260 nm/280 nm absorbance ratio of the DNA is between 1.75 and 1.90. The DNA is precipitated by adjusting the NaCl concentration to 0.15M, adding two volumes of ethanol, incubating the solution at −70° C. for at least 2 hours, and centrifuging the solution at 12,000×g for 10 minutes. The resulting pellet of BK virus DNA is suspended in TE buffer at a concentration of 1 mg/ml. A restriction site and function map of the BK virus is presented in FIG. 5 of the accompanying drawings.

EXAMPLE 11

Construction of Plasmids pBKneo1 and pBKneo2

*E. coli* K12 HB101/pdBPV-MMTneo cells are obtained in lyophil form from the American Type Culture Collection under the accession number ATCC 37224. The lyophilized cells are plated on L-agar plates containing 100 μg/ml ampicillin and incubated at 37° C. to obtain single colony isolates.

One liter of L broth (10 g tryptone, 10 g NaCl, and 5 g yeast extract per liter) containing 50 μg/ml ampicillin was inoculated with a colony of *E. coli* K12 HB101/pdBPV-MMTneo and incubated in an airshaker at 37° C. until the O.D.$_{590}$ was ~1 absorbance unit, at which time 150 mg of chloramphenicol were added to the culture. The incubation was continued for about 16 hours; the chloramphenicol addition inhibits protein synthesis, and thus inhibits further cell division, but allows plasmid replication to continue.

Plasmid DNA was then isolated from this culture in substantial accordance with the teaching of Example 1 and the ~1 mg of plasmid pdBPV-MMTneo DNA obtained by this procedure was suspended in 1 ml of TE buffer and stored at −20° C.

About 5 μg (5 μl) of the plasmid pdBPV-MMTneo DNA prepared above and five μg (5 μl) of the BK virus DNA prepared in Example 10 were each digested at 37° C. for 2 hours in a solution containing 2 μl of 10X BamHI buffer (1.5M NaCl; 60 mM Tris-HCl, pH=7.9; 60 mM MgCl$_2$; and 1 mg/ml BSA), 1 μl of restriction enzyme BamHI, and 7 μl of H$_2$O. The reaction was stopped by an extraction with an equal volume of phenol, followed by two extractions with chloroform. Each BamHI-digested DNA was then precipitated, collected by centrifugation, and resuspended in 5 μl of H$_2$O.

About 1 μl of 10X ligase buffer was added to a mixture of BamHI-digested plasmid pdBPV-MMTneo (1 μl) and BamHI-digested BK virus DNA (1 μl). After 1 μl (~1000 units) of T4 DNA ligase and 6 μl of H$_2$O were added to the mixture of DNA, the resulting reaction was incubated at 16° C. overnight. The ligated DNA constituted the desired plasmids pBKneo1 and pBKneo2, which differ only with respect to the orientation of the BK virus DNA. Plasmid pBKneo1 contains an ~2.1 kb SalI-HindIII restriction fragment.

*E. coli* K12 HB101 cells are available in lyophilized form from the Northern Regional Research Laboratory under the accession number NRRL B-15626. *E. coli* K12 HB101 cells were cultured, made competent for transformation, and transformed with the ligated DNA prepared above in substantial accordance with the procedure of Example 3. The transformed cells were plated on L-agar plates containing 100 μg/ml ampicillin. *E. coli* K12 HB101/pBKneo1 and *E. coli* K12/pBKneo2 transformants were identified by their ampicillin-resistant phenotype and by restriction enzyme analysis of their plasmid DNA. A restriction site and function map of plasmid pBKneo1 is presented in FIG. 5 of the accompanying drawings.

EXAMPLE 12

Construction of Plasmid pBLcat

A. Construction of Intermediate Plasmid pLPcat

The virion DNA of adenovirus 2 (Ad2) is a double-stranded linear molecule about 35.94 kb in size. The Ad2 late promoter can be isolated on an ~0.316 kb AccI-PvuII restriction fragment of the Ad2 genome; this ~0.32 kb restriction fragment corresponds to the sequence between nucleotide positions 5755 and 6071 of the Ad2 genome. To isolate the desired ~0.32 kb AccI-PvuII restriction fragment, Ad2 DNA is first digested with restriction enzyme BalI, and the ~2.4 kb BalI restriction fragment that comprises the entire sequence of the ~0.32 kb AccI-PvuII restriction fragment is isolated. Then, the ~2.4 kb BalI restriction fragment is digested with AccI and PvuII to obtain the desired fragment.

About 50 μg of Ad2 DNA (available from BRL or ATCC VR-2) are dissolved in 80 μl of H$_2$O and 10 μl of 10X BalI buffer (100 mM Tris-HCl, pH=7.6; 120 mM MgCl$_2$; 100 mM DTT; and 1 mg/ml BSA). About 10 μl (~20 units) of restriction enzyme BalI are added to the solution of Ad2 DNA, and the resulting reaction is incubated at 37° C. for 4 hours.

The BalI-digested DNA is loaded onto an agarose gel and electrophoresed until the restriction fragments are well separated. Visualization of the electrophoresed DNA is accomplished by staining the gel in a dilute solution (0.5 μg/ml) of ethidium bromide and exposing the stained gel to long-wave ultraviolet (UV) light. One method to isolate DNA from agarose is as follows. A small slit is made in the gel in front of the desired fragment, and a small piece of NA-45 DEAE membrane (Schleicher and Schuell, Keene, N.H. 03431) is placed in each slit. Upon further electrophoresis, the DNA non-covalently binds to the DEAE membrane. After the desired fragment is bound to the DEAE membrane, the membrane is removed and rinsed with low-salt buffer (100 mM KCl; 0.1 mM EDTA; and 20 mM Tris-HCl, pH=8). Next, the membrane is placed in a small tube and immersed in high-salt buffer (1M NaCl; 0.1 mM EDTA; and 20 mM Tris-HCl, pH=8) and then incubated at 65° C. for one hour to remove the DNA from the DEAE paper. After the 65° C. incubation, the incubation buffer is collected and the membrane rinsed with high-salt buffer. The high-salt rinse solution is pooled with the high-salt incubation buffer.

The volume of the high salt-DNA solution is adjusted so that the NaCl concentration is 0.25M, and then three volumes of cold, absolute ethanol are added to the solution. The resulting solution is mixed and placed at −70° C. for 10–20 minutes. The solution is then centrifuged at 15,000 rpm for 15 minutes. After another precipitation to remove residual salt, the DNA pellet is rinsed with ethanol, dried, resuspended in 20 μl of TE buffer, and constitutes about 3 μg of the desired restriction fragment of Ad2. The purified fragment obtained is dissolved in 10 μl of TE buffer.

About 6 μl of H$_2$O and 2 μl of 10X AccI buffer (60 mM NaCl; 60 mM Tris-HCl, pH=7.5; 60 mM MgCl$_2$; 60 mM DTT: and 1 mg/ml BSA) are added to the solution of the ~2.4 kb BalI restriction fragment of Ad2. After the addition of about 2 μl (~10 units) of restriction enzyme AccI to the solution of DNA, the reaction is incubated at 37° C. for 2 hours. After the AccI digestion, the DNA is collected by ethanol precipitation and resuspended in 16 μl of H$_2$O and 2 μl of 10X PvuII buffer (600 mM NaCl; 60 mM Tris-HCl, pH=7.5; 60 mM MgCl$_2$; 60 mM DTT; and 1 mg/ml BSA). After the addition of about 2 μl (about 10 units) of restriction enzyme PvuII to the solution of DNA, the reaction is incubated at 37° C. for 2 hours.

The AccI-PvuII-digested, ~2.4 kb BalI restriction fragment of Ad2 is loaded onto an ~6% polyacrylamide gel and electrophoresed until the ~0.32 kb AccI-PvuII restriction fragment that comprises the Ad2 late promoter is separated from the other digestion products. The gel is stained with ethidium bromide and viewed using UV light, and the segment of gel containing the ~0.32 kb AccI-PvuII restriction fragment is cut from the gel, crushed, and soaked overnight at room temperature in ~250 μl of extraction buffer (500 mM NH₄OAc; 10 mM MgOAc; 1 mM EDTA; and 0.1% SDS). The following morning, the mixture is centrifuged, and the pellet is discarded. The DNA in the supernatant is precipitated with ethanol; about 2 μg of tRNA are added to ensure complete precipitation of the desired fragment. About 0.2 μg of the ~0.32 kb AccI-PvuII restriction fragment are obtained and suspended in 7 μl of H₂O.

About 0.25 μg (in 0.5 μl) of BclI linkers (5'-CTGATCAG-3', available from New England Biolabs), which had been kinased in substantial accordance with the procedure described in Example 2 was added to the solution of the ~0.32 kb AccI-PvuII restriction fragment, and then, 1 μl (~1000 units) of T4 DNA ligase and 1 μl of 10X ligase buffer were added to the solution of DNA, and the resulting reaction was incubated at 16° C. overnight. The BclI linkers could only ligate to the PvuII end of the AccI-PvuII restriction fragment. DNA sequencing later revealed that four BclI linkers attached to the PvuII end of the AccI-PvuII restriction fragment. These extra BclI linkers can be removed by BclI digestion and religation; however, the extra BclI linkers were not removed as the linkers do not interfere with the proper functioning of the vectors that comprise the extra linkers.

*E. coli* K12 HB101/pSV2cat cells are obtained in lyophilized form from the ATCC under the accession number ATCC 37155, and plasmid pSV2cat DNA was isolated from the cells in substantial accordance with the procedure of Example 1. About 1 mg of plasmid pSV2cat DNA is obtained and dissolved in 1 ml of TE buffer. About 3 μg (3 μl) of the plasmid pSV2cat DNA were added to 2 μl of 10X AccI buffer and 16 μl of H₂O, and then, 3 μl (about 9 units) of restriction enzyme AccI were added to the solution of pSV2cat DNA, and the resulting reaction was incubated at 37° C. for 2 hours. The AccI-digested plasmid pSV2cat DNA was then digested with restriction enzyme StuI by adding 3 μl of 10X StuI buffer (1.0M NaCl; 100 mM Tris-HCl, pH=8.0; 100 mM MgCl₂; 60 mM DTT; and 1 mg/ml BSA), 5 μl of H₂O, and about 2 μl (about 10 units) of restriction enzyme StuI. The resulting reaction was incubated at 37° C. for 2 hours. The reaction was terminated by extracting the reaction mixture once with phenol, then twice with chloroform. About 0.5 μg of the desired fragment was obtained and dissolved in 20 μl of TE buffer.

About 4 μl of the AccI-StuI-digested plasmid pSV2cat DNA were mixed with about 7 μl of the ~0.32 kb AccI-PvuII (with BclI linkers attached) restriction fragment of Ad2, and after the addition of 3 μl of 10X ligase buffer, 15 μl of H₂O, and 2 μl (about 1000 units) of T4 DNA ligase, the ligation reaction was incubated at 16° C. overnight. The ligated DNA constituted the desired plasmid pLPcat, a plasmid that comprises the Ad2 late promoter positioned so as to drive transcription, and thus expression, of the chloramphenicol acetyltransferase gene. A restriction site and function map of plasmid pLPcat is presented in FIG. 6 of the accompanying drawings.

The ligated DNA was used to transform *E. coli* K12 HB101 cells in substantial accordance with the procedure of Example 3. The transformed cells were plated on L agar containing 50 μg/ml ampicillin; restriction enzyme analysis of plasmid DNA was used to identify the *E. coli* K12 HB101/pLPcat transformants. Plasmid pLPcat DNA was isolated from the transformants for use in subsequent constructions in substantial accordance with the plasmid isolation procedure described in Example 1.

B. Final Construction of Plasmid pBLcat

About 88 μg of plasmid pBKneo1 DNA in 50 μl of TE buffer were added to 7.5 μl of 10X AccI buffer, 30 μl of H₂O, and 15 μl (about 75 units) of restriction enzyme AccI, and the resulting reaction was incubated at 37° C. for 2 hours. The AccI-digested BK virus DNA was loaded on an agarose gel, and the ~1.4 kb fragment that contains the BK enhancer was separated from the other digestion products. The ~1.4 kb AccI restriction fragment was then isolated in substantial accordance with the procedure described in Example 12A. About 5 μg of the fragment were resuspended in 5 μl of 10X PvuII buffer, 45 μl of H₂O, and 5 μl (about 25 units) of restriction enzyme PvuII, and the resulting reaction was incubated at 37° C. for 2 hours. The PvuII-digested DNA was then isolated and prepared for ligation in substantial accordance with the procedure of Example 12A. About 2 μg of the desired ~1.28 kb AccI-PvuII fragment were obtained and dissolved in 5 μl of TE buffer.

About 1 μg of plasmid pLPcat DNA was dissolved in 5 μl of 10X AccI buffer and 40 μl of H₂O.

About 5 μl (~25 units) of restriction enzyme AccI were added to the solution of plasmid pLPcat DNA, and the resulting reaction was incubated at 37° C. The AccI-digested plasmid pLPcat DNA was precipitated with ethanol and resuspended in 5 μl of 10X StuI buffer, 40 μl of H₂O, and 5 μl (about 25 units) of restriction enzyme StuI, and the resulting reaction was incubated at 37° C. for 2 hours. The AccI-StuI-digested plasmid pLPcat DNA was precipitated with ethanol several times to purify the ~4.81 kb AccI-StuI restriction fragment that comprises the *E. coli* origin of replication and Ad2 late promoter away from the other digestion product, a restriction fragment about 16 bp in size. About 1 μg of the desired ~4.81 kb restriction fragment was obtained and dissolved in 20 μl of TE buffer.

The 5 μl of ~4.81 kb AccI-StuI restriction fragment of plasmid pLPcat were added to 5 μl of ~1.28 kb AccI-PvuII restriction fragment of BK virus. After the addition of 3 μl of 10X ligase buffer, 15 μl of H₂O, and 2 μl (about 1000 units) of T4 DNA ligase to the mixture of DNA, the resulting ligation reaction was incubated at 16° C. overnight. The ligated DNA constituted the desired plasmid pBLcat. A restriction site and function map of plasmid pBLcat is presented in FIG. 6 of the accompanying drawings.

The ligated DNA was used to transform *E. coli* K12 HB101 cells in substantial accordance with the procedure described in Example 3. *E. coli* K12 HB101/pBLcat transformants were identified by restriction enzyme analysis of their plasmid DNA. Plasmid pBLcat DNA was prepared for use in subsequent constructions in substantial accordance with the procedure of Example 1.

EXAMPLE 13

Construction of Plasmid pL133

A. Construction of Intermediate Plasmid pSV2-HPC8

Plasmid pHC7 comprises a DNA sequence that encodes human protein C. One liter of L-broth containing 15 μg/ml tetracycline was inoculated with a culture of *E. coli* K12 RRI/pHC7 (NRRL B-15926), and plasmid pHC7 DNA was isolated and purified in substantial accordance with the procedure of Example 1. A restriction site and function map of plasmid pHC7 is presented in FIG. 7 of the accompanying drawings. About 1 mg of plasmid pHC7 DNA was obtained by this procedure, suspended in 1 ml of TE buffer, and stored at −20° C.

Fifty μl of the plasmid pHC7 DNA were mixed with 5 μl (~50 units) of restriction enzyme BanI, 10 μl of 10X BanI reaction buffer (1.5M NaCl; 60 mM Tris-HCl, pH=7.9; 60 mM MgCl₂; and 1 mg/ml BSA), and 35 μl of H₂O and incubated until the digestion was complete. The BanI-digested plasmid pHC7 DNA was then electrophoresed on a 3.5% polyacrylamide gel (29:1, acrylamide:bisacrylamide), until the ~1.25 kb BanI restriction fragment was separated from the other digestion products.

The region of the gel containing the ~1.25 kb BanI restriction fragment was cut from the gel, placed in a test tube, and broken into small fragments. One ml of extraction buffer (500 mM NH₄OAc, 10 mM MgOAc, 1 mM EDTA, 1% SDS, and 10 mg/ml tRNA) was added to the tube containing the fragments, and the tube was placed at 37° C. overnight. Centrifugation was used to pellet the debris, and the supernatant was transferred to a new tube. The debris was washed once with 200 μl of extraction buffer; the wash supernatant was combined with the first supernatant from the overnight extraction. After passing the supernatant through a plug of glass wool, two volumes of ethanol were added to and mixed with the supernatant. The resulting solution was placed in a dry ice-ethanol bath for ~10 minutes, and then, the DNA was pelleted by centrifugation.

Approximately 8 μg of the ~1.25 kb BanI restriction fragment were obtained by this procedure. The purified fragment was suspended in 10 μl of TE buffer and stored at −20° C. The BanI restriction fragment had to be modified by the addition of a linker to construct plasmid pSV2-HPC8.

Five hundred picomoles of each single strand of the linker were kinased in 20 μl of reaction buffer, which contained 15 units (~0.5 μl) T4 polynucleotide kinase, 2 μl 10X ligase buffer, 10 μl of 500 μM ATP, and 7.5 μl of H₂O. The kinase reaction was incubated at 37° C. for 30 minutes, and the reaction was terminated by incubation at 100° C. for 10 minutes. In order to ensure complete kination, the reaction was chilled on ice, 2 μl of 0.2 M dithiothreitol, 2.5 μl of 5 mM ATP, and 15 units of T4 polynucleotide kinase were added to the reaction mixture and mixed, and the reaction mixture was incubated another 30 minutes at 37° C. The reaction was stopped by another 10 minute incubation at 100° C. and then chilled on ice.

Although kinased separately, the two single strands of the DNA linker were mixed together after the kinase reaction. To anneal the strands, the kinase reaction mixture was incubated at 100° C. for 10 minutes in a water bath containing ~150 ml of water. After this incubation, the water bath was shut off and allowed to cool to room temperature, a process taking about 3 hours. The water bath, still containing the tube of kinased DNA, was then incubated at 4° C. overnight. This process annealed the single strands. The linker constructed had the following structure:

The linker was stored at −20° C. until use.

The ~8 μg of ~1.25 kb BanI fragment were added to and mixed with the ~50 μl of linker (~500 picomoles), 1 μl of T4 DNA ligase (~500 units), 10 μl of 10X ligase buffer, and 29 μl of H₂O, and the resulting ligation reaction was incubated at 4° C. overnight. The ligation reaction was stopped by a 10 minute incubation at 65° C. The DNA was pelleted by adding NaOAc to a final concentration of 0.3M, adding 2 volumes of ethanol, chilling in a dry ice-ethanol bath, and then centrifuging the solution.

The DNA pellet was dissolved in 10 μl of 10X ApaI reaction buffer (60 mM NaCl; 60 mM Tris-HCl, pH=7.4; 60 mM MgCl₂; and 60 mM 2-mercaptoethanol), 5 μl ~50 units) of restriction enzyme ApaI, and 85 μl of H₂O, and the reaction was placed at 37° C. for two hours. The reaction was then stopped and the DNA pelleted as above. The DNA pellet was dissolved in 10 μl of 10X HindIII reaction buffer, 5 μl (~50 units) of restriction enzyme HindIII, and 85 μl of H₂O, and the reaction was placed at 37° C. for two hours. After the HindIII digestion, the reaction mixture was loaded onto a 3.5% polyacrylamide gel, and the desired ~1.23 kb HindIII-ApaI restriction fragment was isolated in substantial accordance with the procedure described in Example 12A. Approximately 5 μg of the desired fragment were obtained, suspended in 10 μl of TE buffer, and stored at −20° C.

Fifty μl of plasmid pHC7 DNA were mixed with 5 μl (~50 units) of restriction enzyme PstI, 10 μl of 10X PstI reaction buffer (1.0M NaCl; 100 mM Tris-HCl, pH=7.5; 100 mM MgCl₂; and 1 mg/ml BSA), and 35 μl of H₂O and incubated at 37° C. for two hours. The PstI-digested plasmid pHC7 DNA was then electrophoresed on a 3.5% polyacrylamide gel, and the desired ~0.88 kb fragment was purified in substantial accordance with the procedure described above. Approximately 5 μg of the desired fragment were obtained, suspended in 10 μl of TE buffer, and stored at −20° C.

The ~5 μg of ~0.88 kb PstI fragment were added to and mixed with ~50 μl of the following linker, which was constructed on an automated DNA synthesizer:

About 1 μl of T4 DNA ligase (~10 units), 10 μl 10X ligase buffer, and 29 μl H₂O were added to the mixture of DNA, and the resulting ligation reaction was incubated at 4° C. overnight.

The ligation reaction was stopped by a 10 minute incubation at 65° C. After precipitation of the ligated DNA, the DNA pellet was dissolved in 10 μl of 10X ApaI reaction buffer, 5 μl (~50 units) of restriction enzyme ApaI, and 85 μl of H₂O, and the reaction was placed at 37° for two hours. The reaction was then stopped and the DNA pelleted once again. The DNA pellet was dissolved in 10 μl 10X BglII reaction buffer (1M NaCl; 100 mM Tris-HCl, pH=7.4; 100 mM MgCl₂; 100 mM 2-mercaptoethanol; and 1 mg/ml BSA), 5 μl (~50 units) of restriction enzyme BglII, and 85 1 μll H₂O, and the reaction was placed at 37° C. for two hours. After the BglII digestion, the reaction mixture was loaded onto a 3.5% polyacrylamide gel, and the desired ~0.19 kb ApaI-BglII restriction fragment was isolated in substantial accordance with the procedure described above. Approximately 1 μg of the desired fragment was obtained, suspended in 10 μl of TE buffer, and stored at −20° C.

Approximately 10 μg of plasmid pSV2gpt DNA (ATCC 37145) were dissolved in 10 μl of 10X HindIII reaction buffer, 5 μl (∼50 units) of restriction enzyme HindIII, and 85 μl of H₂O, and the reaction was placed at 37° C. for 2 hours. The reaction mixture was then made 0.25 M in NaOAc, and after the addition of two volumes of ethanol and incubation in a dry ice-ethanol bath, the DNA was pelleted by centrifugation. The DNA pellet was dissolved in 10 μl of 10X BglII buffer, 5 μl (∼50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The gel was stained with ethidium bromide and viewed under ultraviolet light, and the band containing the desired ∼5.1 kb HindIII-BglII fragment was cut from the gel and placed in dialysis tubing, and electrophoresis was continued until the DNA was out of the agarose. The buffer containing the DNA from the dialysis tubing was extracted with phenol and CHCl₃, and then, the DNA was precipitated. The pellet was resuspended in 10 μl of TE buffer and constituted ∼5 μg of the desired ∼5.1 kb HindIII-BglII restriction fragment of plasmid pSV2gpt.

Two μl of the ∼1.23 kb HindIII-ApaI restriction fragment, 3 μl of the ∼0.19 kb ApaI-BglII fragment, and 2 μl of the ∼5.1 kb HindIII-BglII fragment were mixed together and then incubated with 10 μl of 10X ligase buffer, 1 μl of T4 DNA ligase (∼500 units), and 82 μl of H₂O at 16° C. overnight. The ligated DNA constituted the desired plasmid pSV2-HPC8. A restriction site and function map of plasmid pSV2-HPC8 is presented in FIG. 7 of the accompanying drawings.

*E. coli* K12 RRI (NRRL B-15210) cells were made competent for transformation in substantial accordance with the procedure described in Example 3. The ligated DNA prepared above was used to transform the cells, and aliquots of the transformation mix were plated on L-agar plates containing 100 μg/ml ampicillin. The plates were then incubated at 37° C. *E. coli* K12 RRI/pSV2-HPC8 transformants were verified by restriction enzyme analysis of their plasmid DNA.

B. Final Construction of Plasmid pL133

Fifty μg of plasmid pSV2-HPC8 were dissolved in 10 μl of 10X HindIII reaction buffer, 5 μl (18 50 units) of restriction enzyme HindIII, and 85 μl of H₂O, and the reaction was incubated at 37° C. for two hours. After the HindIII digestion, the DNA was precipitated, and the DNA pellet was dissolved in 10 μ; 10X SalI reaction buffer (1.5M NaCl; 60 mM Tris-HCl, pH=7.9; 60 mM MgCl₂; 60 mM 2-mercaptoethanol; and 1 mg/ml BSA), 5 μl (∼50 units) of restriction enzyme SalI, and 85 μl of H₂O. The resulting SalI reaction mxiture was incubated for 2 hours at 37° C. The HindIII-SalI-digested plasmid pSV2-HPC8 was loaded onto a 3.5% polyacrylamide gel and electrophoresed until the desired ∼0.29 kb HindIII-SalI restriction fragment was separated from the other reaction products. The desired fragment was isolated from the gel; about 2 μg of the fragment were obtained and suspended in 10 μl of TE buffer.

Fifty μg of plasmid pSV2-HPC8 were dissolved in 10 μl of 10X BglII reaction buffer, 5 μl (50 units) of restriction enzyme BglII, and 85 μl of H₂O, and the reaction was incubated at 37° C. for two hours. After the BglII digestion, the DNA was precipitated, and the DNA pellet was dissolved in 10 μl of 10X SalI reaction buffer, 5 μl (∼50 units) of restriction enzyme SalI, and 85 μl of H₂O. The resulting SalI reaction mixture was incubated for 2 hours at 37° C. The SalI-BglII-digested plasmid pSV2-HPC8 was loaded onto a 3.5% polyacrylamide gel and electrophoresed until the desired ∼1.15 kb SalI-BglII restriction fragment was separated from the other reaction products. The ∼1.15 kb SalI-BglII restriction fragment was isolated from the gel; about 8 μg of fragment were obtained and suspended in 10 μl of TE buffer.

Approximately 10 μg of plasmid pSV2-β-globin DNA (NRRL B-15928) were dissolved in 10 μl of 10X HindIII reaction buffer, 5 μl (∼50 units) of restriction enzyme HindIII, and 85 μl of H₂O, and the reaction was placed at 37° C. for 2 hours. The reaction mixture was then made 0.25M in NaOAc, and after the addition of two volumes of ethanol and incubation in a dry ice-ethanol bath, the DNA was pelleted by centrifugation. The HindIII-digested plasmid pSV2-β-globin was dissolved in 10 μl of 10X BglII buffer, 5 μl (∼50 units) of restriction enzyme BglII, and 85 μl of H₂O, and the reaction was placed at 37° C. for two hours. After the BglII digestion, the reaction mixture was loaded onto a 1% agarose gel, and the fragments were separated by electrophoresis. The desired ∼4.2 kb HindIII-BglII restriction fragment was isolated from the gel; about 5 μg of the desired fragment were obtained and suspended in 10 μl of TE buffer.

Two μl of the ∼0.29 kb HindIII-SalI fragment of plasmid pSV2-HPC8, 2 μl of the ∼1.15 kb SalI-BglII fragment of plasmid pSV2-HPC8, and 2 μl of the ∼4.2 kb HindIII-BglII fragment of plasmid pSV2-β-globin were mixed together and ligated in substantial accordance with the procedure of Example 13A. The ligated DNA constituted the desired plasmid pL133. A restriction site and function map of plasmid pL133 is presented in FIG. 7 of the accompanying drawings. The desired *E. coli* K12 RRl/pL133 transformants were constructed in substantial accordance with the teaching of Example 16A, with the exception that plasmid pL133, rather than plasmid pSV2-HPC8, was used as the transforming DNA.

EXAMPLE 14

Construction of Plasmid pLPC

About 20 μg of plasmid pBLcat DNA were dissolved in 10 μl of 10X HindIII buffer and 80 μl of H₂O. About 10 μl (∼100 units) of restriction enzyme HindIII were added to the solution of plasmid pBLcat DNA, and the resulting reaction was incubated at 37° C. for 2 hours. The HindIII-digested plasmid pBLcat DNA was loaded onto an agarose gel and electrophoresed until the ∼0.87 kb HindIII restriction fragment that comprises the BK enhancer and Ad2 late promoter was separated from the other digestion products; then, the ∼0.87 kb fragment was isolated and prepared for ligation in substantial accordance with the procedure of Example 12A. About 2 μg of the desired fragment were obtained and dissolved in 5 μl of TE buffer.

About 1.5 μg of plasmid pL133 DNA was dissolved in 2 μl of 10X HindIII buffer and 16 μl of H₂O. About 1 μl (∼10 units) of restriction enzyme HindIII was added to the solution of DNA, and the resulting reaction was incubated at 37° C. for 2 hours. The DNA was then diluted to 100 μl with TE buffer and treated with calf-intestinal alkaline phosphatase in substantial accordance with the procedure in Example 7. The HindIII-digested plasmid pL133 DNA was extracted twice with phenol and once with chloroform, precipitated with ethanol, and resuspended in 10 μl of TE buffer.

About 5 μl of the ~0.87 kb HindIII restriction fragment of plasmid pBLcat were added to the 1.5 μl of HindIII-digested plasmid pL133, and then, 1 μl of 10X ligase buffer, 1 μl (~1000 units) of T4 DNA ligase, and 1.5 μl of H₂O were added to the solution of DNA, and the resulting reaction was incubated at 16° C. overnight. The ligated DNA constituted the desired plasmid pLPC. A restriction site and function map of plasmid pLPC is presented in FIG. 8 of the accompanying drawings.

The ligated DNA was used to transform *E. coli* K12 HB101 in substantial accordance with the procedure of Example 3. The transformed cells were plated on L agar containing ampicillin, and the plasmid DNA of the ampicillin-resistant transformants was examined by restriction enzyme analysis to identify the *E. coli* K12 HB101/pLPC transformants. The ~0.87 kb HindIII restriction fragment that encodes the BK enhancer and Ad2 late promoter could insert into HindIII-digested plasmid pL133 in one of two orientations, only the construction which contains an ~1.0 kb NdeI-StuI fragment yields pLPC.

EXAMPLE 15

Construction of Plasmids pLPChyg1 and pLPChyg2

*E. coli* K12 RR1/pSV2hyg cells are obtained from the Northern Regional Research Laboratory under the accession number NRRL B-18039. Plasmid pSV2hyg DNA is obtained from the cells in substantial accordance with the procedure of Example 1. A restriction site and function map of plasmid pSV2hyg is presented in FIG. 8 of the accompanying drawings.

About 10 μg (in 10 μl of TE buffer) of plasmid pSV2hyg were added to 2 μl of 10X BamHI buffer and 6 μl of H₂O. About 2 μl (about 20 units) of restriction enzyme BamHI were added to the solution of DNA, and the resulting reaction was incubated at 37° C. for 2 hours. The reaction was extracted first with phenol and then was extracted twice with chloroform. The BamHI-digested plasmid pSV2hyg DNA was loaded onto an agarose gel, and the hygromycin resistance gene-containing, ~2.5 kb restriction fragment was isolated in substantial accordance with the procedure described in Example 12A.

About 5 μl of 10X Klenow buffer (0.2 mM in each of the four dNTPs; 0.5 M Tris-HCl, pH=7.8; 50 mM MgCl₂; 0.1M 2-mercaptoethanol; and 100 μg/ml BSA) and 35 μl of H₂O were added to the solution of BamHI-digested plasmid pSV2hyg DNA, and then, about 25 units of Klenow enzyme (about 5 μl, as marketed by BRL) were added to the mixture of DNA, and the resulting reaction was incubated at 16° C. for 30 minutes. The Klenow-treated, BamHI-digested plasmid pSV2hyg DNA was extracted once with phenol and once with chloroform and then precipitated with ethanol. About 2 μg of the desired fragment were obtained and suspended in 5 μl of TE buffer.

About 10 μg (10 μl) of plasmid pLPC DNA were added to 2 μl of 10X StuI buffer and 6 μl of H₂O. About 2 μl (~10 units) of restriction enzyme StuI were added to the solution of DNA, and the resulting reaction was incubated at 37° C. for 2 hours. The StuI-digested plasmid pLPC DNA was precipitated with ethanol, collected by centrifugation, and resuspended in 2 μl of 10X NdeI buffer (1.5M NaCl; 0.1M Tris-HCl, pH=7.8; 70 mM MgCl₂; 60 mM 2-mercaptoethanol; and 1 mg/ml BSA) and 16 μl of H₂O. About 2 μl (~10 units) of restriction enzyme NdeI were added to the solution of StuI-digested DNA, and the resulting reaction was incubated at 37° C. for 2 hours.

The NdeI-StuI-digested plasmid pLPC DNA was precipitated with ethanol, collected by centrifugation, and resuspended in 5 μl of 10X Klenow buffer and 40 μl of H₂O. About 5 μl (~25 units) of Klenow enzyme were added to the solution of DNA, and the resulting reaction was incubated at 16° C. for 30 minutes. After the Klenow reaction, the reaction mixture was loaded onto an agarose gel, and the ~5.82 kb NdeI-StuI restriction fragment was isolated from the gel. About 5 μg of the desired fragment were obtained and suspended in 5 μl of TE buffer.

About 2 μl of the ~2.5 kb Klenow-treated BamHI restriction fragment of plasmid pSV2hyg were mixed with about 1 μl of the ~5.82 kb Klenow-treated NdeI-StuI restriction fragment of plasmid pLPC, and about 3 μl of 10X ligase buffer, 2 μl of T4 DNA ligase (~1000 units), 1 μl of T4 RNA ligase (~1 unit), and 14 μl of H₂O were added to the solution of DNA. The resulting reaction was incubated at 16° C. overnight. The ligated DNA constituted the desired plasmids pLPChyg1 and pLPChyg2, which differ only with respect to the orientation of the ~2.5 kb Klenow-treated, BamHI restriction fragment of plasmid pSV2hyg. A restriction site and function map of plasmid pLPChyg1 is presented in FIG. 8 of the accompanying drawings. The ligated DNA was used to transform *E. coli* K12 HB101 in substantial accordance with the procedure of Example 3. The desired *E. coli* K12 HB101/pLPChyg1 and *E. coli* K12 HB101/pLPChyg2 transformants were plated on L agar containing ampicillin and identified by restriction enzyme analysis of their plasmid DNA.

EXAMPLE 16

Construction of Plasmid pBW32

A. Construction of Intermediate Plasmid pTPA103

Plasmid pTPA102 comprises the coding sequence of human tissue plasminogen activator (TPA). Plasmid pTPA102 can be isolated from *E. coli* K12 MM294/pTPA102, a strain available from the Northern Regional Research Laboratory under the accession number NRRL B-15834. A restriction site and function map of plasmid pTPA102 is presented in FIG. 9 of the accompanying drawings. Plasmid pTPA102 DNA is isolated from *E. coli* K12 MM294/pTPA102 in substantial accordance with the procedure of Example 1.

About 50 μg of plasmid pTPA102 (in about 50 μl of TE buffer) were added to 10 μl of 10X Tth111I buffer (0.5M NaCl; 80 mM Tris-HCl, pH=7.4; 80 mM MgCl₂; 80 mM 2-mercaptoethanol; and 1 mg/ml BSA) and 80 μl of H₂O. About 10 μl (~50 units) of restriction enzyme Tth111I were added to the solution of DNA, and the resulting reaction was incubated at 65° C. for 2 hours. The reaction mixture was loaded onto an agarose gel, and the ~4.4 kb Tth111I restriction fragment that comprises the TPA coding sequence was isolated from the gel. The other digestion products, 3.1 kb and 0.5 kb restriction fragments, were discarded. About 10 μg of the desired ~4.4 kb Tth111I restriction fragment were obtained and suspended in 10 μl of TE buffer.

About 5 μl of 10X Klenow buffer and 30 μl of H₂O were added to the solution comprising the ~4.4 kb Tth111I restriction fragment, and after the further addition of about 5 μl of Klenow enzyme (~5 units), the reaction mixture was incubated at 16° C. for 30 minutes. After the Klenow reaction, the DNA was precipitated with ethanol and resuspended in 3 μl of 10X ligase buffer and 14 μl of H₂O.

BamHI linkers (New England Biolabs), which had the following sequence:

were kinased and prepared for ligation by the following procedure. Four μl of linkers (~2 μg) were dissolved in 20.15 μl of H₂O and 5 μl of 10X kinase buffer (500 mM Tris-HCl, pH=7.6 and 100 mM MgCl₂), incubated at 90° C. for two minutes, and then cooled to room temperature. Five μl of γ-³²P-ATP (~20 μCi), 2.5 μl of 1M DTT, and 5 μl of polynucleotide kinase (~10 units) were added to the mixture, which was then incubated at 37° C. for 30 minutes. Then, 3.35 μl of 0.01M ATP and 5 μl of kinase were added, and the reaction was continued for another 30 minutes at 37° C. The radioactive ATP aids in determining whether the linkers have ligated to the target DNA.

About 10 μl of the kinased BamHI linkers were added to the solution of ~4.4 kb Tth111I restriction fragment, and after the addition of 2 μl of T4 DNA ligase (~1000 units) and 1 μl of T4 RNA ligase (~2 units), the ligation reaction was incubated overnight at 4° C. The ligated DNA was precipitated with ethanol and resuspended in 5 μl of 10X HindIII buffer and 40 μl of H₂O. About 5 μl (~50 units) of restriction enzyme HindIII were added to the solution of DNA, and the resulting reaction was incubated at 37° C. for 2 hours.

The HindIII-digested DNA was precipitated with ethanol and resuspended in 10 μl of 10X BamHI buffer and 90 μl of H₂O. About 10 μl (~100 units) of restriction enzyme BamHI were added to the solution of DNA, and the resulting reaction was incubated at 37° C. for 2 hours. After the BamHI digestion, the reaction mixture was loaded onto an agarose gel, and the ~2.0 kb BamHI-HindIII restriction fragment was isolated from the gel. About 4 μg of the desired fragment were obtained and suspended in about 5 μl of TE buffer.

To construct plasmid pTPA103, the ~2.0 kb BamHI-HindIII restriction fragment derived from plasmid pTPA102 was inserted into BamHI-HindIII-digested plasmid pRC. Plasmid pRC was constructed by inserting an ~288 bp EcoRI-ClaI restriction fragment that comprises the promoter and operator (trpPO) sequences of the E. coli trp operon into EcoRI-ClaI-digested plasmid pKC7. Plasmid pKC7 can be obtained from the American Type Culture Collection in E. coli K12 N100/pKC7 under the accession number ATCC 37084. The ~288 bp EcoRI-ClaI restriction fragment that comprises the trpPO can be isolated from plasmid pTPA102, which can be isolated from E. coli K12 MM294/pTPA102 (NRRL B-15834). Plasmid pKC7 and plasmid pTPA102 DNA can be obtained from the aforementioned cell lines in substantial accordance with the procedure of Example 1. This ~0.29 kb EcoRI-ClaI restriction fragment of plasmid pTPA102 comprises the transcription activating sequence and most of the translation activating sequence of the E. coli trp gene and has the sequence depicted below:

Thus, to construct plasmid pRC, about 2 μg of plasmid pKC7 in 10 μl of TE buffer were added to 2 μl of 10X ClaI buffer (0.5M NaCl; 60 mM Tris-HCl, pH=7.9, 60 mM MgCl₂; and 1 mg/ml BSA) and 6 μl of H₂O. About 2 μl (~10 units) of restriction enzyme ClaI were added to the solution of plasmid pKC7 DNA, and the resulting reaction was incubated at 37° C. for 2 hours. The ClaI-digested plasmid pKC7 DNA was precipitated with ethanol and resuspended in 2 μl of 10X EcoRI buffer and 16 μl of H₂O. About 2 μl (~10 units) of restriction enzyme EcoRI were added to the solution of ClaI-digested plasmid pKC7 DNA, and the resulting reaction was incubated at 37° C. for 2 hours.

The EcoRI-ClaI-digested plasmid pKC7 DNA was extracted once with phenol and then twice with chloroform. The DNA was then precipitated with ethanol and resuspended in 3 μl of 10X ligase buffer and 20 μl of H₂O. A restriction site and function map of plasmid pKC7 can be obtained from Maniatis et al., Molecular Cloning (Cold Spring Harbor Laboratory, 1982), page 8.

About 20 μg of plasmid pTPA102 in about 20 μl of TE buffer were added to 10 μl of 10X ClaI buffer and 60 μl of H₂O. About 10 μl (~50 units) of restriction enzyme ClaI were added to the solution of plasmid pTPA102 DNA, and the resulting reaction was incubated at 37° C. for 2 hours. The ClaI-digested plasmid pTPA102 DNA was precipitated with ethanol and resuspended in 10 μl of 10X EcoRI buffer and 80 μl of H2O. About 10 μl (~50 units) of restriction enzyme EcoRI were added to the solution of ClaI-digested plasmid pTPA102 DNA, and the resulting reaction was incubated at 37° C. for 2 hours.

The EcoRI-ClaI-digested plasmid pTPA102 DNA was extracted once with phenol, loaded onto a 7% polyacrylamide gel, and electrophoresed until the ~288 bp EcoRI-ClaI restriction fragment that comprises the trpPO was separated from the other digestion products. The ~288 bp EcoRI-ClaI restriction fragment was isolated from the gel; about 1 μg of the desired fragment was obtained, suspended in 5 μl of TE buffer, and added to the solution of EcoRI-ClaI-digested plasmid pKC7 DNA prepared as described above. About 2 μl (~1000 units) of T4 DNA ligase were then added to the mixture of DNA, and the resulting ligation reaction was incubated at 16° C. for 2 hours. The ligated DNA constituted the desired plasmid pRC DNA.

The ligated DNA was used to transform *E. coli* K12 HB101 competent cells in substantial accordance with the procedure of Example 3. The transformed cells were plated on L agar containing 100 μg/ml ampicillin, and the ampicillin-resistant transformants were screened by restriction enzyme analysis of their plasmid DNA to identify the desired *E. coli* K12 HB101/pRC colonies. Plasmid pRC DNA was obtained from the *E. coli* K12 HB101/pRC transformants in substantial accordance with the procedure of Example 1.

About 2 μg of plasmid pRC DNA in 2 μl of TE buffer were added to 2 μl of 10X HindIII buffer and 16 μl of H2O. About 2 μl (~10 units) of restriction enzyme HindIII were added to the solution of plasmid pRC DNA, and the resulting reaction was incubated at 37° C. for two hours. The HindIII-digested plasmid pRC DNA was precipitated with ethanol and resuspended in 2 μl of 10X BamHI buffer and 16 μl of H2O. About 2 μl (~10 units) of restriction enzyme BamHI were added to the solution of HindIII-digested plasmid pRC DNA, and the resulting reaction was incubated at 37° C. for 2 hours.

The BamHI-HindIII-digested plasmid pRC DNA was extracted once with phenol and then twice with chloroform. The DNA was precipitated with ethanol and resuspended in 3 μl of 10X ligase buffer and 20 μl of H2O. The ~4 μg (in ~5 μl of TE buffer) of ~2.0 kb HindIII-BamHI restriction fragment of plasmid pTPA102 were then added to the solution of BamHI-HindIII-digested plasmid pRC DNA. About 2 μl (~1000 units) of T4 DNA ligase were added to the mixture of DNA, and the resulting reaction was incubated at 16° C. for 2 hours. The ligated DNA constituted the desired plasmid pTPA103 DNA.

To reduce undesired transformants, the ligated DNA was digested with restriction enzyme NcoI, which cuts plasmid pRC but not plasmid pTPA103. Thus, digestion of the ligated DNA with NcoI reduces undesired transformants, because linearized DNA transforms *E. coli* at a lower frequency than closed, circular DNA. To digest the ligated DNA, the DNA was first precipitated with ethanol and then resuspended in 2 μl of 10X NcoI buffer (1.5 M NaCl; 60 mM Tris-HCl, pH=7.8; 60 mM (~10 units) of restriction enzyme NcoI were added to the solution of DNA, and the resulting reaction was incubated at 37° C. for 2 hours.

The ligated and then NcoI-digested DNA was used to transform *E. coli* K12 RV308 (NRRL B-15624). *E. coli* K12 RV308 cells were made competent and transformed in substantial accordance with the procedure of Example 3. The transformation mixture was plated on L agar containing 100 μg/ml ampicillin. The ampicillin-resistant transformants were tested for sensitivity to kanamycin, for though plasmid pRC confers kanamycin resistance, plasmid pTPA103 does not. The ampicillin-resistant, kanamycin-sensitive transformants were then used to prepare plasmid DNA, and the plasmid DNA was examined by restriction enzyme analysis to identify the *E. coli* K12 RV308/pTPA103 transformants. A restriction site and function map of plasmid pTPA103 is presented in FIG. 9 of the accompanying drawings. Plasmid pTPA103 DNA was isolated from the *E. coli* K12 RV308/pTPA103 cells in substantial accordance with the procedure of Example 1.

B. Construction of Intermediate Plasmid pBW25

About 1 μg of plasmid pTPA103 DNA in 1 μl of TE buffer was added to 2 μl of 10X BglII buffer and 16 μl of H2O. About 1 μl (~5 units) of restriction enzyme BglII was added to the solution of plasmid pTPA103 DNA, and the resulting reaction was incubated at 37° C. for 2 hours. The BglII-digested plasmid pTPA103 DNA was precipitated with ethanol and resuspended in 5 μl of 10X Klenow buffer and 44 μl of H2O. About 1 μl of Klenow enzyme (~1 unit) was added to the solution of BglII-digested plasmid pTPA103 DNA, and the resulting reaction was incubated at 16° C. for 2 hours. The Klenow-treated, BglII-digested plasmid pTPA103 DNA was precipitated with ethanol and resuspended in 3 μl of 10X ligase buffer and 22 μl of H2O.

About 2 μl (0.2 μg) of unkinased NdeI linkers (New England Biolabs) of sequence:

were added to the solution of Klenow-treated, BglII-digested plasmid pTPA103 DNA, together with 2 μl (~1000 units) of T4 DNA ligase and 1 μl (~2 units) of T4 RNA ligase, and the resulting ligation reaction was incubated at 4° C. overnight. The ligated DNA constituted plasmid pTPA103derNdeI, which is substantially similar to plasmid pTPA103, except plasmid pTPA103derNdeI has an NdeI recognition sequence where plasmid pTPA103 has a BglII recognition sequence.

The ligated DNA was used to transform *E. coli* K12 RV308 competent cells in substantial accordance with the procedure described in Example 3. The transformed cells were plated on L-agar containing ampicillin, and the *E. coli* K12 RV308/pTPA103derNdeI transformants were identified by restriction enzyme analysis of their plasmid DNA. Plasmid pTPA103derNdeI DNA was isolated from the transformants for use in subsequent constructions in substantial accordance with the procedure of Example 1.

About 10 μg of plasmid pTPA103derNdeI DNA in 10 μl of TE buffer were added to 2 μl of 10X AvaII buffer (0.6M NaCl; 60 mM Tris-HCl, pH=8.0; 0.1M MgCl2; 60 mM 2-mercaptoethanol; and 1 mg/ml BSA) and 6 μl of H2O. About 2 μl (~10 units) of restriction enzyme AvaII were added to the DNA, and the resulting reaction was incubated at 37° C. for 2 hours. The AvaII-digested DNA was loaded onto an agarose gel and electrophoresed until the ~1.4 kb restriction fragment was separated from the other digestion products. The ~1.4 kb AvaII restriction fragment of plasmid pTPA103derNdeI was isolated from the gel; about 2 μg of the desired fragment were obtained and suspended in 5 μl of TE buffer.

About 5 μl of 10X Klenow buffer, 35 μl of H₂O, and 5 μl (~5 units) of Klenow enzyme were added to the solution of ~1.4 kb AvaII restriction fragment, and the resulting reaction was incubated at 16° C. for thirty minutes. The Klenow-treated DNA was precipitated with ethanol and resuspended in 3 μl of 10X ligase buffer and 14 μl of H₂O.

About 2 μg of HpaI linkers of sequence:

were kinased in substantial accordance with the procedure of Example 2. About 10 μl of the kinased linkers were added to the solution of Klenow-treated, ~1.4 kb AvaII restriction fragment of plasmid pTPA103derNdeI together with 2 μl (~1000 units) of T4 DNA ligase and 1 μl (~1 unit) of T4 RNA ligase, and the resulting reaction was incubated at 16° C. overnight.

The ligated DNA was extracted once with phenol, extracted twice with chloroform, precipitated with ethanol, and resuspended in 2 μl of 10X EcoRI buffer and 16 μl of H₂O. About 2 μl (~10 units) of restriction enzyme EcoRI were added to the solution of DNA, and the resulting reaction was incubated at 37° C. for 2 hours. The EcoRI-digested DNA was extracted once with phenol, extracted twice with chloroform, precipitated with ethanol, and resuspended in 3 μl of 10X ligase buffer and 20 μl of H₂O. The fragment, which is about 770 bp in size and encodes the trpPO and the amino-terminus of TPA, thus prepared had one EcoRI-compatible end and one blunt end and was ligated into EcoRI-SmaI-digested plasmid pUC19 to form plasmid pUC19TPAFE.

About 2 μl of plasmid pUC19 (available from Bethesda Research Laboratories) were dissolved in 2 μl of 10X SmaI buffer (0.2M KCl; 60 mM Tris-HCl, pH=8.0; 60 mM MgCl₂; 60 mM 2-mercaptoethanol; and 1 mg/ml BSA) and 16 μl of H₂O. About 2 μl (~10 units) of restriction enzyme SmaI were added to the solution of DNA, and the resulting reaction was incubated at 25° C. for 2 hours. The SmaI-digested plasmid pUC19 DNA was precipitated with ethanol, collected by centrifugation, and resuspended in 2 μl of 10X EcoRI buffer and 16 μl of H₂O. About 2 μl (~10 units) of restriction enzyme EcoRI were added to the solution of SmaI-digested plasmid pUC19 DNA, and the resulting reaction was incubated at 37° C. for 2 hours. The EcoRI-SmaI-digested plasmid pUC19 DNA was extracted once with phenol, extracted twice with chloroform, and resuspended in 5 μl of TE buffer.

The EcoRI-SmaI-digested plasmid pUC19 DNA was added to the solution containing the ~770 bp EcoRI-blunt end restriction fragment derived from plasmid pTPA103derNdeI. About 2 μl (~1000 units) of T4 DNA ligase were added to the mixture of DNA, and the resulting reaction was incubated at 16° C. overnight. The ligated DNA constituted the desired plasmid pUC19TPAFE. A restriction site and function map of plasmid pUC19TPAFE is presented in FIG. 9 of the accompanying drawings.

The multiple-cloning site of plasmid pUC19, which comprises the EcoRI and SmaI recognition sequences utilized in the construction of plasmid pUC19TPAFE, is located within the coding sequence for the lacZ α fragment. Expression of the lacZ α fragment in cells that contain the lacZ ΔM15 mutation, a mutation in the lacZ gene that encodes β-galactosidase, allows those cells to express a functional β-galactosidase molecule and thus allows those cells to hydrolyze X-Gal (5-bromo-4-chloro-3-indolyl-β-D-galactopyranoside), a colorless compound, to its indigo-colored hydrolysis product. Insertion of DNA into the multiple-cloning site of plasmid pUC19 interrupts the coding sequence for the lacZ α fragment, and cells with the lacZ ΔM15 mutation that host such a plasmid are unable to hydrolyze X-Gal. The ligated DNA that constituted plasmid pUC19TPAFE was used to transform E. coli K12 RR1ΔM15 (NRRL B-15440) cells made competent for transformation in substantial accordance with the procedure of Example 3.

The transformed cells were plated on L agar containing 100 μg/ml ampicillin; 40 μg/ml X-Gal; and 1 mM IPTG. Colonies that failed to exhibit the indigo color were subcultured and used to prepare plasmid DNA; the E. coli K12 RR1ΔM15/pUC19TPAFE transformants were identified by restriction enzyme analysis of their plasmid DNA. Plasmid pUC19TPAFE DNA was isolated from the E. coli K12 RR1ΔM15/pUC19-TPAFE cells for use in subsequent constructions in substantial accordance with the procedure of Example 1.

About 7 μg of plasmid pUC19TPAFE in 20 μl of TE buffer were added to 10 μl of 10X HpaI buffer (0.2M KCl; 0.1M Tris-HCl, pH=7.4; and 0.1M MgCl₂) and 70 μl of H₂O. About 3 μl (~6 units) of restriction enzyme HpaI were added to the solution of plasmid pUC19-TPAFE DNA, and the resulting reaction was incubated at 37° C. for 20 minutes; the short reaction period was designed to yield a partial HpaI digest. The reaction was adjusted to 150 μl of 1X BamHI buffer (150 mM NaCl; 10 mM Tris-HCl, pH=8.0; and 10 mM MgCl₂; raising the salt concentration inactivates HpaI). About 1 μl (~16 units) of restriction enzyme BamHI were added to the solution of partially-HpaI-digested DNA, and the resulting reaction was incubated at 37° C. for 90 minutes.

The BamHI-partially-HpaI-digested plasmid pUC19-TPAFE DNA was concentrated by ethanol precipitation, loaded onto a 1.5% agarose gel, and the ~3.42 kb HpaI-BamHI restriction fragment that comprises the replicon, β-lactamase gene, and all of the TPA-encoding DNA of plasmid pUCATPAFE was isolated from the gel by cutting out the segment of the gel that contained the desired fragment, freezing the segment, and then squeezing the liquid from the segment. The DNA was precipitated from the liquid by an ethanol precipitation. About 1 μg of the desired fragment was obtained and suspended in 20 μl of TE buffer.

About 10 μg of plasmid pTPA103 in 10 μl of TE buffer were dissolved in 10 μl of 10X ScaI buffer (1.0 M NaCl; 60 mM Tris-HCl, pH=7.4; and 60 mM MgCl₂) 10 mM DTT; and 1 mg/ml BSA) and 80 μl of H₂O. About 3 μl (~18 units) of restriction enzyme ScaI were added to the solution of plasmid pTPA103 DNA, and the resulting reaction was incubated at 37° C. for 90 minutes. The reaction volume was adjusted to 150 μl of 1X BamHI buffer, and about 1 μl (~16 units) of restriction enzyme BamHI was added to the mixture, which was then incubated at 37° C. for 90 minutes. The DNA was precipitated with ethanol, collected by centrifugation, and resuspended in preparation for electrophoresis. The ScaI-BamHI-digested plasmid pTPA103 DNA was loaded onto a 1.5% agarose gel and electrophoresed until the ~1.015 kb ScaI-BamHI restriction fragment was separated from the other digestion products. The ~1.015 ScaI-BamHI restriction fragment that comprises the TPA carboxy-terminus-encoding DNA of plasmid pTPA103 was isolated from the gel; about 0.5 μg of the desired fragment were obtained and dissolved in 20 μl of glass-distilled H₂O.

About 2 μl of the ~3.42 kb BamHI-HpaI restriction fragment of plasmid pUC19TPAFE were added to 2 μl of the ~1.015 kb ScaI-BamHI restriction fragment of plasmid pTPA103 together with 2 μl of 10X ligase buffer and 1 μl (~1 Weiss unit; the ligase was obtained from Promega Biotec, 2800 S. Fish Hatchery Road, Madison, Wis. 53711) of T4 DNA ligase, and the resulting reaction was incubated at 16° C. overnight. The ligated DNA constituted the desired plasmid pBW25. A restriction site and function map of plasmid pBW25 is presented in FIG. 9 of the accompanying drawings.

The ligated DNA was used to transform *E. coli* K12 JM105 (available from BRL) that were made competent for transformation in substantial accordance with the procedure of Example 3, except that 50 mM CaCl₂ was used in the procedure. The transformed cells were plated on BHI (Difco Laboratories, Detroit, Mich.) containing 100 μg/ml ampicillin, and the *E. coli* K12 JM105/pBW25 transformants were identified by restriction enzyme analysis of their plasmid DNA. Digestion of plasmid pBW25 with restriction enzyme EcoRI yields ~3.38 kb and ~1.08 kb restriction fragments. Plasmid pBW25 is prepared for use in subsequent constructions in substantial accordance with the procedure of Example 1.

C. Site-Specific Mutagenesis of the TPA Coding Region and Construction of Plasmid pBW28

About 5 μg of plasmid pBW25 in 10 μl of glass-distilled H₂O were added to about 10 μl of 10X HindIII reaction buffer and 80 μl of H₂O. About 1 μl (~20 units) of restriction enzyme HindIII was added to the solution of plasmid pBW25 DNA, and the resulting reaction was incubated at 37° C. for 90 minutes. About 3 μl (~24 units) of restriction enzyme EcoRI and 10 μl of 1M Tris.HCl, pH=7.6, were added to the solution of HindIII-digested plasmid pBW25 DNA, and the resulting reaction was incubated at 37° C. for 90 minutes. The EcoRI-HindIII-digested plasmid pBW25 DNA was concentrated by ethanol precipitation, loaded onto a 1.5% agarose gel, and electrophoresed until the ~810 bp EcoRI-HindIII restriction fragment was separated from the other digestion products. About 0.5 μg of the ~810 bp EcoRI-HindIII restriction fragment was isolated from the gel, prepared for ligation, and resuspended in 20 μl of glass-distilled H₂O.

About 4.5 μg of the replicative form (RF) of M13mp8 DNA (available from New England Biolabs) in 35 μl of glass-distilled H₂O were added to 10 μl of 10X HindIII buffer and 55 μl of H₂O. About 1 μl (~20 units) of restriction enzyme HindIII was added to the solution of M13mp8 DNA, and the resulting reaction was incubated at 37° C. for 1 hour. About 3 μl (~24 units) of restriction enzyme EcoRI and about 10 μl of 1M Tris.HCl, pH=7.6, were added to the solution of HindIII-digested M13mp8 DNA, and the resulting reaction was incubated at 37° C. for 1 hour. The HindIII-EcoRI-digested M13mp8 DNA was collected by ethanol precipitation, resuspended in preparation for agarose gel electrophoresis, and the large restriction fragment isolated by gel electrophoresis. About 1 μg of the large EcoRI-HindIII restriction fragment of M13mp8 was obtained and suspended in 20 μl of glass-distilled H₂O. About 2 μl of the large EcoRI-HindIII restriction fragment of M13mp8, 2 μl of 10X ligase buffer, 12 μl of H₂O and ~1 μl (~1 Weiss unit) of T4 DNA ligase were added to 3 μl of the ~810 bp EcoRI-HindIII restriction fragment of plasmid pBW25, and the resulting ligation reaction was incubated at 16° C. overnight.

*E. coli* JM103 cells, available from BRL, were made competent and transfected with the ligation mix in substantial accordance with the procedure described in the BRL M13 Cloning/'Dideoxy' Sequencing Instruction Manual, except that the amount of DNA used per transfection was varied. Recombinant plaques were identified by insertional inactivation of the β-galactosidase α-fragment-encoding gene, which results in the loss of the ability to cleave X-gal to its indigo-colored cleavage product. For screening purposes, six white plaques were picked into 2.5 ml of L broth, to which was added 0.4 ml of *E. coli* K12 JM103, cultured in minimal media stock to insure retention of the F episome that carries proAB, in logarithmic growth phase. The plaque-containing solutions were incubated in an airshaker at 37° C. for 8 hours. Cells from 1.5 ml aliquots were pelleted and RF DNA isolated in substantial accordance with the alkaline miniscreen procedure of Birnboim and Doly, 1979, Nuc. Acids Res. 7:1513. The remainder of each culture was stored at 4° C. for stock. The desired phage, designated pM8BW26, contained the ~810 bp EcoRI-HindIII restriction fragment of plasmid pBW25 ligated to the ~7.2 kb EcoRI-HindIII restriction fragment of M13mp8.

About fifty ml of log phase *E. coli* JM103 were infected with pM8BW26 and incubated in an air-shaker at 37° C. for 18 hours. The infected cells were pelleted by low speed centrifugation, and single-stranded pM8BW26 DNA was prepared from the culture supernatant by scaling up the procedure given in the Instruction manual. Single-stranded pM8BW26 was mutagenized in substantial accordance with the teaching of Adelman et al., 1983, DNA 2(3): 183-193, except that the Klenow reaction was done at room temperature for 30 minutes, then at 37° C. for 60 minutes, then at 10° C. for 18 hours. In addition, the S1 treatment was done at 20° C., the salt concentration of the buffer was one-half that recommended by the manufacturer, and the M13 sequencing primer (BRL) was used. The synthetic oligodeoxyribonucleotide primer used to delete the coding sequence for amino acid residues 87 through 261 of native TPA was

5'-GGGAAGTGCTGTGAAA

TATCCACCTGCGGCCTGAGA-3'.

The resulting mutagenesis mix was used to transfect *E. coli* K12 JM103 in substantial accordance with the infection procedure described above. Desired mutants were identified by restriction enzyme analysis of RF DNA and by Maxam and Gilbert DNA sequencing. The desired mutant, which had the coding sequence for amino acid residues 87 through 261 of native TPA deleted, was designated pM8BW27.

To construct plasmid pBW28, a variety of DNA fragments are needed. The first of these fragments was obtained by adding ~20 μg of RF pM8BW27 DNA in 20 μl of glass-distilled H₂O to 10 μl of 10X NdeI buffer and 60 μl of H₂O. About 10 μl (~50 units) of restriction enzyme NdeI were added to the mixture of plasmid pM8BW27 DNA, and the resulting reaction was incubated at 37° C. for two hours. The NdeI-digested plasmid pM8BW27 DNA was precipitated with ethanol, collected by centrifugation, and resuspended in 10 μl of 10X EcoRI buffer and 90 μl of H₂O. About 10 μl (~50 units) of restriction enzyme EcoRI were added to the solution of NdeI-digested plasmid pM8BW27 DNA, and the resulting reaction was incubated at 37° C. for 2 hours. The EcoRI-NdeI-digested plasmid pM8BW27 DNA was electrophoresed on an agarose gel until the ~560 bp NdeI-EcoRI restriction fragment, which contains the portion of TPA coding sequence that spans the site of deletion, was separated from the other digestion products. The ~560 bp NdeI-EcoRI restriction fragment was isolated from the gel; about 0.5 μg of the desired fragment was obtained and suspended in 20 μl of glass-distilled H₂O.

The second fragment needed to construct plasmid pBW28 is synthesized one strand at a time on an automated DNA synthesizer. The two complementary strands, which will hybridize to form a double-stranded DNA segment with XbaI and NdeI overlaps, are kinased and annealed in substantial accordance with the procedure of Example 2. The linker has the following structure:

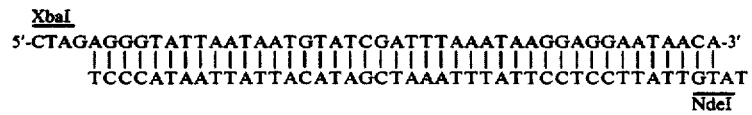

The third fragment needed to construct plasmid pBW28 was prepared by adding ~20 μg of plasmid pTPA103 in 20 μl of TE buffer to 10 μl of 10X BamHI buffer and 60 μl of H₂O. About 10 μl (~50 units) of restriction enzyme BamHI were added to the solution of plasmid pTPA103 DNA, and the resulting reaction was incubated at 37° C. for 2 hours. The BamHI-digested plasmid pTPA103 DNA was precipitated with ethanol, collected by centrifugation, fugation, and resuspended in 10 μl of 10X EcoRI buffer and 80 μl of H₂O. About 10 μl (~50 units) of restriction enzyme EcoRI were added to the solution of BamHI-digested plasmid pTPA103 DNA, and the resulting reaction was incubated at 37° C. for 2 hours. The BamHI-EcoRI-digested plasmid pTPA103 DNA was loaded onto an agarose gel and electrophoresed until the ~689 bp EcoRI-BamHI restriction fragment, which comprises the coding sequence for the carboxy-terminus of TPA, was separated from the other digestion products. About 0.5 μg of the ~689 bp fragment was isolated from the gel and then resuspended in 10 μl of glass-distilled H₂O.

The final fragment necessary to construct plasmid pBW28 was isolated from plasmid pL110, the construction of which was disclosed in Example 9. About 25 μg of plasmid pL110 in 25 μl of TE buffer were added to 10 μl of 10X XbaI buffer (0.5M NaCl; 60 mM Tris-HCl, pH=7.9; 60 mM MgCl₂; and 1 mg/ml BSA) and 55 μl of H₂O. About 10 μl (~50 units) of restriction enzyme XbaI were added to the solution of plasmid pL110 DNA, and the resulting reaction was incubated at 37° C. for 2 hours. The XbaI-digested plasmid pL110 DNA was precipitated with ethanol, collected by centrifugation, and resuspended in 10 μl of 10X BamHI buffer and 89 μl of H₂O. About 1 μl (~5 units) of restriction enzyme BamHI was added to the solution of XbaI-digested plasmid pL110 DNA, and the resulting reaction was incubated at 37° C. for 30 minutes to obtain a partial BamHI digest. The XbaI-partially-BamHI-digested plasmid pL110 DNA was loaded onto an agarose gel and electrophoresed until the ~6.0 kb XbaI-BamHI fragment was clearly separated from the other digestion products. The ~6.0 kb restriction fragment was isolated from the gel; about 0.5 μg of the ~6.0 kb XbaI-BamHI restriction fragment was obtained and suspended in about 40 μl of glass-distilled H₂O. This ~6.0 kb XbaI-BamHI restriction fragment comprises all of plasmid pL110 except the EK-BGH-encoding DNA.

To construct plasmid pBW28, the following fragments are mixed together: about 0.1 μg (~8 μl) of the ~6.0 kb BamHI-XbaI restriction fragment of plasmid pL110; about 0.05 μg (~2 μl) of the ~560 bp NdeI-EcoRI restriction fragment of plasmid pM8BW27; about 0.1 μg (~2 μl) of the ~689 bp EcoRI-BamHI restriction fragment of plasmid pTPA103; and about 0.02 μg (~1 μl) of the ~45 bp XbaI-NdeI synthetic linker. About 2 μl of 10X ligase buffer and 1 μl (~1 Weiss unit) of T4 DNA ligase are added to the mixture of DNA, and the resulting ligation reaction is incubated at 4° C. overnight. The ligated DNA constituted the desired plasmid pBW28. A restriction site and function map of plasmid pBW28 is presented in FIG. 10 of the accompanying drawings.

The ligated DNA was used to transform E. coli K12 MM294 (NRRL B-15625) made competent in substantial accordance with the procedure of Example 3, except that 50 mM CaCl₂ was used in the procedure. Due to the presence of the lambda pL promoter and the gene encoding the temperature-sensitive lambda pL repressor on plasmid pBW28, the transformation procedure and culturing of transformants were varied somewhat. The cells were not exposed to temperatures greater than 32° C. during transformation and subsequent culturing. The desired E. coli K12 MM294/pBW28 transformants were identified by their tetracycline-resistant, ampicillin-sensitive phenotype and by restriction enzyme analysis of their plasmid DNA.

D. Final Construction of Plasmid pBW32

Approximately 10 μg of plasmid pSV2-β-globin DNA (NRRL B-15928) were dissolved in 10 μl 10X HindIII reaction buffer, 5 μl (~50 units) restriction enzyme HindIII, and 85 μl H₂O, and the reaction was placed at 37° C. for 2 hours. The reaction mixture was then made 0.15M in LiCl, and after the addition of 2.5 volumes of ethanol and incubation in a dry ice-ethanol bath, the DNA was pelleted by centrifugation.

The DNA pellet was dissolved in 10 μl 10X BglII buffer, 5 μl (~50 units) restriction enzyme BglII, and 85 μH₂O, and the reaction was placed at 37° C. for two hours. After the BglII digestion, the reaction mixture was loaded onto a 0.85% agarose gel, and the fragments were separated by electrophoresis. The gel was visualized using ethidium bromide and ultraviolet light, and the band containing the desired ~4.2 kb HindIII-BglII fragment was excised from the gel as previously described. The pellet was resuspended in 10 μl of H₂O and constituted ~5 μg of the desired ~4.2 kb HindIII-BglII restriction fragment of plasmid pSV2-β-globin. The ~2.0 kb HindIII-BamHI restriction fragment of plasmid pTPA103 that encodes TPA was isolated from plasmid pTPA103 in substantial accordance with the foregoing teaching. About 5 μg of the ~2.0 kb HindIII-BamHI restriction fragment of plasmid pTPA103 were obtained, suspended in 10 μl of H$_2$O, and stored at −20° C.

Two μl of the ~4.2 kb BglII-HindIII restriction fragment of plasmid pSV2-β-globin and 4 μl of the ~2.0 kb HindIII-BamHI fragment of plasmid pTPA103 were mixed together and then incubated with 2 μl of 10X ligase buffer, 11 μl of H$_2$O, and 1 μl of T4 DNA ligase (~500 units) at 4° C. overnight. The ligated DNA constituted the desired plasmid pTPA301. The ligated DNA was used to transform E. coli K12 RR1 cells (NRRL B-15210) made competent for transformation in substantial accordance with the teaching of Example 3. Plasmid DNA was obtained from the E. coli K12 RR1/pTPA301 transformants in substantial accordance with the procedure of Example 1. A restriction site and function map of plasmid pTPA301 is presented in FIG. 10 of the accompanying drawings.

Plasmid pSV2-dhfr comprises a dihydrofalate reductase (dhfr) gene useful for selection of transformed eukaryotic cells and amplification of DNA covalently linked to the dhfr gene. Ten μg of plasmid pSV2-dhfr (isolated from E. coli K12 HB101/pSV2-dhfr, ATCC 37146) were mixed with 10 μl 10X PvuII buffer, 2 μl (~20 units) PvuII restriction enzyme, and 88 μl of H$_2$O, and the resulting reaction was incubated at 37° C. for two hours. The reaction was terminated by phenol and chloroform extractions, and then, the PvuII-digested plasmid pSV2-dhfr DNA was precipitated and collected by centrifugation.

BamHI linkers (5'-CGGATCCCG-3') were kinased and prepared for ligation by the following procedure. To 1 μg of linker in 5 μl H$_2$O was added: 10 μl 5X Kinase salts (300 mM Tris-HCl, pH=7.8; 50 mM MgCl$_2$; and 25 mM DTT), 5 μl of 5 mM ATP, 5 μl of BSA (1 mg/ml), 5 μl of 10 mM spermidine, 19 μl of H$_2$O, and 1 μl of polynucleotide Kinase (10 units/μl). This reaction was then incubated at 37° for 60 minutes and stored at −20° C. Five μl (~5 μg) of the PvuII-digested plasmid pSV2-dhfr and 12 μl (~0.25 μg) of the kinased BamHI linkers were mixed and incubated with 11 μl of H$_2$O, 2 μl 10X ligase buffer, and 1 μl (~1000 units) of T4 DNA ligase at 16° C. overnight.

Ten μl of 10X BamHI reaction buffer, 10 μl (~50 units) of BamHI restriction enzyme, and 48 μl of H$_2$O were added to the ligation reaction mixture, which was then incubated at 37° C. for 3 hours. The reaction was loaded onto a 1% agarose gel, and the desired ~1.9 kb fragment, which comprises the dhfr gene, was isolated from the gel. All linker additions performed in these examples were routinely purified on an agarose gel to reduce the likelihood of multiple linker sequences in the final vector. The ~3 μg of fragment obtained were suspended in 10 μl of TE buffer.

Next, approximately 15 μl (~1 μg) of plasmid pTPA301 were digested with BamHI restricton enzyme as taught above. Because there is a unique BamHI site in plasmid pTPA301, this BamHI digestion generates linear plasmid pTPA301 DNA. The BamHI-digested plasmid pTPA301 was precipitated with ethanol and resuspended in 94 μl of H$_2$O and phosphatased using 1 μl of Calf-Intestinal Alkaline Phosphatase (Collaborative Research, Inc., 128 Spring Street, Lexington, Mass. 02173), and 5 μl of 1M Tris-HCl, pH=9.0, at 65° C. for 45 min. The DNA was extracted with phenol:chloroform, then extracted with chloroform:isoamyl alcohol, ethanol precipitated, and resuspended in 20 μl H$_2$O. Ten μl (~0.25 μg) of phosphatased plasmid pTPA301 were added to 5 μl of the BamHI, dhfr-gene-containing restriction fragment (~1.5 μg), 3 μl of 10X ligase buffer, 3 μl (~1500 units) of T4 DNA ligase, and 9 μl H$_2$O. This ligation reaction was incubated at 15° C. overnight; the ligated DNA constituted the desired plasmid pTPA303 DNA.

Plasmid pTPA303 was used to transform E. coli K12 RR1 (NRRL B-15210), and the resulting E. coli K12 RR1/pTPA303 transformants were identified by their ampicillin-resistant phenotype and by restriction enzyme analysis of their plasmid DNA. Plasmid pTPA303 was isolated from the transformants in substantial accordance with the procedure of Example 1. A restriction site and function map of plasmid pTPA303 is presented in FIG. 10 of the accompanying drawings.

To isolate the ~2.7 kb EcoRI-BglII restriction fragment that encodes the pBR322 replicon and β-lactamase gene from plasmid pTPA301, about 10 μg of plasmid pTPA301 are digested to completion in 400 μl total reaction volume with 20 units BGlII restriction enzyme in 1X BglII buffer at 37° C. After the BglII digestion, the Tris-HCl concentration is adjusted to 110 mM, and 20 units of EcoRI restriction enzyme are added to the BglII-digested DNA. This reactin is allowed to incubate at 37° C. for 2 hours. The EcoRI-BglII-digested DNA is loaded onto an agarose gel and electrophoresed until the ~2.7 kb EcoRI-BglII restriction fragment is separated from the other digestion products, and then, the ~2.7 kb fragment is isolated and prepared for ligation.

To isolate a restriction fragment that comprises the dhfr gene, plasmid pTPA303 was double-digested with HindIII and EcoRI restriction enzymes, and the ~2340 bp EcoRI-HindIII restriction fragment that comprises the dhfr gene was isolated and recovered.

To isolate the ~2 kb HindIII-SstI restriction fragment of plasmid pTPA303 that comprises the coding region for the carboxy-terminus of TPA and the SV40 promoter, plasmid pTPA303 was double digested with HindIII and SstI restriction enzymes in 1X HindIII buffer. The ~1.7 kb fragment was isolated from the gel and prepared for ligation.

To isolate the ~680 bp XhoII (compatible for ligation with the BglII overlap)-SstI restriction fragment of plasmid pBW28 that comprises the coding region for the amino terminus of modified TPA, about 10 μg of plasmid pBW28 were digested with XhoII enzyme to completion in 1X XhoII buffer (0.1 M Tris-HCl, pH=8.0; 0.1M MgCl$_2$; 0.1% Triton X-100; and 1 mg/ml BSA). The XhoII-digested DNA was recovered by ethanol precipitation and subsequently digested to completion with SstI enzyme. The XhoII-SstI-digested DNA was loaded onto an acrylamide gel, and the desired fragment was isolated from the gel and prepared for ligation.

About 0.1 μg of each of the above fragments: the ~2.7 kb EcoRI-BglII restriction fragment of plasmid pTPA301; the ~2.34 kb EcoRI-HindIII restriction fragment of plasmid pTPA303; the ~1.7 kb SstI-HindIII restriction fragment of plasmid pTPA303; and the ~0.68 kb SstI-XhoII restriction fragment of plasmid pBW28 were ligated together to form plasmid pBW32.

The ligation mix was used to transform *E. coli* K12 MM294 as taught in Example 3, except that 50 mM CaCl₂ was used in the procedure. Transformants were identified by their ampicillin-resistant phenotype and by restriction analysis of their plasmid DNA. Plasmid pBW32 DNA was obtained from the *E. coli* K12 MM294/pBW32 transformants in substantial accordance with the procedure of Example 1. A restriction site and function map of plasmid pBW32 is presented in FIG. 10 of the accompanying drawings.

EXAMPLE 17

Construction of Plasmids pLPChd1 and pLPChd2

About 20 μg of plasmid pBW32 in 20 μl of TE buffer were added to 10 μl of 10X BamHI buffer and 60 μl of H₂O. About 10 μl (~50 units) of restriction enzyme BamHI were added to the solution of plasmid pBW32 DNA, and the resulting reaction was incubated at 37° C. for two hours. The BamHI-digested plasmid pBW32 DNA was precipitated with ethanol, collected by centrifugation, and resuspended in 5 μl of 10X Klenow buffer, 45 μl of H₂O, and 2 μl (~100 units) of Klenow enzyme. The reaction was incubated at 16° C. for 30 minutes; then, the reaction mixture was loaded onto an agarose gel and electrophoresed until the digestion products were clearly separated. The ~1.9 kb Klenow-treated, BamHI restriction fragment of plasmid pBW32 that comprises the dhfr gene was isolated from the gel and prepared for ligation in substantial accordance with the procedure of Example 12A. About 4 μg of the desired fragment were obtained and suspended in 5 μl of TE buffer.

About 200 μg of plasmid pLPChyg1 in 100 μl of TE buffer were added to 15 μl of 10X EcoRI buffer and 30 μl of H₂O. About 5 μl (~50 units) of restriction enzyme EcoRI were added to the solution of plasmid pLPChyg1 DNA, and the resulting reaction was incubated at 37° C. for about 10 minutes. The short reaction time was calculated to produce a partial EcoRI digestion. Plasmid pLPChyg1 has two EcoRI restriction sites, one of which is within the coding sequence of the hygromycin resistance-conferring (HmR) gene, and it was desired to insert the dhfr-gene.-containing restriction fragment into the EcoRI site of plasmid pLPChyg1 that is not in the HmR gene. The partially-EcoRI-digested plasmid pLPChyg1 DNA was loaded onto an agarose gel and electrophoresed until the singly-cut plasmid pLPChyg1 DNA was separated from uncut plasmid DNA and the other digestion products. The singly-cut DNA was isolated from the gel and prepared for ligation in substantial accordance with the procedure of Example 12A. About 2 μg of the singly-EcoRI-cut plasmid pLPChyg1 were obtained and suspended in 25 μl of TE buffer. To this sample, about 5 μl (~25 units) of Klenow enzyme, 5 μl of 10X Klenow buffer, and 40 μl of H₂O were added, and the resulting reaction was incubated at 16° C. for 60 minutes. The Klenow-treated, partially-EcoRI-digested DNA was then extracted twice with phenol and then once with chloroform, precipitated with ethanol, and resuspended in 25 μl of TE buffer.

About 5 μl of the ~1.9 kb Klenow-treated BamHI restriction fragment of plasmid pBW32 and about 5 μl of the singly-EcoRI-cut plasmid pLPChyg1 DNA were mixed together, and 1 μl of 10X ligase buffer, 5 μl of H₂O, 1 μl (~500 units) of T4 DNA ligase, and 1 μl (~2 units) of T4 RNA ligase were added to the mixture of DNA, and the resulting reaction was incubated at 16° C. overnight. The ligated DNA constituted the desired plasmids pLPChd1 and pLPChd2, which differ only with respect to the orientation of the ~1.9 kb fragment that comprises the dhfr gene.

The ligated DNA was used to transform *E. coli* K12 HB101 cells made competent for transformation in substantial accordance with the procedure of Example 3. The transformed cells were plated onto L agar containing 100 μg/ml ampicillin, and the ampicillin-resistant transformants were analyzed by restriction enzyme analysis of their plasmid DNA to identify the *E. coli* K12 HB101/pLPChd1 and *E. coli* K12 HB101/pLPChd2 transformants. For the purposes of this disclosure, plasmid pLPChd1 has been designated plasmid pLChd. A restriction site and function map of plasmid pLPChd is presented in FIG. 11 of the accompanying drawings. Plasmid pLPChd1 and plasmid pLPChd2 DNA were isolated from the appropriate transformants in substantial accordance with the procedure of Example 1.

EXAMPLE 18

Construction of Plasmid phd

To construct plasmid phd, it was necessary to prepare the plasmid pLPChd1 DNA, used as starting material in the construction of plasmid phd, from *E. coli* host cells that lack an adenine methylase, such as that encoded by the dam gene, the product of which methylates the adenine residue in the sequence 5'-GATC-3'. *E. coli* K12 GM48 (NRRL B-15725) lacks a functional dam methylase and so is a suitable host to use for the purpose of preparing plasmid pLPChd1 DNA for use as starting material in the construction of plasmid phd.

*E. coli* K12 GM48 cells were cultured and made competent for transformation, and plasmid pLPChyg1 was used to transform the *E. coli* K12 GM48 cells in substantial accordance with the procedure of Example 3. The transformed cells were plated on L agar containing ampicillin, and once the ampicillin-resistant, *E. coli* K12 GM48/pLPChd1 transformants had formed colonies, one such colony was used to prepare plasmid pLPChd1 DNA in substantial accordance with the procedure of Example 1. About 1 mg of plasmid pLPChd1 DNA was obtained and suspended in about 1 ml of TE buffer.

About 2 μg of plasmid pLPChd1 DNA in 2 μl of TE buffer were added to 2 μl of 10X BclI buffer (750 mM KCl; 60 mM Tris-HCl, pH=7.4; 100 mM MgCl₂; 10 mM DTT and 1 mg/ml BSA) and 14 μl of H₂O. About 2 μl (~10 units) of restriction enzyme BclI were added to the solution of plasmid pLPChd1 DNA, and the resulting reaction was incubated at 50° C. for two hours. The reaction was stopped by extracting the mixture once with phenol and twice with chloroform.

About 1 μl of the BclI-digested plasmid pLPChd1 DNA was added to 1 μl of 10X ligase buffer, 8 μl of H₂O and 1 μl (~500 units) of T4 DNA ligase. The ligation reaction was incubated at 16° C. overnight, and the ligated DNA constituted the desired plasmid phd. Plasmid phd results from the deletion of the extra BclI linkers that attached during the construction of plasmid pLPcat and the two adjacent BclI restriction fragments of a total size of about 1.45 kb from plasmid pLPChd1. A restriction site and function map of plasmid phd is presented in FIG. 11 of the accompanying drawings. Plasmid phd facilitates the expression of any DNA sequence from the BK virus enhancer-adenovirus late promoter of the present invention, because the DNA to be expressed can be readily inserted in the correct position for expression at the single BclI site on plasmid phd.

The ligated DNA was used to transform *E. coli* K12 GM48 in substantial accordance with the procedure of Example 3. The transformed cells were plated on L agar containing ampicillin, and the ampicillin-resistant *E. coli* K12 GM48/phd transformants were identified by restriction enzyme analysis of their plasmid DNA.

EXAMPLE 19

Construction of Plasmid pL-KSL

Plasmid pGKC2310 contains the entire, full-length cDNA which encodes the light chain of murine monoclonal antibody KS1/4. *E. coli* K12 MM294/pGKC2310 can be obtained from the Northern Regional Research Laboratory under the accession number NRRL B-18356. A restriction site and function map of plasmid pGKC2310 is presented in FIG. 12 of the accompanying drawings. Plasmid DNA is extracted from the culture in substantial accordance with the teaching of Example 1, except that the temperature of incubation is 37° C.

About 5 μg of plasmid pGKC2310 are digested with restriction enzyme EcoRI in substantial accordance with the teaching of Example 8, then treated with Klenow in substantial accordance with the teaching of Example 5. Next, BamHI linkers (purchased from New England Biolabs) are added to the DNA fragments in substantial accordance with the teaching of Example 2. Finally, the DNA is electrophoresed through an agarose gel and purified in substantial accordance with the teaching of Example 12. The desired ~1.1 kb fragment is ethanol precipitated and resuspended in 5 μl TE.

About 1 μg of plasmid phd was digested with restriction enzyme BclI in substantial accordance with the teaching of Example 18, then electrophoresed and purified in substantial accordance with the teaching of Example 12. The ~1.1 kb EcoRI-digested, Klenow-treated, linker-modified DNA fragment of plasmid pGKC2310 is then ligated into the BclI-digested plasmid phd in substantial accordance with the teaching of Example 2. This ligation mixture is then transformed into *E. coli* cells in substantial accordance with the teaching of Example 3. The plasmids are then isolated from the cells in substantial accordance with the teaching of Example 1, and the plasmid containing the correct orientation is designated plasmid pL-KSL.

EXAMPLE 20

Construction of Plasmid pH-KS

Plasmid pG2A52 contains the entire, full-length cDNA which encodes the heavy chain of murine monoclonal antibody KS1/4. *E. coli* K12 MM294/pG2A52 can be obtained from the Northern Research Laboratory under the accession number NRRL B-18357. A restriction site and function map of plasmid pG2A52 is presented in FIG. 12 of the accompanying drawings. Plasmid DNA is extracted from the culture in substantial accordance with the teaching of Example 1, except that the temperature of incubation is 37° C.

About 5 μg of plasmid pG2A52 are digested with restriction enzyme EcoRI in substantial accordance with the teaching of Example 8, then treated with Klenow in substantial accordance with the teaching of Example 5. Next, BamHI linkers (purchased from New England Biolabs) are added to the DNA fragments in substantial accordance with the teaching of Example 2. Finally, the DNA is electrophoresed through an agarose gel and purified in substantial accordance with the teaching of Example 12. The desired ~1.6 kb fragment is ethanol precipitated and resuspended in 5 μl TE.

About 1 μg of plasmid phd was digested with restriction enzyme BclI in substantial accordance with the teaching of Example 18, then electrophoresed and purified in substantial accordance with the teaching of Example 12. The ~1.6 kb EcoRI-digested, Klenow-treated, linker-modified DNA fragment of plasmid pG2A52 is then ligated into the BclI-digested plasmid phd in substantial accordance with the teaching of Example 2. This ligation mixture is then transformed into *E. coli* cells in substantial accordance with the teaching of Example 3. The plasmids are then isolated from the cells in substantial accordance with the teaching of Example 1, and the plasmid containing the correct orientation is designated plasmid pH-KS.

EXAMPLE 21

Construction of Plasmid pL-HD

Plasmid pCHKC2-18 contains a cDNA fragment which encodes the light chain variable region of murine monoclonal antibody KS1/4 joined to a genomic DNA fragment which encodes a human light chain constant region. The variable region encoded by plasmid pCHKC2-18 contains a single amino acid alteration from the naturally-occurring variable region of monoclonal antibody KS1/4. The carboxy-terminal amino acid in the wild-type variable region is an arginine residue, whereas said residue is a glycine residue in the protein encoded by plasmid pCHKC2-18. *E. coli* K12 DH5/pCHK2-18 can be obtained from the Northern Regional Research Laboratory under the accession number NRRL B-18359. A restriction site and function map of plasmid pCHKC2-18 is present in FIG. 13 of the accompanying drawings. Plasmid DNA is extracted from the culture in substantial accordance with the teaching of Example 1, except that the temperature of incubation is 37° C.

About 5 mg of plasmid pCHKC2-18 was digested in substantial accordance with the teaching of Example 8, except restriction enzyme FnuDII and 10X FnuDII buffer (60 mM NaCl, 60 mM Tris-HCl (pH 7.4) and 60 mM MgCl$_2$) were used. The DNA was next digested using restriction enzyme HindIII and 10X HindIII buffer (500 mM NaCl, 500 mM Tris-HCl (pH 8.0) and 100 mM MgCl$_2$), then the ~1.3 kb FnuDII-HindIII fragment was isolated from an agarose gel in substantial accordance with the teaching of Example 12. After ethanol precipitation and resuspension, the 5' overhang of the HindIII site was filled in using Klenow, in substantial accordance with the teaching of Example 5.

About 0.5 μg of BclI digested plasmid phd (isolated in Example 20) was also treated with Klenow in substantial accordance with the teaching of Example 5. The ~1.3 kb FnuDII-HindIII-cut, filled-in fragment of plasmid pCHKC2-18 was then ligated into the BclI-cut, filled-in vector fragment of plasmid phd in substantial accordance with the teaching of Example 2. This ligation mixture was then transformed into *E. coli* cells in substantial accordance with the teaching of Example 3. The plasmids were then isolated from the cells in substantial accordance with the teaching of Example 1, and the plasmid containing the correct orientation (evidenced by an ~840 bp MaeII-StuI fragment) was designated plasmid pL-HD.

EXAMPLE 22
Construction of Plasmid pL-HD2

Plasmid pCHKC2-6 contains a cDNA fragment which encodes the light chain variable region of monoclonal antibody KS1/4 joined to a genomic DNA fragment which encodes a human light chain constant region. The variable region encoded by plasmid pCHKC2-6 contains the same amino acid residue sequence as the naturally-occurring variable region of monoclonal KS1/4. However, the DNA which encoded the carboxy-terminal arginine residue contains a CGT codon in plasmid pCHKC2-6, rather than the CGG codon which occurs in the natural sequence. *E. coli* K12 DH5/pCHKC2-6 can be obtained from the Northern Regional Research Laboratory under the accession number NRRL B-18358. A restriction site and function map of plasmid pCHKC2-6 is presented in FIG. 13 of the accompanying drawings.

Plasmid DNA is extracted from the culture in substantial accordance with the teaching of Example 1, except the temperature of incubation is 37° C. Plasmid pCHKC2-6 is then digested with restriction enzymes FnuDII and HindIII, treated with Klenow, then ligated into BclI-cut, filled-in plasmid phd in substantial accordance with the teaching of Example 21. The resultant plasmid is then transformed into *E. coli*, extracted and mapped in substantial accordance with the teaching of Example 21. The plasmid with the correct ~840 bp MaeII-StuI fragment is designated plasmid pL-HD2.

EXAMPLE 23
Construction of Plasmid pH1-HD

Plasmid pCH2A5 contains a cDNA fragment which encodes the heavy chain variable region of murine monoclonal antibody KS1/4 joined to a genomic DNA fragment which encodes a human heavy chain constant region of immunoglobulin IgG1. *E. coli* K12 MM294/pCH2A5 can be obtained from the Northern Regional Research Laboratories under the accession number NRRL B-18360. A restriction site and function map of plasmid pCH2A5 is presented in FIG. 14 of the accompanying drawings. Plasmid DNA is extracted from the culture in substantial accordance with the teaching of Example 1, except the temperature of incubation is 37° C.

About 10 μg of plasmid pCH2A5 were cut with restriction enzyme EcoRI in substantial accordance with the teaching of Example 5. The DNA was treated with Klenow and BamHI linkers (purchased from New England Biolabs) were then added in substantial accordance with the teaching of Example 2, and the DNA was digested with restriction enzyme BamHI in substantial accordance with the teaching of Example 5. The ~7.4 kb BamHI-EcoRI/BamHI restriction fragment was then isolated from an agarose gel in substantial accordance with the teaching of Example 12. This fragment was then ligated into the BclI digested phd vector (Example 20) in substantial accordance with the teaching of Example 2. The DNA was then transformed into E. coli, reisolated, and the plasmid with the correct orientation (evidenced by an ~780 bp MaeIII-StuI fragment) was designated plasmid pH1-HD.

EXAMPLE 24
Construction of Plasmid pH2-HD

Plasmid pCH2A5IG2 contains a cDNA fragment which encodes the heavy chain variable region of murine monoclonal antibody KS1/4 joined to a genomic DNA fragment which encodes a human heavy chain constant region of immunoglobulin IgG2. *E. coli* K12 DH5/pCH2A5IG2 can be obtained from the Northern Regional Research Laboratories under the accession number NRRL B-18361. A restriction site and function map of plasmid pCH2A5IG2 is presented in FIG. 14 of the accompanying drawings. Plasmid DNA is extracted from the culture in substantial accordance with the teaching of Example 1, except the temperature of incubation is 37° C.

About 10 μg of plasmid pCH2A5IG2 were cut with restriction enzyme EcoRI in substantial accordance with the teaching of Example 5. The DNA was treated with Klenow and BamHI linkers (purchased from New England Biolabs) were then added in substantial accordance with the teaching of Example 2, and the DNA was digested with restriction enzyme BamHI in substantial accordance with the teaching of Example 5. The ~6.1 kb BamHI-EcoRI/BamHI restriction fragment was then isolated from an agarose gel in substantial accordance with the teaching of Example 12. This fragment was then ligated into the BclI digested phd vector (Example 20) in substantial accordance with the teaching of Example 2. The DNA was then transformed into *E. coli*, reisolated, and the plasmid with the correct orientation (evidenced by an ~780 bp MaeIII-StuI fragment) was designated plasmid pH2-HD.

EXAMPLE 24
Construction of Plasmid pH3-HD

Plasmid pCH2A5IG3 contains a cDNA fragment which encodes the heavy chain variable region of murine monoclonal antibody KS1/4 joined to a genomic DNA fragment which encodes a human heavy chain constant region of immunoglobulin IgG1. *E. coli* K12 DH5/pCH2A5IG3 can be obtained from the Northern Regional Research Laboratories under the accession number NRRL B-18362. A restriction site and function map of plasmid pCH2A5IG3 is presented in FIG. 15 of the accompanying drawings. Plasmid DNA is extracted from the culture in substantial accordance with the teaching of Example 1, except the temperature of incubation is 37° C.

About 10 μg of plasmid pCH2A5IG3 were cut with restriction enzyme EcoRI in substantial accordance with the teaching of Example 5. The DNA was treated with Klenow and BamHI linkers (purchased from New England Biolabs) were then added in substantial accordance with the teaching of Example 2, and the DNA was digested with restriction enzyme BamHI in substantial accordance with the teaching of Example 5. The ~7.4 kb BamHI-EcoRI/BamHI restriction fragment was then isolated from an agarose gel in substantial accordance with the teaching of Example 12. This fragment was then ligated into the BclI digested phd vector (Example 20) in substantial accordance with the teaching of Example 2. The DNA was then transformed into *E. coli*, reisolated, and the plasmid with the correct orientation (evidenced by an ~780 bp MaeIII-StuI fragment) was designated plasmid pH3-HD.

EXAMPLE 26

Construction of Plasmid pH4-HD

Plasmid pCH2A5IG4 contains a cDNA fragment which encodes the heavy chain variable region of murine monoclonal antibody KS1/4 joined to a genomic DNA fragment which encodes a human heavy chain constant region of immunoglobulin IgG4. *E. coli* K12 DH5/pCH2A5IG4 can be obtained from the Northern Regional Research Laboratories under the accession number NRRL B-18363. A restriction site and function map of plasmid pCH2A5IG4 is presented in FIG. 15 of the accompanying drawings. Plasmid DNA is extracted from the culture in substantial accordance with the teaching of Example 1, except the temperature of incubation is 37° C.

About 10 μg of plasmid pCH2A5IG4 were cut with restriction enzyme EcoRI in substantial accordance with the teaching of Example 5. The DNA was treated with Klenow and BamHI linkers (purchased from New England Biolabs) were then added in substantial accordance with the teaching of Example 2, and the DNA was digested with restriction enzyme BamHI in substantial accordance with the teaching of Example 5. The ~6.1 kb BamHI -EcoRI/BamHI restriction fragment teaching of Example 2. The DNA was then transformed into *E. coli*, reisolated, and the plasmid with the correct orientation (evidenced by an ~780 bp MaeIII-StuI fragment) was designated plasmid pH4-HD.

EXAMPLE 27

Construction of Eukaryotic Host Cell Transformants of Expression Vectors

The present expression vectors contain the BK enhancer described in U.S. patent application No. 07/129,028, Attorney Docket X-6606A, filed Dec. 4, 1987, the teaching of which is incorporated herein by reference. The BK enhancer stimulates gene expression in the presence of the EIA gene product. Because 293 cells constitutively express the EIA gene product, 293 cells are an efficient host for the eukaryotic expression vectors of the present invention. 293 cells are human embryonic kidney cells transformed with adenovirus type 5 (note that any particular type of adenovirus can be used to supply the EIA gene product in the method of the present invention) and are available from the ATCC under the accession number CRL 1573. However, the expression vectors of the present invention function in a wide variety of host cells, even if the E1A gene product is not present. Furthermore, the E1A gene product can be introduced into a non-E1A-producing cell line either by transformation with a vector that comprises the E1A gene, or with sheared adenovirus DNA, or by infection with adenovirus.

The transformation procedure described below refers to 293 cells as the host cell line; however, the procedure is generally applicable to most eukaryotic cell lines. 293 cells are obtained from the ATCC under the accession number CRL 1573 in a 25 mm² flask containing a confluent monolayer of about $5.5 \times 10^6$ cells in Eagle's Minimum Essential Medium with 10% heat-inactivated horse serum. The flask is incubated at 37° C.; medium is changed twice weekly. The cells are subcultured by removing the medium, rinsing with Hank's Balanced Salts solution (Gibco), adding 0.25% trypsin for 1-2 minutes, rinsing with fresh medium, aspirating, and dispensing into new flasks at a subcultivation ratio of 1:5 or 1:10.

One day prior to transformation, cells are seeded at $0.7 \times 10^6$ cells per dish. The medium is changed 4 hours prior to transformation. Sterile, ethanol-precipitated plasmid DNA dissolved in TE buffer is used to prepare a 2X DNA-CaCl$_2$ solution containing 40 μg/ml DNA and 250 mM CaCl$_2$. 2X HBS is prepared containing 280 mM NaCl, 50 mM Hepes, and 1.5 mM sodium phosphate, with the pH adjusted to 7.05-7.15. The 2X DNA-CaCl$_2$ solution is added dropwise to an equal volume of sterile 2X HBS. A one ml sterile plastic pipette with a cotton plug is inserted into the mixing tube that contains the 2X HBS, and bubbles are introduced by blowing while the DNA is being added. The calcium-phosphate-DNA precipitate is allowed to form without agitation for 30-45 minutes at room temperature.

The precipitate is then mixed by gentle pipetting with a plastic pipette, and one ml (per plate) of precipitate is added directly to the 10 ml of growth medium that covers the recipient cells. After 4 hours of incubation at 37° C., the medium is replaced with DMEM with 10% fetal bovine serum and the cells allowed to incubate for an additional 72 hours before providing selective pressure. For plasmids that do not comprise a selectable marker that functions in eukaryotic cells, the transformation procedure utilizes a mixture of plasmids: an expression vector that lacks a selectable marker; and an expression vector that comprises a selectable marker that functions in eukaryotic cells. This co-transformation technique allows for the identification of cells that comprise both of the transforming plasmids.

For cells transfected with plasmids containing the hygromycin resistance-conferring gene, hygromycin is added to the growth medium to a final concentration of about 200 to 400 μg/ml. The cells are then incubated at 37° C. for 2-4 weeks with medium changes at 3 to 4 day intervals. The resulting hygromycin-resistant colonies are transferred to individual culture flasks for characterization. The selection of neomycin (G418 is also used in place of neomycin)-resistant colonies is performed in substantial accordance with the selection procedure for hygromycin-resistant cells, except that neomycin is added to a final concentration of 400 μg/ml rather than hygromycin. 293 cells are dhfr positive, so 293 transformants that contain plasmids comprising the dhfr gene are not selected solely on the basis of the dhfr-positive phenotype, which is the ability to grow in media that lacks hypoxanthine and thymine. Cell lines that do lack a functional dhfr gene and are transformed with dhfr-containing plasmids can be selected for on the basis of the dhfr+ phenotype.

The use of the dihydrofolate reductase (dhfr) gene as a selectable marker for introducing a gene or plasmid into a dhfr-deficient cell line and the subsequent use of methotrexate to amplify the copy number of the plasmid has been well established in the literature. Although the use of dhfr as a selectable and amplifiable marker in dhfr-producing cells has not been well studied, evidence in the literature would suggest that dhfr can be used as a selectable marker in dhfr-producing cells and for gene amplification. The use of the present invention is not limited by the selectable marker used. Moreover, amplifiable markers such as metallothionein genes, adenosine deaminase genes, or members of the multigene resistance family, exemplified by P-glycoprotein, can be utilized. In 293 cells, it is advantageous to transform with a vector that contains a selectable marker such as the hygromycin B resistance-conferring gene and then amplify using methotrexate, which cannot be used for selection of murine dhfr-containing plasmids in 293 cells.

Cell line AV12 (ATCC CRL 9595) were transformed in substantial accordance with the procedure described for 293 cells. AV12 cells also constitutively express the E1A gene product and are the preferred host for the eukaryotic expression vectors of the present invention. However, unlike 293 cells, AV12 cells were directly selected with methotrexate (200–500 nM) when transformed with a vector containing the murine dhfr gene. To express a heavy chain, it was necessary to transform the AV12 cells with any expression vector which encodes a heavy chain. However, a heavy chain will not be secreted into the supernatent unless the AV12 cells are also co-transformed with a vector encoding a light chain. Light chains will be secreted from host cells after transformation with a vector encoding light chains. In this manner, various combinations of light and heavy chains were expressed via co-transformation and selection of AV12 cells. To assay for the production of a fully assembled, secreted immunoglobulin, one therefore should assay for the presence of a secreted heavy chain.

EXAMPLE 28

Assay for Immunoglobulin Production

The methotrexate-resistant transformants obtained in Example 27 are grown on 100 mm² tissue culture dishes at a density of several hundred cell clones per tissue culture dish. The media is decanted, and the cells are rinsed twice with 5 ml aliquots of Hank's Balanced salt solution (Gibco). A solution of sterile 0.45% agar (Sigma Type 4 agarose, catalogue #A3643, Sigma Chemical Co., P.O. Box 14508, St. Louis, MO 63178) is prepared by mixing 1 ml of 1.8% agar (47° C.) with 3 ml of Dulbecco's Modified Eagle's (DME) Salts (Gibco) (37° C.), and 2 ml of this 0.45% agar solution are layered over the cells.

Nitrocellulose filters (Schleicher and Schuell, Inc., Keene, NH 03431) are boiled and then autoclaved 2 hours to remove the wetting agent, which is toxic to the cells. The filters are then placed on top of the agar layer, and after air bubbles are removed, the plates are incubated at 37° C. for 1 to 3 hours. The filters, previously marked to indicate the original orientation of the filter on the dish so as to facilitate later identification of colonies, are then removed and placed in PBS (50 mM Tris-HCl, pH=7.2, and 150 mM NaCl).

To keep the cells on the dish viable during analysis of the filters, the cells are overlayed with 8 ml of a mixture containing 2 ml of 1.8% agar (47° C.), 2 ml of DME salts (37° C.), and 4 ml of DME salts with 20% fetal bovine serum (37° C.). The cells are then placed in a 37° C. incubator.

All washes and reactions carried out on the filters are accomplished while the filters are on a rocking platform. The filters are first blocked by incubation at room temperature in 5% milk in PBS. The filters are then rinsed (5 minutes/rinse) four times in PBS. A 10 µg/ml biotinylated goat anti-human heavy chain (Vector Laboratories, Inc., 30 Ingold Rd., Burlingame, CA 94010) polyclonal antibody in 2.5% bovine serum albumin is added to the filter (in sufficient quantities to cover the filter), which is then incubated at 37° C. for 1 hour.

Polyclonal antibody can be prepared by the procedure disclosed in *Structural Concepts in Immunology and Immunochemistry* by E. A. Kabat, published in 1968 by Holt, Rhinehart, and Winston. Monoclonal antibody, which is also suitable for use in the assay, can be prepared as disclosed in Kohler and Milstein, 1975, Nature, 256:495, or as disclosed in U.S. Pat. No. 4,696,895; EPO Pub. No. 205046; Laurell et al., 1985, FEBS 191(1):75; Suzuki et al., 1985, J. Biochem. 97:127-138; and EPO Pub. No. 138222. The avidin D and biotinylated horse radish peroxidase (HRP) used in the assay are obtained in a Vectastain ™ kit (Vector Laboratories, Inc. Biotin is also obtained from Vector Laboratories, Inc.

The filters are rinsed four times with PBS at 4° C. Then, avidin D and biotinylated horse radish peroxidase are prepared and added as per the manufacturer's instructions in the Vectastain ™ (Vector Laboratories) kit. The filters are incubated with the HRP-conjugated avidin D for 1 hour at 4° C. (longer incubation times, i.e., overnight, can be used when small amounts of protein are being secreted); then, the filters are rinsed four times with PBS at 4° C.

To develop the indicator color on the filters, about 30 mg of HRP color-development reagent (4-chloro-1-napthol, Sigma) dissolved in ice-cold 100% methanol are added to 50 ml of PBS and 30 µof 30% $H_2O_2$. This mixture is added to the nitrocellulose filters, which are incubated at room temperature until the color develops. Colonies secreting the most antibody of the invention will be indicated on the filters not only by earliest appearance of the color but also by darker spots on the filter.

After the filters have been developed, the filters are again realigned with the original plates to determine which colonies are associated with which spots on the filter. The colonies secreting the most antibody are then selected and used for production of the antibody.

Those skilled in the art will recognize that the above assay is merely illustrative of the method of identifying high secreting cell lines. A variety of assay procedures can be successfully employed in the method. For instance, a double-antibody reaction can be employed in which the biotinylated goat anti human heavy chain antibody is replaced with a goat anti-human heavy chain (IgG) and a biotinylated anti-goat IgG antibody.

We claim:
1. A recombinant DNA compound that comprises DNA encoding an antibody light chain with the amino acid residue sequence consisting essentially of:

|     | Gln | Ile | Leu | Leu | Thr | Gln | Ser | Pro | Ala | Ile | Met | Ser | Ala | Ser |
| --- | --- | --- | --- | --- | --- | --- | --- | --- | --- | --- | --- | --- | --- | --- |
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |
| Pro | Trp | Ile | Phe | Asp | Thr | Ser | Asn | Leu | Ala | Ser | Gly | Phe | Pro | Ala |
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Arg | Ala | Asp | Ala | Ala | Pro | Thr | Val | Ser | Ile | Phe | Pro | Pro |
| Ser | Ser | Glu | Gln | Leu | Thr | Ser | Gly | Gly | Ala | Ser | Val | Val | Cys | Phe |

-continued

| Leu | Asn | Asn | Phe | Tyr | Pro | Lys | Asp | Ile | Asn | Val | Lys | Trp | Lys | Ile |
|---|---|---|---|---|---|---|---|---|---|---|---|---|---|---|
| Asp | Gly | Ser | Glu | Arg | Gln | Asn | Gly | Val | Leu | Asn | Ser | Trp | Thr | Asp |
| Gln | Asp | Ser | Lys | Asp | Ser | Thr | Tyr | Ser | Met | Ser | Ser | Thr | Leu | Thr |
| Leu | Thr | Lys | Asp | Glu | Tyr | Glu | Arg | His | Asn | Ser | Tyr | Thr | Cys | Glu |
| Ala | Thr | His | Lys | Thr | Ser | Thr | Ser | Pro | Ile | Val | Lys | Ser | Phe | Asn |
| Arg | Asn | Glu | Cys | | | | | | | | | | | |

2. The recombinant DNA compound of claim 1 wherein the coding strand is:

4. The recombinant DNA compound of claim 3 wherein the coding strand is:

|     | CAA | ATT | CTT | CTC | ACC | CAG | TCT | CCA | GCA | ATC | ATG | TCT | GCA | TCT |
|---|---|---|---|---|---|---|---|---|---|---|---|---|---|---|
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |
| ATA | AAA | CGG | GCT | GAT | GCT | GCA | CCA | ACT | GTA | TCC | ATC | TTC | CCA | CCA |
| TCC | AGT | GAG | CAG | TTA | ACA | TCT | GGA | GGT | GCC | TCA | GTC | GTG | TGC | TTC |
| TTG | AAC | AAC | TTC | TAC | CCC | AAA | GAC | ATC | AAT | GTC | AAG | TGG | AAG | ATT |
| GAT | GGC | AGT | GAA | CGA | CAA | AAT | GGC | GTC | CTG | AAC | AGT | TGG | ACT | GAT |
| CAG | GAC | AGC | AAA | GAC | AGC | ACC | TAC | AGC | ATG | AGC | AGC | ACC | CTC | ACG |
| TTG | ACC | AAG | GAC | GAG | TAT | GAA | CGA | CAT | AAC | AGC | TAT | ACC | TGT | GAG |
| GCC | ACT | CAC | AAG | ACA | TCA | ACT | TCA | CCC | ATT | GTC | AAG | AGC | TTC | AAC |
| AGG | AAT | GAG | TGT | | | | | | | | | | | |

|     |     |     |     |     |     |     |     |     | ATG | GAT | TTT | CAA | GTG | CAG |
|---|---|---|---|---|---|---|---|---|---|---|---|---|---|---|
| ATT | TTT | AGC | TTC | CTG | CTA | ATC | AGT | GCT | TCA | GTC | ATA | ATG | TCC | AGA |
| GGA | CAA | ATT | CTT | CTC | ACC | CAG | TCT | CCA | GCA | ATC | ATG | TCT | GCA | TCT |
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |
| ATA | AAA | CGG | GCT | GAT | GCT | GCA | CCA | ACT | GTA | TCC | ATC | TTC | CCA | CCA |
| TCC | AGT | GAG | CAG | TTA | ACA | TCT | GGA | GGT | GCC | TCA | GTC | GTG | TGC | TTC |
| TTG | AAC | AAC | TTC | TAC | CCC | AAA | GAC | ATC | AAT | GTC | AAG | TGG | AAG | ATT |
| GAT | GGC | AGT | GAA | CGA | CAA | AAT | GGC | GTC | CTG | AAC | AGT | TGG | ACT | GAT |
| CAG | GAC | AGC | AAA | GAC | AGC | ACC | TAC | AGC | ATG | AGC | AGC | ACC | CTC | ACG |
| TTG | ACC | AAG | GAC | GAG | TAT | GAA | CGA | CAT | AAC | AGC | TAT | ACC | TGT | GAG |
| GCC | ACT | CAC | AAG | ACA | TCA | ACT | TCA | CCC | ATT | GTC | AAG | AGC | TTC | AAC |
| AGG | AAT | GAG | TGT | | | | | | | | | | | |

3. A recombinant DNA compound that comprises DNA encoding an antibody light chain and the signal peptide of said light chain with the amino acid sequence consisting essentially of:

5. A recombinant DNA compound that comprises DNA encoding an antibody heavy chain with the amino acid residue sequence consisting essentially of:

|     |     |     |     |     |     |     |     |     | Met | Asp | Phe | Gln | Val | Gln |
|---|---|---|---|---|---|---|---|---|---|---|---|---|---|---|
| Ile | Phe | Ser | Phe | Leu | Leu | Ile | Ser | Ala | Ser | Val | Ile | Met | Ser | Arg |
| Gly | Gln | Ile | Leu | Leu | Thr | Gln | Ser | Pro | Ala | Ile | Met | Ser | Ala | Ser |
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |
| Pro | Trp | Ile | Phe | Asp | Thr | Ser | Asn | Leu | Ala | Ser | Gly | Phe | Pro | Ala |
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Arg | Ala | Asp | Ala | Ala | Pro | Thr | Val | Ser | Ile | Phe | Pro | Pro |
| Ser | Ser | Glu | Gln | Leu | Thr | Ser | Gly | Gly | Ala | Ser | Val | Val | Cys | Phe |
| Leu | Asn | Asn | Phe | Tyr | Pro | Lys | Asp | Ile | Asn | Val | Lys | Trp | Lys | Ile |
| Asp | Gly | Ser | Glu | Arg | Gln | Asn | Gly | Val | Leu | Asn | Ser | Trp | Thr | Asp |
| Gln | Asp | Ser | Lys | Asp | Ser | Thr | Tyr | Ser | Met | Ser | Ser | Thr | Leu | Thr |
| Leu | Thr | Lys | Asp | Glu | Tyr | Glu | Arg | His | Asn | Ser | Tyr | Thr | Cys | Glu |
| Ala | Thr | His | Lys | Thr | Ser | Thr | Ser | Pro | Ile | Val | Lys | Ser | Phe | Asn |
| Arg | Asn | Glu | Cys | | | | | | | | | | | |

|     |     |     | Gln | Ile | Gln | Leu | Val | Gln | Ser | Gly | Pro | Glu | Leu | Lys |
|---|---|---|---|---|---|---|---|---|---|---|---|---|---|---|
| Lys | Pro | Gly | Glu | Thr | Val | Lys | Ile | Ser | Cys | Lys | Ala | Ser | Gly | Tyr |
| Thr | Phe | Thr | Asn | Tyr | Gly | Met | Asn | Trp | Val | Lys | Gln | Thr | Pro | Gly |
| Lys | Gly | Leu | Lys | Trp | Met | Gly | Trp | Ile | Asn | Thr | Tyr | Thr | Gly | Glu |

-continued

| Pro | Thr | Tyr | Ala | Asp | Asp | Phe | Lys | Gly | Arg | Phe | Ala | Phe | Ser | Leu |
|---|---|---|---|---|---|---|---|---|---|---|---|---|---|---|
| Glu | Thr | Ser | Ala | Ser | Thr | Ala | Phe | Leu | Gln | Ile | Gln | Gln | Pro | Gln |
| Asn | Met | Arg | Thr | Met | Ala | Thr | Tyr | Phe | Cys | Val | Arg | Phe | Ile | Ser |
| Lys | Gly | Asp | Tyr | Trp | Gly | Gln | Gly | Thr | Ser | Val | Thr | Val | Ser | Ser |
| Ala | Lys | Thr | Thr | Ala | Pro | Ser | Val | Tyr | Pro | Leu | Ala | Pro | Val | Cys |
| Gly | Asp | Thr | Thr | Gly | Ser | Ser | Val | Thr | Leu | Gly | Cys | Leu | Val | Lys |
| Gly | Tyr | Phe | Pro | Glu | Pro | Val | Thr | Leu | Thr | Trp | Asn | Ser | Gly | Ser |
| Leu | Ser | Ser | Gly | Val | His | Thr | Phe | Pro | Ala | Val | Leu | Gln | Ser | Asp |
| Leu | Tyr | Thr | Leu | Ser | Ser | Ser | Val | Thr | Val | Thr | Ser | Ser | Thr | Trp |
| Pro | Ser | Gln | Ser | Ile | Thr | Cys | Asn | Val | Ala | His | Pro | Ala | Ser | Ser |
| Thr | Lys | Val | Asp | Lys | Lys | Ile | Glu | Pro | Arg | Gly | Pro | Thr | Ile | Lys |
| Pro | Cys | Pro | Pro | Cys | Lys | Cys | Pro | Ala | Pro | Asn | Leu | Leu | Gly | Gly |
| Pro | Ser | Val | Phe | Ile | Phe | Pro | Pro | Lys | Ile | Lys | Asp | Val | Leu | Met |
| Ile | Ser | Leu | Ser | Pro | Ile | Val | Thr | Cys | Val | Val | Val | Asp | Val | Ser |
| Glu | Asp | Asp | Pro | Asp | Val | Gln | Ile | Ser | Trp | Phe | Val | Asn | Asn | Val |
| Glu | Val | His | Thr | Ala | Gln | Thr | Gln | Thr | His | Arg | Glu | Asp | Tyr | Asn |
| Ser | Thr | Leu | Arg | Val | Val | Ser | Ala | Leu | Pro | Ile | Gln | His | Gln | Asp |
| Trp | Met | Ser | Gly | Lys | Glu | Phe | Lys | Cys | Lys | Val | Asn | Asn | Lys | Asp |
| Leu | Pro | Ala | Pro | Ile | Glu | Arg | Thr | Ile | Ser | Lys | Pro | Lys | Gly | Ser |
| Val | Arg | Ala | Pro | Gln | Val | Tyr | Val | Leu | Pro | Pro | Pro | Glu | Glu | Glu |
| Met | Thr | Lys | Lys | Gln | Val | Thr | Leu | Thr | Cys | Met | Val | Thr | Asp | Phe |
| Met | Pro | Glu | Asp | Ile | Tyr | Val | Glu | Trp | Thr | Asn | Asn | Gly | Lys | Thr |
| Glu | Leu | Asn | Tyr | Lys | Asn | Thr | Glu | Pro | Val | Leu | Asp | Ser | Asp | Gly |
| Ser | Tyr | Phe | Met | Tyr | Ser | Lys | Leu | Arg | Val | Glu | Lys | Lys | Asn | Trp |
| Val | Glu | Arg | Asn | Ser | Tyr | Ser | Cys | Ser | Val | Val | His | Glu | Gly | Leu |
| His | Asn | His | His | Thr | Thr | Lys | Ser | Phe | Ser | Arg | Thr | Pro | Gly | Lys |

6. The recombinant DNA compound of claim 5 wherein the coding strand is:

7. A recombinant DNA compound that comprises DNA encoding an antibody heavy chain and the signal

| | | | CAG | ATC | CAG | TTG | GTG | CAG | TCT | GGA | CCT | GAG | CTG | AAG |
|---|---|---|---|---|---|---|---|---|---|---|---|---|---|---|
| AAG | CCT | GGA | GAG | ACA | GTC | AAG | ATC | TCC | TGC | AAG | GCT | TCT | GGG | TAT |
| ACC | TTC | ACA | AAC | TAT | GGA | ATG | AAC | TGG | GTG | AAG | CAG | ACT | CCA | GGA |
| AAG | GGT | TTA | AAG | TGG | ATG | GGC | TGG | ATA | AAC | ACC | TAC | ACT | GGA | GAA |
| CCA | ACA | TAT | GCT | GAT | GAC | TTC | AAG | GGA | CGG | TTT | GCC | TTC | TCT | TTG |
| GAA | ACC | TCT | GCC | AGC | ACT | GCC | TTT | TTG | CAG | ATT | CAA | CAA | CCT | CAG |
| AAT | ATG | AGG | ACT | ATG | GCT | ACA | TAT | TTC | TGT | GTA | AGA | TTT | ATT | TCT |
| AAG | GGG | GAC | TAC | TGG | GGT | CAA | GGA | ACG | TCA | GTC | ACC | GTC | TCC | TCA |
| GCC | AAA | ACA | ACA | GCC | CCA | TCG | GTC | TAT | CCA | CTG | GCC | CCT | GTG | TGT |
| GGA | GAT | ACA | ACT | GGC | TCC | TCG | GTG | ACT | CTA | GGA | TGC | CTG | GTC | AAG |
| GGT | TAT | TTC | CCT | GAG | CCA | GTG | ACC | TTG | ACC | TGG | AAC | TCT | GGA | TCC |
| CTG | TCC | AGT | GGT | GTG | CAC | ACC | TTC | CCA | GCT | GTC | CTG | CAG | TCT | GAC |
| CTC | TAC | ACC | CTC | AGC | AGC | TCA | GTG | ACT | GTA | ACC | TCG | AGC | ACC | TGG |
| CCC | AGC | CAG | TCC | ATC | ACC | TGC | AAT | GTG | GCC | CAC | CCG | GCA | AGC | AGC |
| ACC | AAG | GTG | GAC | AAG | AAA | ATT | GAG | CCC | AGA | GGG | CCC | ACA | ATC | AAG |
| CCC | TGT | CCT | CCA | TGC | AAA | TGC | CCA | GCA | CCT | AAC | CTC | TTG | GGT | GGA |
| CCA | TCC | GTC | TTC | ATC | TTC | CCT | CCA | AAG | ATC | AAG | GAT | GTA | CTC | ATG |
| ATC | TCC | CTG | AGC | CCC | ATA | GTC | ACA | TGT | GTG | GTG | GTG | GAT | GTG | AGC |
| GAG | GAT | GAC | CCA | GAT | GTC | CAG | ATC | AGC | TGG | TTT | GTG | AAC | AAC | GTG |
| GAA | GTA | CAC | ACA | GCT | CAG | ACA | CAA | ACC | CAT | AGA | GAG | GAT | TAC | AAC |
| AGT | ACT | CTC | CGG | GTG | GTC | AGT | GCC | CTC | CCC | ATC | CAG | CAC | CAG | GAC |
| TGG | ATG | AGT | GGC | AAG | GAG | TTC | AAA | TGC | AAG | GTC | AAC | AAC | AAA | GAC |
| CTC | CCA | GCG | CCC | ATC | GAG | AGA | ACC | ATC | TCA | AAA | CCC | AAA | GGG | TCA |
| GTA | AGA | GCT | CCA | CAG | GTA | TAT | GTC | TTG | CCT | CCA | CCA | GAA | GAA | GAG |
| ATG | ACT | AAG | AAA | CAG | GTC | ACT | CTG | ACC | TGC | ATG | GTC | ACA | GAC | TTC |
| ATG | CCT | GAA | GAC | ATT | TAC | GTG | GAG | TGG | ACC | AAC | AAC | GGG | AAA | ACA |
| GAG | CTA | AAC | TAC | AAG | AAC | ACT | GAA | CCA | GTC | CTG | GAC | TCT | GAT | GGT |
| TCT | TAC | TTC | ATG | TAC | AGC | AAG | CTG | AGA | GTG | GAA | AAG | AAG | AAC | TGG |
| GTG | GAA | AGA | AAT | AGC | TAC | TCC | TGT | TCA | GTG | GTC | CAC | GAG | GGT | CTG |
| CAC | AAT | CAC | CAC | ACG | ACT | AAG | AGC | TTC | TCC | CGG | ACT | CCG | GGT | AAA |

55 peptide of said heavy chain with the amino acid sequence consisting essentially of:

| | | | | | | | | | | | | | | Met |
|---|---|---|---|---|---|---|---|---|---|---|---|---|---|---|
| Asp | Trp | Leu | Trp | Asn | Leu | Leu | Phe | Leu | Met | Ala | Ala | Ala | Gln | Ser |
| Ala | Gln | Ala | Gln | Ile | Gln | Leu | Val | Gln | Ser | Gly | Pro | Glu | Leu | Lys |
| Lys | Pro | Gly | Glu | Thr | Val | Lys | Ile | Ser | Cys | Lys | Ala | Ser | Gly | Tyr |
| Thr | Phe | Thr | Asn | Tyr | Gly | Met | Asn | Trp | Val | Lys | Gln | Thr | Pro | Gly |
| Lys | Gly | Leu | Lys | Trp | Met | Gly | Trp | Ile | Asn | Thr | Tyr | Thr | Gly | Glu |
| Pro | Thr | Tyr | Ala | Asp | Asp | Phe | Lys | Gly | Arg | Phe | Ala | Phe | Ser | Leu |
| Glu | Thr | Ser | Ala | Ser | Thr | Ala | Phe | Leu | Gln | Ile | Gln | Gln | Pro | Gln |
| Asn | Met | Arg | Thr | Met | Ala | Thr | Tyr | Phe | Cys | Val | Arg | Phe | Ile | Ser |
| Lys | Gly | Asp | Tyr | Trp | Gly | Gln | Gly | Thr | Ser | Val | Thr | Val | Ser | Ser |
| Ala | Lys | Thr | Thr | Ala | Pro | Ser | Val | Tyr | Pro | Leu | Ala | Pro | Val | Cys |
| Gly | Asp | Thr | Thr | Gly | Ser | Ser | Val | Thr | Leu | Gly | Cys | Leu | Val | Lys |
| Gly | Tyr | Phe | Pro | Glu | Pro | Val | Thr | Leu | Thr | Trp | Asn | Ser | Gly | Ser |

-continued

| Leu | Ser | Ser | Gly | Val | His | Thr | Phe | Pro | Ala | Val | Leu | Gln | Ser | Asp |
|---|---|---|---|---|---|---|---|---|---|---|---|---|---|---|
| Leu | Tyr | Thr | Leu | Ser | Ser | Ser | Val | Thr | Val | Thr | Ser | Ser | Thr | Trp |
| Pro | Ser | Gln | Ser | Ile | Thr | Cys | Asn | Val | Ala | His | Pro | Ala | Ser | Ser |
| Thr | Lys | Val | Asp | Lys | Lys | Ile | Glu | Pro | Arg | Gly | Pro | Thr | Ile | Lys |
| Pro | Cys | Pro | Pro | Cys | Lys | Cys | Pro | Ala | Pro | Asn | Leu | Leu | Gly | Gly |
| Pro | Ser | Val | Phe | Ile | Phe | Pro | Pro | Lys | Ile | Lys | Asp | Val | Leu | Met |
| Ile | Ser | Leu | Ser | Pro | Ile | Val | Thr | Cys | Val | Val | Val | Asp | Val | Ser |
| Glu | Asp | Asp | Pro | Asp | Val | Gln | Ile | Ser | Trp | Phe | Val | Asn | Asn | Val |
| Glu | Val | His | Thr | Ala | Gln | Thr | Gln | Thr | His | Arg | Glu | Asp | Tyr | Asn |
| Ser | Thr | Leu | Arg | Val | Val | Ser | Ala | Leu | Pro | Ile | Gln | His | Gln | Asp |
| Trp | Met | Ser | Gly | Lys | Glu | Phe | Lys | Cys | Lys | Val | Asn | Asn | Lys | Asp |
| Leu | Pro | Ala | Pro | Ile | Glu | Arg | Thr | Ile | Ser | Lys | Pro | Lys | Gly | Ser |
| Val | Arg | Ala | Pro | Gln | Val | Tyr | Val | Leu | Pro | Pro | Pro | Glu | Glu | Glu |
| Met | Thr | Lys | Lys | Gln | Val | Thr | Leu | Thr | Cys | Met | Val | Thr | Asp | Phe |
| Met | Pro | Glu | Asp | Ile | Tyr | Val | Glu | Trp | Thr | Asn | Asn | Gly | Lys | Thr |
| Glu | Leu | Asn | Tyr | Lys | Asn | Thr | Glu | Pro | Val | Leu | Asp | Ser | Asp | Gly |
| Ser | Tyr | Phe | Met | Tyr | Ser | Lys | Leu | Arg | Val | Glu | Lys | Lys | Asn | Trp |
| Val | Glu | Arg | Asn | Ser | Tyr | Ser | Cys | Ser | Val | Val | His | Glu | Gly | Leu |
| His | Asn | His | His | Thr | Thr | Lys | Ser | Phe | Ser | Arg | Thr | Pro | Gly | Lys |

8. The recombinant DNA compound of claim 7 wherein the coding strand is:

| | | | | | | | | | | | | | | ATG |
|---|---|---|---|---|---|---|---|---|---|---|---|---|---|---|
| GAT | TGG | CTG | TGG | AAC | TTG | CTA | TTC | CTG | ATG | GCA | GCT | GCC | CAA | AGT |
| GCC | CAA | GCA | CAG | ATC | CAG | TTG | GTG | CAG | TCT | GGA | CCT | GAG | CTG | AAG |
| AAG | CCT | GGA | GAG | ACA | GTC | AAG | ATC | TCC | TGC | AAG | GCT | TCT | GGG | TAT |
| ACC | TTC | ACA | AAC | TAT | GGA | ATG | AAC | TGG | GTG | AAG | CAG | ACT | CCA | GGA |
| AAG | GGT | TTA | AAG | TGG | ATG | GGC | TGG | ATA | AAC | ACC | TAC | ACT | GGA | GAA |
| CCA | ACA | TAT | GCT | GAT | GAC | TTC | AAG | GGA | CGG | TTT | GCC | TTC | TCT | TTG |
| GAA | ACC | TCT | GCC | AGC | ACT | GCC | TTT | TTG | CAG | ATT | CAA | CAA | CCT | CAG |
| AAT | ATG | AGG | ACT | ATG | GCT | ACA | TAT | TTC | TGT | GTA | AGA | TTT | ATT | TCT |
| AAG | GGG | GAC | TAC | TGG | GGT | CAA | GGA | ACG | TCA | GTC | ACC | GTC | TCC | TCA |
| GCC | AAA | ACA | ACA | GCC | CCA | TCG | GTC | TAT | CCA | CTG | GCC | CCT | GTG | TGT |
| GGA | GAT | ACA | ACT | GGC | TCC | TCG | GTG | ACT | CTA | GGA | TGC | CTG | GTC | AAG |
| GGT | TAT | TTC | CCT | GAG | CCA | GTG | ACC | TTG | ACC | TGG | AAC | TCT | GGA | TCC |
| CTG | TCC | AGT | GGT | GTG | CAC | ACC | TTC | CCA | GCT | GTC | CTG | CAG | TCT | GAC |
| CTC | TAC | ACC | CTC | AGC | AGC | TCA | GTG | ACT | GTA | ACC | TCG | AGC | ACC | TGG |
| CCC | AGC | CAG | TCC | ATC | ACC | TGC | AAT | GTG | GCC | CAC | CCG | GCA | AGC | AGC |
| ACC | AAG | GTG | GAC | AAG | AAA | ATT | GAG | CCC | AGA | GGG | CCC | ACA | ATC | AAG |
| CCC | TGT | CCT | CCA | TGC | AAA | TGC | CCA | GCA | CCT | AAC | CTC | TTG | GGT | GGA |
| CCA | TCC | GTC | TTC | ATC | TTC | CCT | CCA | AAG | ATC | AAG | GAT | GTA | CTC | ATG |
| ATC | TCC | CTG | AGC | CCC | ATA | GTC | ACA | TGT | GTG | GTG | GTG | GAT | GTG | AGC |
| GAG | GAT | GAC | CCA | GAT | GTC | CAG | ATC | AGC | TGG | TTT | GTG | AAC | AAC | GTG |
| GAA | GTA | CAC | ACA | GCT | CAG | ACA | CAA | ACC | CAT | AGA | GAG | GAT | TAC | AAC |
| AGT | ACT | CTC | CGG | GTG | GTC | AGT | GCC | CTC | CCC | ATC | CAG | CAC | CAG | GAC |
| TGG | ATG | AGT | GGC | AAG | GAG | TTC | AAA | TGC | AAG | GTC | AAC | AAC | AAA | GAC |
| CTC | CCA | GCG | CCC | ATC | GAG | AGA | ACC | ATC | TCA | AAA | CCC | AAA | GGG | TCA |
| GTA | AGA | GCT | CCA | CAG | GTA | TAT | GTC | TTG | CCT | CCA | CCA | GAA | GAA | GAG |
| ATG | ACT | AAG | AAA | CAG | GTC | ACT | CTG | ACC | TGC | ATG | GTC | ACA | GAC | TTC |
| ATG | CCT | GAA | GAC | ATT | TAC | GTG | GAG | TGG | ACC | AAC | AAC | GGG | AAA | ACA |
| GAG | CTA | AAC | TAC | AAG | AAC | ACT | GAA | CCA | GTC | CTG | GAC | TCT | GAT | GGT |
| TCT | TAC | TTC | ATG | TAC | AGC | AAG | CTG | AGA | GTG | GAA | AAG | AAG | AAC | TGG |
| GTG | GAA | AGA | AAT | AGC | TAC | TCC | TGT | TCA | GTG | GTC | CAC | GAG | GGT | CTG |
| CAC | AAT | CAC | CAC | ACG | ACT | AAG | AGC | TTC | TCC | CGG | ACT | CCG | GGT | AAA |
| TGA | GCT | CAG | CAC | CCA | CAA | AAC | TCT | CAG | GTC | CAA | AGA | GAC | ACC | CAC |

9. A recombinant DNA vector that comprises the DNA sequence of claim 3.

10. A recombinant DNA vector that comprises the DNA sequence of claim 7.

11. The recombinant DNA vector of claim 9 that is plasmid pGKC2310.

12. The recombinant DNA vector of claim 10 that is plasmid pG2A52.

13. A recombinant DNA expression vector of claim 9 that further comprises a promoter and translational activating sequence positioned to drive expression of said DNA.

14. A recombinant DNA expression vector of claim 10 that further comprises a promoter and translational activating sequence positioned to drive expression of said DNA.

15. The recombinant DNA expression vector of claim 13, wherein said promoter is the Adenovirus Late Promoter.

16. The recombinant DNA expression vactor of claim 14, wherein said promoter is the Adenovirus Late Fromoter.

17. A recombinant DNA compound that comprises DNA encoding a chimeric antibody light chain comprising an antigen-specific variable region derived from a first mammalian species and a Constant region derived from a second and different mammalian species, said light chain variable region having an amino acid sequence consisting essentially of:

| | Gln | Ile | Leu | Leu | Thr | Gln | Ser | Pro | Ala | Ile | Met | Ser | Ala | Ser |
|---|---|---|---|---|---|---|---|---|---|---|---|---|---|---|
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |

-continued

| Pro | Trp | Ile | Phe | Asp | Thr | Ser | Asn | Leu | Ala | Ser | Gly | Phe | Pro | Ala |
|-----|-----|-----|-----|-----|-----|-----|-----|-----|-----|-----|-----|-----|-----|-----|
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Gly |     |     |     |     |     |     |     |     |     |     |     |     |

18. The recombinant DNA compound of claim 17 wherein the coding strand is:

|     | CAA | ATT | CTT | CTC | ACC | CAG | TCT | CCA | GCA | ATC | ATG | TCT | GCA | TCT |
|-----|-----|-----|-----|-----|-----|-----|-----|-----|-----|-----|-----|-----|-----|-----|
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |
| ATA | AAA | GGT |     |     |     |     |     |     |     |     |     |     |     |     |

20. The recombinant DNA compound of claim 19 wherein the coding strand is:

|     |     |     |     |     |     |     |     |     | ATG | GAT | TTT | CAA | GTG | CAG |
|-----|-----|-----|-----|-----|-----|-----|-----|-----|-----|-----|-----|-----|-----|-----|
| ATT | TTT | AGC | TTC | CTG | CTA | ATC | AGT | GCT | TCA | GTC | ATA | ATG | TCC | AGA |
| GGA | CAA | ATT | CTT | CTC | ACC | CAG | TCT | CCA | GCA | ATC | ATG | TCT | GCA | TCT |
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |
| ATA | AAA | GGT |     |     |     |     |     |     |     |     |     |     |     |     |

19. A recombinant DNA compound that comprises DNA encoding a chimeric antibody light chain comprising an antigen-specific variable region and signal peptide derived from a first mammalian species and a constant region derived from a second and different mammalian species, said light chain variable region and signal peptide having an amino acid sequence consisting essentially of:

21. A recombinant DNA compound that comprises DNA encoding a chimeric antibody light chain comprising an antigen-specific variable region derived from a first mammalian species and a constant region derived from a second and different mammalian species, said light chain variable region having an amino acid sequence consisting essentially of:

|     | Gln | Ile | Leu | Leu | Thr | Gln | Ser | Pro | Ala | Ile | Met | Ser | Ala | Ser |
|-----|-----|-----|-----|-----|-----|-----|-----|-----|-----|-----|-----|-----|-----|-----|
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |
| Pro | Trp | Ile | Phe | Asp | Thr | Ser | Asn | Leu | Ala | Ser | Gly | Phe | Pro | Ala |
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Arg |     |     |     |     |     |     |     |     |     |     |     |     |

22. The recombinant DNA compound of claim 21 essentially of:

|     |     |     |     |     |     |     |     |     | Met | Asp | Phe | Gln | Val | Gln |
|-----|-----|-----|-----|-----|-----|-----|-----|-----|-----|-----|-----|-----|-----|-----|
| Ile | Phe | Ser | Phe | Leu | Leu | Ile | Ser | Ala | Ser | Val | Ile | Met | Ser | Arg |
| Gly | Gln | Ile | Leu | Leu | Thr | Gln | Ser | Pro | Ala | Ile | Met | Ser | Ala | Ser |
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |
| Pro | Trp | Ile | Phe | Asp | Thr | Ser | Asn | Leu | Ala | Ser | Gly | Phe | Pro | Ala |
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Gly |     |     |     |     |     |     |     |     |     |     |     |     | wherein the coding strand is:

|     | CAA | ATT | CTT | CTC | ACC | CAG | TCT | CCA | GCA | ATC | ATG | TCT | GCA | TCT |
|-----|-----|-----|-----|-----|-----|-----|-----|-----|-----|-----|-----|-----|-----|-----|
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |

-continued

| ATA | AAA | CGT | | | | | | | | | | | | |
|---|---|---|---|---|---|---|---|---|---|---|---|---|---|---|

23. A recombinant DNA compound that comprises DNA encoding a chimeric antibody light chain comprising an antigen-specific variable region and signal peptide derived from a first mammalian species and a constant region derived from a second and different mammalian species, said light chain variable region and signal peptide having an amino acid sequence consisting essentially of:

| | | | | | | Met | Asp | Phe | Gln | Val | Gln | | | |
|---|---|---|---|---|---|---|---|---|---|---|---|---|---|---|
| Ile | Phe | Ser | Phe | Leu | Leu | Ile | Ser | Ala | Ser | Val | Ile | Met | Ser | Arg |
| Gly | Gln | Ile | Leu | Leu | Thr | Gln | Ser | Pro | Ala | Ile | Met | Ser | Ala | Ser |
| Pro | Gly | Glu | Lys | Val | Thr | Met | Thr | Cys | Ser | Ala | Ser | Ser | Ser | Val |
| Ser | Tyr | Met | Leu | Trp | Tyr | Gln | Gln | Lys | Pro | Gly | Ser | Ser | Pro | Lys |
| Pro | Trp | Ile | Phe | Asp | Thr | Ser | Asn | Leu | Ala | Ser | Gly | Phe | Pro | Ala |
| Arg | Phe | Ser | Gly | Ser | Gly | Ser | Gly | Thr | Ser | Tyr | Ser | Leu | Ile | Ile |
| Ser | Ser | Met | Glu | Ala | Glu | Asp | Ala | Ala | Thr | Tyr | Tyr | Cys | His | Gln |
| Arg | Ser | Gly | Tyr | Pro | Tyr | Thr | Phe | Gly | Gly | Gly | Thr | Lys | Leu | Glu |
| Ile | Lys | Arg | | | | | | | | | | | | |

24. The recombinant DNA compound of claim 23 wherein the coding strand is:

| | | | | | | | | ATG | GAT | TTT | CAA | GTG | CAG |
|---|---|---|---|---|---|---|---|---|---|---|---|---|---|
| ATT | TTT | AGC | TTC | CTG | CTA | ATC | AGT | GCT | TCA | GTC | ATA | ATG | TCC | AGA |
| GGA | CAA | ATT | CTT | CTC | ACC | CAG | TCT | CCA | GCA | ATC | ATG | TCT | GCA | TCT |
| CCA | GGG | GAG | AAG | GTC | ACC | ATG | ACC | TGC | AGT | GCC | AGC | TCA | AGT | GTA |
| AGT | TAC | ATG | CTC | TGG | TAC | CAG | CAG | AAG | CCA | GGA | TCC | TCG | CCC | AAA |
| CCC | TGG | ATT | TTT | GAC | ACA | TCC | AAC | CTG | GCT | TCT | GGA | TTC | CCT | GCT |
| CGC | TTC | AGT | GGC | AGT | GGG | TCT | GGG | ACC | TCT | TAC | TCT | CTC | ATA | ATC |
| AGC | AGC | ATG | GAG | GCT | GAA | GAT | GCT | GCC | ACT | TAT | TAC | TGC | CAT | CAG |
| CGG | AGT | GGT | TAC | CCG | TAC | ACG | TTC | GGA | GGG | GGG | ACC | AAG | CTG | GAA |
| ATA | AAA | CGT | | | | | | | | | | | | |

25. A recombinant DNA compound that comprises DNA encoding a chimeric antibody heavy chain comprising an antigen specific variable region derived from a first mammalian species and a constant region derived from a second and different mammalian species, said heavy chain variable region having an amino acid sequence consisting essentially of:

| | | | | | | | | | | | | | | Met |
|---|---|---|---|---|---|---|---|---|---|---|---|---|---|---|
| Asp | Trp | Leu | Trp | Asn | Leu | Leu | Phe | Leu | Met | Ala | Ala | Ala | Gln | Ser |
| Ala | Gln | Ala | Gln | Ile | Gln | Leu | Val | Gln | Ser | Gly | Pro | Glu | Leu | Lys |
| Lys | Pro | Gly | Glu | Thr | Val | Lys | Ile | Ser | Cys | Lys | Ala | Ser | Gly | Tyr |
| Thr | Phe | Thr | Asn | Tyr | Gly | Met | Asn | Trp | Val | Lys | Gln | Thr | Pro | Gly |
| Lys | Gly | Leu | Lys | Trp | Met | Gly | Trp | Ile | Asn | Thr | Tyr | Thr | Gly | Glu |
| Pro | Thr | Tyr | Ala | Asp | Asp | Phe | Lys | Gly | Arg | Phe | Ala | Phe | Ser | Leu |
| Glu | Thr | Ser | Ala | Ser | Thr | Ala | Phe | Leu | Gln | Ile | Gln | Gln | Pro | Gln |

26. The recombinant DNA compound of claim 17 wherein the coding strand is:

| | | | CAG | ATC | CAG | TTG | GTG | CAG | TCT | GGA | CCT | GAG | CTG | AAG |
|---|---|---|---|---|---|---|---|---|---|---|---|---|---|---|
| AAG | CCT | GGA | GAG | ACA | GTC | AAG | ATC | TCC | TGC | AAG | GCT | TCT | GGG | TAT |
| ACC | TTC | ACA | AAC | TAT | GGA | ATG | AAC | TGG | GTG | AAG | CAG | ACT | CCA | GGA |
| AAG | GGT | TTA | AAG | TGG | ATG | GGC | TGG | ATA | AAC | ACC | TAC | ACT | GGA | GAA |
| CCA | ACA | TAT | GCT | GAT | GAC | TTC | AAG | GGA | CGG | TTT | GCC | TTC | TCT | TTG |
| GAA | ACC | TCT | GCC | AGC | ACT | GCC | TTT | TTG | CAG | ATT | CAA | CAA | CCT | CAG |
| AAT | ATG | AGG | ACT | ATG | GCT | ACA | TAT | TTC | TGT | GTA | AGA | TTT | ATT | TCT |
| AAG | GGG | GAC | TAC | TGG | GGT | CAA | GGA | ACG | TCA | GTC | ACC | GTC | TCC | TCA |

27. A recombinant DNA compound that comprises DNA encoding a chimeric antibody heavy chain comprising an antigen-specific variable region and signal peptide derived from a first mammalian species and a constant region derived from a second and different mammalian species, said heavy chain variable region having an amino acid sequence consisting essentially of:

| | | | Gln | Ile | Gln | Leu | Val | Gln | Ser | Gly | Pro | Glu | Leu | Lys |
|---|---|---|---|---|---|---|---|---|---|---|---|---|---|---|
| Lys | Pro | Gly | Glu | Thr | Val | Lys | Ile | Ser | Cys | Lys | Ala | Ser | Gly | Tyr |
| Thr | Phe | Thr | Asn | Tyr | Gly | Met | Asn | Trp | Val | Lys | Gln | Thr | Pro | Gly |
| Lys | Gly | Leu | Lys | Trp | Met | Gly | Trp | Ile | Asn | Thr | Tyr | Thr | Gly | Glu |
| Pro | Thr | Tyr | Ala | Asp | Asp | Phe | Lys | Gly | Arg | Phe | Ala | Phe | Ser | Leu |
| Glu | Thr | Ser | Ala | Ser | Thr | Ala | Phe | Leu | Gln | Ile | Gln | Gln | Pro | Gln |
| Asn | Met | Arg | Thr | Met | Ala | Thr | Tyr | Phe | Cys | Val | Arg | Phe | Ile | Ser |
| Lys | Gly | Asp | Tyr | Trp | Gly | Gln | Gly | Thr | Ser | Val | Thr | Val | Ser | Ser |

| Asn | Met | Arg | Thr | Met | Ala | Thr | Tyr | Phe | Cys | Val | Arg | Phe | Ile | Ser |
| Lys | Gly | Asp | Tyr | Trp | Gly | Gln | Gly | Thr | Ser | Val | Thr | Val | Ser | Ser |

28. The recombinant DNA compound of claim 27 wherein the coding strand is:

| GAT | TGG | CTG | TGG | AAC | TTG | CTA | TTC | CTG | ATG | GCA | GCT | GCC | CAA | ATG |
| GCC | CAA | GCA | CAG | ATC | CAG | TTG | GTG | CAG | TCT | GGA | CCT | GAG | CTG | AGT |
| AAG | CCT | GGA | GAG | ACA | GTC | AAG | ATC | TCC | TGC | AAG | GCT | TCT | GGG | AAG |
| ACC | TTC | ACA | AAC | TAT | GGA | ATG | AAC | TGG | GTG | AAG | CAG | ACT | CCA | TAT |
| AAG | GGT | TTA | AAG | TGG | ATG | GGC | TGG | ATA | AAC | ACC | TAC | ACT | GGA | GGA |
| CCA | ACA | TAT | GCT | GAT | GAC | TTC | AAG | GGA | CGG | TTT | GCC | TTC | TCT | GAA |
| GAA | ACC | TCT | GCC | AGC | ACT | GCC | TTT | TTG | CAG | ATT | CAA | CAA | CCT | TTG |
| AAT | ATG | AGG | ACT | ATG | GCT | ACA | TAT | TTC | TGT | GTA | AGA | TTT | ATT | CAG |
| AAG | GGG | GAC | TAC | TGG | GGT | CAA | GGA | ACG | TCA | GTC | ACC | GTC | TCC | TCT |
| GCC | AAA | ACA | ACA | GCC | CCA | TCG | GTC | TAT | CCA | CTG | GCC | CCT | GTG | TCA |
|     |     |     |     |     |     |     |     |     |     |     |     |     |     | TGT |

29. A recombinant DNA vector that comprises the DNA sequence of claim 17, wherein the first DNA sequence is derived from a murine hybridoma.

30. A recombinant DNA vector that comprises the DNA sequence of claim 19, wherein the first DNA sequence is derived from a murine hybridoma.

31. A recombinant DNA vector that comprises the DNA sequence of claim 21, wherein the first DNA sequence is derived from a murine hybridoma.

32. A recombinant DNA vector that comprises the DNA sequence of claim 23, wherein the first DNA sequence is derived from a murine hybridoma.

33. A recombinant DNA vector that comprises the DNA sequence of claim 25, wherein the first DNA sequence is derived from a murine hybridoma.

34. A recombinant DNA vector that comprises the DNA sequence of claim 27, wherein the first DNA sequence is derived from a murine hybridoma.

35. The recombinant DNA vector of claim 29, wherein the second DNA sequence is derived from a human source.

36. The recombinant DNA vector of claim 30, wherein the second DNA sequence is derived from a human source.

37. The recombinant DNA vector of claim 31, wherein the second DNA sequence is derived from a human source.

38. The recombinant DNA vector of claim 32, wherein the second DNA sequence is derived from a human source.

39. The recombinant DNA vector of claim 33, wherein the second DNA sequence is derived from a human source.

40. The recombinant DNA vector of claim 34, wherein the second DNA sequence is derived from a human source.

41. The recombinant DNA vector of claim 36 that is plasmid CHKC2-18.

42. The recombinant DNA vector of claim 38 that is plasmid CHKC2-6.

43. The recombinant DNA vector of claim 40, wherein the second DNA sequence encodes the constant region of human IgG1.

44. The recombinant DNA vector of claim 40, wherein the second DNA sequence encodes the constant region of human IgG2.

45. The recombinant DNA vector of claim 40, wherein the second DNA sequence encodes the constant region of human IgG3.

46. The recombinant DNA vector of claim 40, wherein the second DNA sequence encodes the constant region of human IgG4.

47. The recombinant DNA vector of claim 43 that is plasmid CH2A5.

48. The recombinant DNA vector of claim 44 that is plasmid CH2A5IG2.

49. The recombinant DNA vector of claim 45 that is plasmid CH2A5IG3.

50. The recombinant DNA vector of claim 46 that is plasmid CH2A5IG4.

51. A recombinant DNA expression vector of claim 36 that further comprises a promoter and translational activating sequence positioned to drive expression of said DNA.

52. A recombinant DNA expression vector of claim 38 that further comprises a promoter and translational activating sequence positioned to drive expression of said DNA.

53. A recombinant DNA expression vector of claim 40 that further comprises a promoter and translational activating sequence positioned to drive expression of said DNA.

54. The recombinant DNA expression vector of claim 51 wherein said promoter is the Adenovirus Late Promoter.

55. The recombinant DNA expression vector of claim 52 wherein said promoter is the Adenovirus Late Promoter.

56. The recombinant DNA expression vector of claim 53 wherein said promoter is the Adenovirus Late Promoter.

57. The recombinant DNA expression vector of claim 61 that is plasmid pL-HD.

58. The recombinant DNA expression vector of claim 56 wherein the second DNA sequence encodes the constant region of human IgG1.

59. The recombinant DNA expression vector of claim 56 wherein the second DNA sequence encodes the constant region of human IgG2.

60. The recombinant DNA expression vector of claim 56 wherein the second DNA sequence encodes the constant region of human IgG3.

61. The recombinant DNA expression vector of claim 56 wherein the second DNA sequence encodes the constant region of human IgG4.

62. The recombinant DNA expression vector of claim 58 that is plasmid pH1-HD.

63. The recombinant DNA expression vector of claim 59 that is plasmid pH2-HD.

64. The recombinant DNA expression vector of claim 60 that is plasmid pH3-HD.

65. The recombinant DNA expression vector of claim 61 that is plasmid pH4-HD.

66. A method for expressing recombinant and chimeric KS1/4 antibody chains in a recombinant non-lymphoid host cell, said method comprising:
(1) transforming said host cell with a recombinant DNA expression vector or vectors that comprise:
 (a) a promoter and translational activating sequence that functions in said non-lymphoid host cell; and
 (b) a DNA sequence that encodes a recombinant or chimeric KS1/4 antibody chain or chains, said DNA sequence being positioned for expression from said promoter and activating sequence; and
(2) culturing said host cell transformed in step (1) under conditions suitable for expression of recombinant or chimeric immunoglobulin chains.

67. The method of claim 66, wherein said recombinant host cell is selected from the group consisting of 293 cells and AV12 cells.

68. The method of claim 67, wherein said recombinant host cell in step 2 is AV12 cells.

69. The method of claim 68, wherein said recombinant host cell in step 2 is AV12/pL-HD.

70. The method of claim 68, wherein said recombinant host cell in step 2 is AV12/pH1-HD.

71. The method of claim 68, wherein said recombinant host cell is step 2 is AV12/pH2-HD.

72. The method of claim 68, wherein said recombinant host cell in step 2 is AV12/pH3-HD.

73. The method of claim 68, wherein said recombinant host cell in step 2 is AV12/pH4-HD.

74. The method of claim 68, wherein said recombinant host cell in step 2 is AV12/pL-HD/pH1-HD.

75. The method of claim 68, wherein said recombinant host cell in step 2 is AV12/pL-HD/pH2-HD.

76. The method of claim 68, wherein said recombinant host cell in step 2 is AV12/pL-HD/pH3-HD.

77. The method of claim 68, wherein said recombinant host cell in step 2 is AV12/pL-HD/pH4-HD.

* * * * *

UNITED STATES PATENT AND TRADEMARK OFFICE
CERTIFICATE OF CORRECTION

PATENT NO. : 4,975,369

DATED : December 4, 1990

INVENTOR(S) : Lisa S. Beavers, et al.

It is certified that error appears in the above-identified patent and that said Letters Patent is hereby corrected as shown below:

In Claim 16, line 3, column 68, please change "Fromoter" to -- Promoter --.

Signed and Sealed this

Eleventh Day of August, 1992

Attest:

DOUGLAS B. COMER

Attesting Officer

Acting Commissioner of Patents and Trademarks

UNITED STATES PATENT AND TRADEMARK OFFICE
CERTIFICATE OF CORRECTION

PATENT NO. : 4,975,369

DATED : December 4, 1990

INVENTOR(S) : Lisa S. Beavers, et al.

It is certified that error appears in the above-identified patent and that said Letters Patent is hereby corrected as shown below:

<u>Col. 68</u>

Claim 16, line 1, "vactor" should read --vector--.

Signed and Sealed this

Thirty-first Day of August, 1993

Attest:

BRUCE LEHMAN

Attesting Officer     Commissioner of Patents and Trademarks